United States Patent
Rothberg et al.

(10) Patent No.: US 7,335,762 B2
(45) Date of Patent: Feb. 26, 2008

(54) APPARATUS AND METHOD FOR SEQUENCING A NUCLEIC ACID

(75) Inventors: Jonathan M. Rothberg, Guilford, CT (US); Joel S. Bader, Stamford, CT (US); Scott B. Dewell, New Haven, CT (US); Keith McDade, Clinton, CT (US); John W. Simpson, Madison, CT (US); Jan Berka, New Haven, CT (US); Christopher M. Colangelo, Old Lyme, CT (US); Michael P. Weiner, Guilford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 384 days.

(21) Appl. No.: 10/222,592

(22) Filed: Aug. 15, 2002

(65) Prior Publication Data

US 2003/0100102 A1 May 29, 2003

Related U.S. Application Data

(63) Continuation of application No. 10/104,280, filed on Mar. 21, 2002, now abandoned, which is a continuation-in-part of application No. 09/814,388, filed on Mar. 21, 2001, which is a continuation-in-part of application No. 09/664,197, filed on Sep. 18, 2000, now abandoned, which is a continuation-in-part of application No. 09/398,833, filed on Sep. 16, 1999, now Pat. No. 6,274,320.

(51) Int. Cl.
*C07H 21/04* (2006.01)
*C12Q 1/68* (2006.01)
*C12P 19/34* (2006.01)

(52) U.S. Cl. .................. 536/24.3; 435/6; 435/91.1; 435/91.2

(58) Field of Classification Search .................. 422/80, 422/82.05; 435/6, 91.1, 91.2; 536/24.3, 536/24.33
See application file for complete search history.

(56) References Cited

U.S. PATENT DOCUMENTS

| | | | |
|---|---|---|---|
| 4,402,568 A | 9/1983 | Kulich et al. ............ 350/96.16 |
| 4,683,195 A | 7/1987 | Mullis et al. | |
| 4,683,202 A | 7/1987 | Mullis | |
| 4,811,218 A | 3/1989 | Hunkapiller et al. | |
| 4,822,746 A | 4/1989 | Walt | |
| 4,863,849 A | 9/1989 | Melamede | |
| 4,965,188 A | 10/1990 | Mullis et al. | |
| 4,971,903 A | 11/1990 | Hyman | |
| 5,114,864 A | 5/1992 | Walt et al. | |
| 5,114,984 A | 5/1992 | Branch et al. | |
| 5,143,853 A | 9/1992 | Walt | |
| 5,171,534 A | 12/1992 | Smith et al. | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,254,477 A | 10/1993 | Walt | |
| 5,298,741 A | 3/1994 | Walt et al. | |
| 5,302,509 A | 4/1994 | Cheeseman | |
| 5,320,814 A | 6/1994 | Walt et al. | |
| 5,354,825 A | 10/1994 | Klainer et al. | |
| 5,405,746 A | 4/1995 | Uhlen | |
| 5,429,807 A | 7/1995 | Matson et al. | |
| 5,436,327 A | 7/1995 | Southern et al. | |
| 5,445,934 A | 8/1995 | Fodor et al. | |
| 5,445,971 A | 8/1995 | Rohr | |
| 5,480,723 A | 1/1996 | Klainer et al. | |
| 5,512,490 A | 4/1996 | Walt et al. | |
| 5,525,464 A | 6/1996 | Drmanac et al. | |
| 5,534,424 A | 7/1996 | Uhlen et al. | |
| 5,587,128 A * | 12/1996 | Wilding et al. ............... 422/50 |
| 5,604,097 A | 2/1997 | Brenner | |
| 5,633,972 A | 5/1997 | Walt et al. | |
| 5,648,245 A | 7/1997 | Fire et al. | |
| 5,700,637 A | 12/1997 | Southern | |
| 5,700,897 A | 12/1997 | Klainer et al. | |
| 5,714,320 A | 2/1998 | Kool | |
| 5,716,785 A | 2/1998 | Van Gelder et al. | |
| 5,728,529 A | 3/1998 | Metzker et al. | |
| 5,744,305 A | 4/1998 | Fodor et al. | |
| 5,750,341 A | 5/1998 | Macevicz | |
| 5,770,367 A | 6/1998 | Southern et al. | |

(Continued)

FOREIGN PATENT DOCUMENTS

EP 0 373 203 8/1994

(Continued)

OTHER PUBLICATIONS

Hyman (1998). *Analytical Biochem.* 174: 423-436.

(Continued)

*Primary Examiner*—Young J. Kim
(74) *Attorney, Agent, or Firm*—Ivor R. Elrifi, Esq.; Mintz Levin Cohn Ferris Glovsky and Popeo PC

(57) ABSTRACT

Disclosed herein are methods and apparatuses for sequencing a nucleic acid. These methods permit a very large number of independent sequencing reactions to be arrayed in parallel, permitting simultaneous sequencing of a very large number (>10,000) of different oligonucleotides.

27 Claims, 15 Drawing Sheets

U.S. PATENT DOCUMENTS

| | | |
|---|---|---|
| 5,780,231 A | 7/1998 | Brenner |
| 5,795,716 A | 8/1998 | Chee |
| 5,800,992 A | 9/1998 | Fodor et al. |
| 5,814,524 A | 9/1998 | Walt et al. |
| 5,821,058 A | 10/1998 | Smith et al. |
| 5,830,662 A | 11/1998 | Soares et al. |
| 5,834,252 A | 11/1998 | Stemmer et al. |
| 5,837,832 A | 11/1998 | Chee et al. |
| 5,846,721 A | 12/1998 | Soares et al. |
| 5,846,727 A | 12/1998 | Soper et al. |
| 5,851,772 A | 12/1998 | Mirzabekov et al. |
| 5,854,033 A | 12/1998 | Lizardi |
| 5,856,104 A | 1/1999 | Chee et al. |
| 5,861,242 A | 1/1999 | Chee et al. |
| 5,871,697 A | 2/1999 | Rothberg et al. |
| 5,871,928 A | 2/1999 | Fodor et al. |
| 5,882,874 A | 3/1999 | Fisher |
| 5,888,819 A | 3/1999 | Goelet |
| 5,891,636 A | 4/1999 | Van Gelder et al. |
| 5,900,481 A | 5/1999 | Lough et al. |
| 5,919,673 A | 7/1999 | Wong et al. |
| 5,928,905 A | 7/1999 | Stemmer et al. |
| 5,962,228 A * | 10/1999 | Brenner ............... 435/6 |
| 5,974,164 A | 10/1999 | Chee |
| 6,013,440 A | 1/2000 | Lipshutz et al. |
| 6,013,445 A | 1/2000 | Albrecht et al. |
| 6,013,449 A | 1/2000 | Hacia et al. |
| 6,023,540 A | 2/2000 | Walt et al. |
| 6,027,880 A | 2/2000 | Cronin et al. |
| 6,040,138 A | 3/2000 | Lockhart et al. |
| 6,040,193 A | 3/2000 | Winkler et al. |
| 6,050,719 A | 4/2000 | Winkler et al. |
| 6,054,270 A | 4/2000 | Southern |
| 6,080,585 A | 6/2000 | Southern et al. |
| 6,114,114 A | 9/2000 | Seilhamer et al. |
| 6,133,436 A | 10/2000 | Koster et al. |
| 6,136,543 A | 10/2000 | Anazawa et al. |
| 6,146,593 A | 11/2000 | Pinkel et al. |
| 6,150,095 A | 11/2000 | Southern et al. |
| 6,156,501 A | 12/2000 | McGall et al. |
| 6,200,737 B1 | 3/2001 | Walt et al. |
| 6,210,891 B1 | 4/2001 | Nyren et al. |
| 6,210,896 B1 | 4/2001 | Chan |
| 6,210,910 B1 | 4/2001 | Walt et al. |
| 6,218,111 B1 | 4/2001 | Southern et al. |
| 6,221,653 B1 | 4/2001 | Caren et al. |
| 6,225,061 B1 | 5/2001 | Becker et al. |
| 6,228,575 B1 | 5/2001 | Gingeras et al. |
| 6,238,862 B1 | 5/2001 | McGall et al. |
| 6,242,180 B1 | 6/2001 | Chee |
| 6,255,476 B1 | 7/2001 | Vinayak et al. |
| 6,258,568 B1 | 7/2001 | Nyren |
| 6,263,286 B1 | 7/2001 | Gilmanshin et al. |
| 6,266,459 B1 | 7/2001 | Walt et al. |
| 6,280,950 B1 | 8/2001 | Lipshutz et al. |
| 6,285,807 B1 | 9/2001 | Walt et al. |
| 6,306,597 B1 | 10/2001 | Macevicz |
| 6,306,643 B1 | 10/2001 | Gentalen et al. |
| 6,307,039 B1 | 10/2001 | Southern |
| 6,309,823 B1 | 10/2001 | Cronin et al. |
| 6,327,410 B1 | 12/2001 | Walt et al. |
| 6,333,155 B1 | 12/2001 | Lockhart et al. |
| 6,342,355 B1 | 1/2002 | Hacia et al. |
| 6,344,316 B1 | 2/2002 | Lockhart et al. |
| 6,355,420 B1 | 3/2002 | Chan |
| 6,355,431 B1 | 3/2002 | Chee et al. |
| 6,368,799 B1 | 4/2002 | Chee |
| 6,377,721 B1 | 4/2002 | Walt et al. |
| 6,396,995 B1 | 5/2002 | Stuelpnagel et al. |
| 6,406,845 B1 | 6/2002 | Walt et al. |
| 6,410,229 B1 | 6/2002 | Lockhart et al. |
| 6,429,027 B1 | 8/2002 | Chee et al. |
| 6,440,677 B2 | 8/2002 | Lipshutz et al. |
| 6,468,744 B1 | 10/2002 | Cronin et al. |
| 6,482,593 B2 | 11/2002 | Walt et al. |
| 6,519,583 B1 | 2/2003 | Koleszar et al. |
| 6,544,732 B1 | 4/2003 | Chee et al. |
| 6,548,257 B2 | 4/2003 | Lockhart et al. |
| 6,576,425 B2 | 6/2003 | McGall et al. |
| 6,607,887 B2 | 8/2003 | Chee |
| 6,611,828 B1 | 8/2003 | Koleszar et al. |
| 6,620,584 B1 | 9/2003 | Chee et al. |
| 6,643,634 B2 | 11/2003 | Koleszar et al. |
| 6,663,832 B2 | 12/2003 | Lebl et al. |
| 6,667,159 B1 | 12/2003 | Walt et al. |
| 6,705,754 B2 | 3/2004 | Winkler et al. |
| 6,720,007 B2 | 4/2004 | Walt et al. |
| 6,733,964 B1 | 5/2004 | Chee et al. |
| 6,742,004 B2 | 5/2004 | Sabatini et al. |
| 6,770,441 B2 | 8/2004 | Dickinson et al. |
| 2001/0006630 A1 | 7/2001 | Yacoby-Zeevi |
| 2001/0029049 A1 | 10/2001 | Walt et al. |
| 2001/0041335 A1 | 11/2001 | Goldberg et al. |
| 2001/0053526 A1 | 12/2001 | Lipshutz et al. |
| 2002/0001801 A1 | 1/2002 | Fan et al. |
| 2002/0006617 A1 | 1/2002 | Fan et al. |
| 2002/0009719 A1 | 1/2002 | Walt et al. |
| 2002/0009729 A1 | 1/2002 | McGall et al. |
| 2002/0012913 A1 | 1/2002 | Gunderson et al. |
| 2002/0012925 A1 | 1/2002 | Chee |
| 2002/0012940 A1 | 1/2002 | Lockhart et al. |
| 2002/0022721 A1 | 2/2002 | Trulson et al. |
| 2002/0025520 A1 | 2/2002 | Chee |
| 2002/0028159 A1 | 3/2002 | Lebl et al. |
| 2002/0039728 A1 | 4/2002 | Kain et al. |
| 2002/0044894 A1 | 4/2002 | Lebl et al. |
| 2002/0051971 A1 | 5/2002 | Stuelpnagel et al. |
| 2002/0071339 A1 | 6/2002 | Winkler et al. |
| 2002/0102578 A1 | 8/2002 | Dickinson et al. |
| 2002/0106663 A1 | 8/2002 | Gentalen et al. |
| 2002/0122612 A1 | 9/2002 | Walt et al. |
| 2002/0132221 A1 | 9/2002 | Chee et al. |
| 2002/0132241 A1 | 9/2002 | Fan et al. |
| 2002/0150909 A1 | 10/2002 | Stuepnagel et al. |
| 2002/0172716 A1 | 11/2002 | Walt et al. |
| 2002/0172946 A1 | 11/2002 | Fan et al. |
| 2002/0177141 A1 | 11/2002 | Chee et al. |
| 2002/0187515 A1 | 12/2002 | Chee et al. |
| 2003/0003490 A1 | 1/2003 | Fan et al. |
| 2003/0013114 A1 | 1/2003 | Lipshutz et al. |
| 2003/0016897 A1 | 1/2003 | Walt et al. |
| 2003/0027126 A1 | 2/2003 | Walt et al. |
| 2003/0064364 A1 | 4/2003 | Lockhart et al. |
| 2003/0082566 A1 | 5/2003 | Sylvan |
| 2003/0096239 A1 | 5/2003 | Gunderson et al. |
| 2003/0104434 A1 | 6/2003 | Fan et al. |
| 2003/0108867 A1 * | 6/2003 | Chee et al. ............... 435/6 |
| 2003/0134291 A1 | 7/2003 | Lipshutz et al. |
| 2003/0157504 A1 | 8/2003 | Chee et al. |
| 2003/0165823 A1 | 9/2003 | Cronin et al. |
| 2003/0165830 A1 | 9/2003 | Cronin et al. |
| 2003/0170684 A1 | 9/2003 | Fan |
| 2003/0175773 A1 | 9/2003 | Chee et al. |
| 2003/0207295 A1 | 11/2003 | Gunderson et al. |
| 2003/0211489 A1 | 11/2003 | Shen et al. |
| 2003/0215821 A1 | 11/2003 | Gunderson et al. |
| 2003/0215841 A1 | 11/2003 | Lockhart et al. |
| 2004/0018491 A1 | 1/2004 | Gunderson et al. |
| 2004/0072202 A1 | 4/2004 | McGall et al. |
| 2004/0076987 A1 | 4/2004 | McGall et al. |
| 2004/0114456 A1 | 6/2004 | Winkler et al. |
| 2004/0121364 A1 | 6/2004 | Chee et al. |
| 2004/0137498 A1 | 7/2004 | Fan et al. |
| 2004/0175718 A1 | 9/2004 | Chee et al. |

| | | | |
|---|---|---|---|
| 2004/0185482 A1 | 9/2004 | Stuelpnagel et al. | |
| 2004/0185483 A1 | 9/2004 | Stuelpnagel et al. | |

FOREIGN PATENT DOCUMENTS

| | | |
|---|---|---|
| EP | 0 371 437 | 2/1996 |
| EP | 0 619 321 | 1/1999 |
| EP | 1 090 293 | 12/1999 |
| EP | 1 196 630 | 10/2000 |
| WO | WO 88/05533 | 7/1988 |
| WO | WO 89/10977 | 11/1989 |
| WO | WO 93/21513 | 10/1993 |
| WO | WO 94/12863 | 6/1994 |
| WO | WO 95/11995 | 5/1995 |
| WO | WO 97/19193 | 5/1997 |
| WO | WO 97/27317 | 7/1997 |
| WO | WO 97/27326 | 7/1997 |
| WO | WO 97/29212 | 8/1997 |
| WO | WO 97/41260 | 11/1997 |
| WO | WO 98/08973 | 3/1998 |
| WO | WO 98/13523 | 4/1998 |
| WO | WO 98/18967 | 5/1998 |
| WO | WO 98/20019 | 5/1998 |
| WO | WO 98/28440 | 7/1998 |
| WO | WO 98/30883 | 7/1998 |
| WO | WO 98/35012 | 8/1998 |
| WO | WO 98/38846 | 9/1998 |
| WO | WO 98/40726 | 9/1998 |
| WO | WO 98/41657 | 9/1998 |
| WO | WO 98/44151 | 10/1998 |
| WO | WO 98/44152 | 10/1998 |
| WO | WO 98/50782 | 11/1998 |
| WO | WO 98/53300 | 11/1998 |
| WO | WO 98/56954 | 12/1998 |
| WO | WO 98/58079 | 12/1998 |
| WO | WO 98/58529 | 12/1998 |
| WO | WO 99/05315 | 2/1999 |
| WO | WO 99/07896 | 2/1999 |
| WO | WO 99/14228 | 3/1999 |
| WO | WO 99/15702 | 4/1999 |
| WO | WO 99/18434 | 4/1999 |
| WO | WO 99/28494 | 6/1999 |
| WO | WO 99/30823 | 6/1999 |
| WO | WO 99/36576 | 7/1999 |
| WO | WO 99/39004 | 8/1999 |
| WO | WO 99/45357 | 9/1999 |
| WO | WO 99/53102 | 10/1999 |
| WO | WO 99/60007 | 11/1999 |
| WO | WO 99/61662 | 12/1999 |
| WO | WO 99/66313 | 12/1999 |
| WO | WO 99/67641 | 12/1999 |
| WO | WO 00/06770 | 2/2000 |
| WO | WO 00/11223 | 3/2000 |
| WO | WO 00/13004 | 3/2000 |
| WO | WO 00/16101 | 3/2000 |
| WO | WO 00/27521 | 5/2000 |
| WO | WO 00/29832 | 5/2000 |
| WO | WO 00/39587 | 7/2000 |
| WO | WO 00/43540 | 7/2000 |
| WO | WO 00/44491 | 8/2000 |
| WO | WO 00/47996 | 8/2000 |
| WO | WO 00/48000 | 8/2000 |
| WO | WO 00/56455 | 8/2000 |
| WO | WO 00/58507 | 10/2000 |
| WO | WO 00/60072 | 10/2000 |
| WO | WO 00/60114 | 10/2000 |
| WO | WO 00/60332 | 10/2000 |
| WO | WO 00/63437 | 10/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/12862 | 2/2001 |
| WO | WO 01/18524 | 3/2001 |
| WO | WO 01/24937 | 4/2001 |
| WO | WO 01/25480 | 4/2001 |
| WO | WO 01/41918 | 6/2001 |
| WO | WO 01/42496 | 6/2001 |
| WO | WO 01/46675 | 6/2001 |
| WO | WO 01/57268 | 8/2001 |
| WO | WO 01/57269 | 8/2001 |
| WO | WO 01/59432 | 8/2001 |
| WO | WO 01/61043 | 8/2001 |
| WO | WO 01/69245 | 9/2001 |
| WO | WO 01/85341 | 11/2001 |
| WO | WO 02/00336 | 1/2002 |
| WO | WO 02/12897 | 2/2002 |
| WO | WO 02/16649 | 2/2002 |
| WO | WO 02/20836 | 3/2002 |
| WO | WO 02/20837 | 3/2002 |
| WO | WO 02/21128 | 3/2002 |
| WO | WO 02/28530 | 4/2002 |
| WO | WO 02/41987 | 5/2002 |
| WO | WO 02/099982 | 12/2002 |

OTHER PUBLICATIONS

Mitra and Church (1999). *Nuc. Acids Res.* 27(e34): i-iv.
Tawfik and Griffiths (1998). *Nature Biotechnol.* 16: 652-656.
Baner et al., "Signal amplification of padlock probes by rolling circle replication." Nucleic Acids Research 26(22): 5073-5078 (1998).
Barshop et al., "Luminescent immobilized enzyme test systems for inorganic pyrophosphate: Assays using firefly luciferase and nicotinamide-mononucleotide adenylyl transferase or adenosine-5'-triphosphate sulfurylase." Analytical Biochemistry 197: 266-272 (1991).
Brandis et al., "Slow rate of phosphodiester bond formation accounts for the strong bias that Taq DNA polymerase shows against 2', 3'-dideoxynucleotide terminators." Biochemistry 55: 2189-2200 (1990).
Bronk et al., "Combined imaging and chemical sensing using a single optical imaging fiber." Anal. Chem. 67: 2750-2757 (1996).
Burns et al., "An Integrated Nanoliter DNA Analysis Device." Science 282: 484-487 (1998).
Chan and Nie, "Quantum dot bioconjugates for ultrasensitive nonisotopic detection." Scient 218: 2016-2018 (1998).
Chee et al., "Accessing Genetic Information with High-Density DNA Arrays." Science 274(5287).
Chiu and Christopoulos, "Hybridization Assays Using an Expressible DNA Fragment Encoding Firefly Luciferase as a label." Anal. Chem. 68: 2304-2308 (1996).
Daubendiek and Kool, "Generation of catalytic RNAs by rolling transcription of synthetic DNA nanocircles." Nature Biotechnology 15: 273-277 (1997).
Dickson et al., "Three-dimensional imaging of single molecules solvated in pores of poly(acrylamide) gels." Science 274(5289): 966 (1996).
Dickson et al., "On/off blinking and switching behaviour of single molecules of green fluorescent protein." Nature 388: 355-358 (1997).
Ferguson et al., "A fiber-optic DNA biosensor microarray for the analysis of gene expression." Nature Biotechnology 14: 1681-1684 (1996).
Fire and Xu, "Rolling replication of short DNA circles." Proc. Natl. Acad. Sci. 92: 4641-4645 (1995).
Ha et al., "Probing the interaction between two single molecules: Fluorescence resonance energy transfer between a single donor and a single acceptor." Proc. Natl. Acad. 93: 6264-6268 (1996).
Hacia, "Resequencing and mutational analysis using oligonucleotide microarrays." Nature Genetics Supplement 21: 42-47 (1999).
Hatch et al., "Rolling circle amplification of DNA immobilized on solid surfaces and its application to multiplex mutation detection." Genetic Analysis: Biomolecular Engineering 15: 35-40 (1999).

Healey and Walt, "Fast Temporal Response Fiber-Optic Chemical Sensors Based on the Photodeposition of Micrometer-scale Polymer Arrays." Anal. Chem. 69: 2213-2216 (1997).

Healey et al., "Photodeposition of Micrometer-Scale Polymer Patterns on Optical Imaging Fibers." Science 269: 1078-1080 (1995).

Hengsakul and Cass, "Protein Patterning with a Photoactivatable Derivative of Biotin." Bioconjugate Chem. 7: 249-254 (1996).

Ishijima et al., "Simultaneous observation of Individual ATPase and Mechanical Events by a Single Myosin Molecule during Interaction with Actin." Cell 92: 161-171 (1998).

Ito et al., "Fluorescent differential display: arbitrarily primed RT-PCR fingerprinting on an automated DNA sequencer." FEBS 351: 231-236 (1994).

Izawa et al., "Recognition Sites of 3'-OH Group by T7 RNA Polymerase and Its Application to Transcriptional Sequencing." The Journal of Biological Chemistry 273(23): 14242-14246 (1998).

Karamohamed et al., "Production, Purification, and Luminometric Analysis of Recombinant Saccharomyces cerevisiae MET3 Adenosine Triphosphate Sulfurylase Expressed in Escherichia coli." Protein Expression and Purification 15: 381-388 (1999).

Karamohamed and Nyren, "Real-Time Detection and Quantification of Adenosine Triphosphate Sulfurylase Activity by a Bioluminometric Approach." Analytical Biochemistry 271: 81-85 (1999).

Keller et al., "Single-Molecule Fluorescence Analysis in Solution." Applied Spectroscopy 7(50): 823-958 (1996).

Kievits et al., "NASBA isothermal enzymatic in vitro nucleic acid amplification optimized for the diagnosis of HIV-1 infection." Journal of Virological Methods 35: 273-286 (1991).

Kricka, "Miniaturization of analytical systems." Clinical Chemistry 44(9): 2008-2014 (1998).

Lander, "the New Genomics: Global Views of Biology." Science 274: 536-539 (1996).

Lu et al., "Rolling Circle DNA Synthesis: Small Circular Oligonucleotides as Efficient Templates for DNA Polymerases." J. Am. Chem. Soc. 118: 1587-1594 (1996).

Lizardi et al., "Mutation detection and single-molecule counting using isothermal rolling-circle amplification." Nature Genetics 19: 225-232 (1998).

Metzker et al., "Elimination of Residual Natural Nucleotides from 3'-O-Modified-dNTP Syntheses by Enzymatic Mop-Up." BioTechniques 25: 814-817 (1998).

Metzker et al., "Quantitation of Mixed-Base Populations of HIV-1 Variants by Automated DNA Sequencing with BODIPY Dye-Labeled Primers." BioTechniques 25: 446-462 (1998).

Munkholm and Walt, "Polymer Modification of Fiber Optic Chemical Sensors as a Method of Enhancing Fluorescence Signal for pH Measurement." Anal. Chem. 58: 1427-1430 (1986).

Mooney et al., "Patterning of functional antibodies and other proteins by photolithography of silane monolayers." Proc. Natl. Acad. Sci. 93: 12287-12291 (1996).

Narang et al., "Fiber Optic-based biosensor for ricin." Biosensors & Bioelectronics 12(9-10): 937-945 (1997).

Nie et al., "Probing Individual Molecules with Confocal Fluorescence Microscopy." Science 266: 1018-1021 (1994).

Nie and Zare, "Optical Detection of Single Molecules." Annu. Rev. Biophys. Biomol. Struct. 26: 567-596 (1997).

Nilsson et al., "Padlock probes reveal single-nucleotide differences, parent of origin and in situ distribution of centromeric sequences in human chromosomes 13 and 21." Nature Genetics 16: 252-255 (1997).

Nilsson et al., "Padlock Probes: Circularizing Oligonucleotides for Localized DNA Detection." Science 265: 2085-2087 (1994).

Nyren, "Apyrase Immobilized on Paramagnetic Beads Used to Improve Detection Limits in Bioluminometric ATP Monitoring." J. Biolumin. Chemilumin.

Nyren et al., "Detection of Single-Base Changes Using a Bioluminometric Primer Extension Assay." Analytical Biochemistry 244: 367-373 (1997).

Nyren et al., "Solid Phase DNA Minisequencing by an Enzymatic Luminometric Inorganic Pyrophosphate Detection Assay." Analytical Biochemistry 208: 171-175 (1993).

Oker-Blom et al., "A Baculovirus-Expressed Fusion Protein Containing the Antibody-Binding Doman of Protein A and Insect Luciferase." BioTechniques 14(5): 800-807 (1993).

Parthasarathy and Martin, "Synthesis of polymeric microcapsule arrays and their use for enzyme immobilization." Nature 369: 298-301 (1994).

Pierce et al., "Imaging individual green fluorescent proteins." Scientific Correspondence.

Pirrung and Huang, "A General method for the Spatially Defined Immobilization of Biomolecules on Glass Surfaces Using "Caged" Biotin." Bioconjugate Chem. 7: 317-321 (1996).

Rawlinson et al., "Analysis of the Complete DNA Sequence of Murine Cytomegalovirus." Journal of Virology 8833-8849 (1996).

Ribeiro et al., "Immobilization of Luciferase from a Firefly Lantern Extract on Glass Strips as an Alternative Strategy for Luminescent Detection of ATP." J. Biolumin Chemilumin 13: 371-378 (1998).

Ronaghi et al., "Real-Time DNA Sequencing Using Detection of Pyrophosphate Release." Analytical Biochemistry 242: 84-89 (1996).

Ronaghi et al., "A Sequencing Method Based on Real-Time Pyrophosphate." Science 281: 363. 365 (1998).

Ronaghi et al., "Analyses of Secondary Structures in DNA by Pyrosequencing." Analytical Biochemistry 267: 65-71 (1999).

Ronaghi, "Pyrosequencing: A Tool for Sequence-Based DNA Analysis." Royal Institute of Technology Department of Technology.

Service, "Microchip Arrays Put DNA on the Spot." Science 282(5388).

Venter et al., "Shotgun Sequencing of the Human Genome." Science 280(5369): 1540.

Walker et al., "Strand displacement amplification—an isothermal, in vitro DNA amplification technique." Nucleic Acids Research 20(7): 1691-1696 (1992).

Walker et al., "Isothermal in vitro amplification of DNA by a restriction enzyme/DNA polymerase system." Proc. Natl. Acad. 89: 392-396 (1992).

Wang et al., "Specific Immobilization of Firefly Luciferase through a Biotin Carboxyl Carrier Protein Domain." Analytical Biochemistry 246: 133-139 (1997).

Wang et al., "Large-Scale Identification, Mapping, and Genotyping of Single-Nucleotide Polymorphisms in the Human Genome." Science 280: 1077-1082 (1998).

Wang et al., "Force and Velocity Measured for single Molecules of RNA Polymerase." Science 282: 902-907 (1998).

Weisiger, "Impact of Extracellular Diffusion on Hepatic Uptake Kinetics." ASTRACT: 1-26.

Wooster et al., "Localization of a Breast Cancer Susceptibility Gene, BRCA2, to Chromosome 13q12-13." Science 265: 277-285 (1994).

Xie and Lu, "Single-molecule Enzymology." The Journal of Biological Chemistry 274(23): 15967-15970 (1999).

Yin et al., "Transcription Against an Applied Force." Science 270: 1653-1657.

Nyren, "Enzymatic Method for Continuous Monitoring of DNA Polymerase Activity." Analytical Biochemistry 167: 235-238 (1987).

Hoheisel, "Oligomer-chip technology" Trends in BioTechnology, 15: 465-469.

Pantano et al., "Ordered Nanowell Arrays" Chemistry of Materials, 8: 2832-2835.

International Search Report for PCT/US00/25290, mailed Nov. 28, 2001.

International Search Report for PCT/US02/08700, mailed Jul. 12, 2002.

* cited by examiner

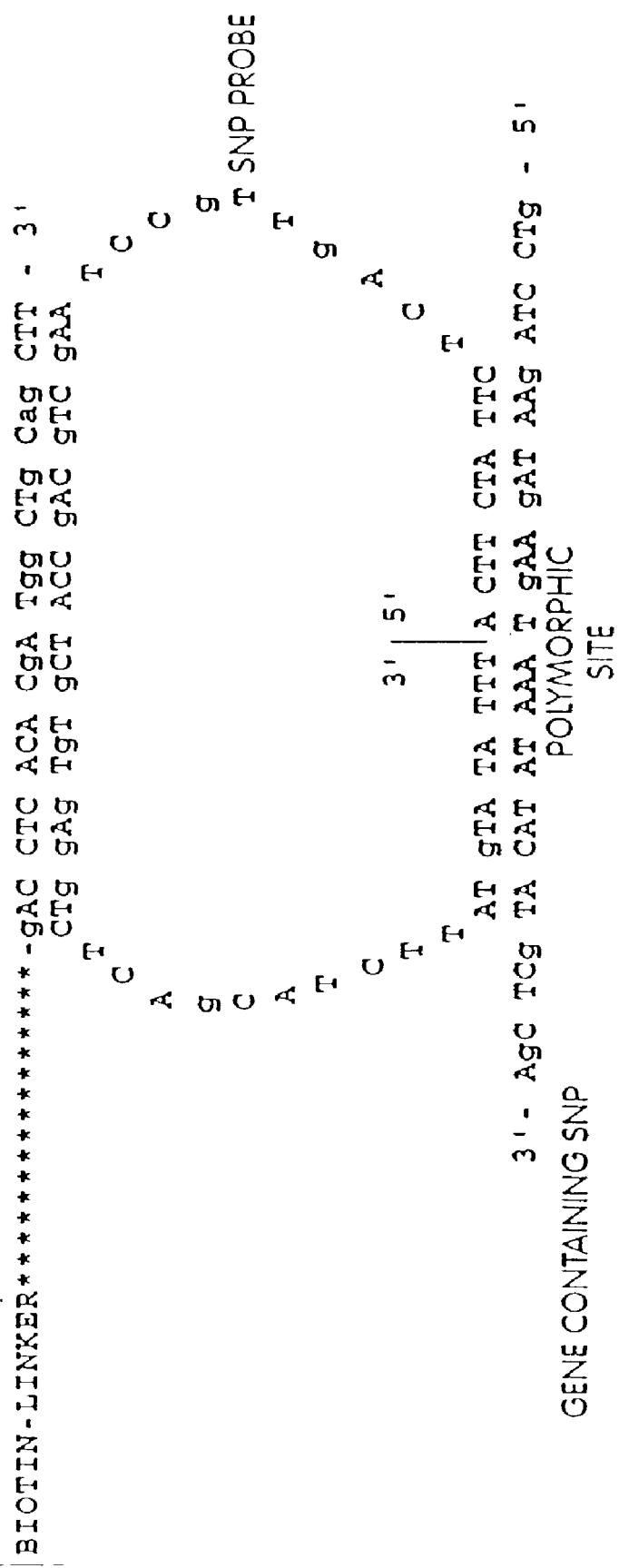

Sulfurylase on mobile support/Luciferase on surface, PPi flows across FORA surface. 1 mobile-support per pixel on camera; 50μm FORA well spanning 4 15μm pixels. Shown is 100 x 100 Pixels (10K pixels), 1.5 mm².

_US 7,335,762 B2_

SEQUENCE LISTING

<160> NUMBER OF SEQ ID NOS: 9

<210> SEQ ID NO 1
<211> LENGTH: 64
<212> TYPE: DNA
<213> ORGANISM: Homo sapiens

<400> SEQUENCE: 1
tcgtgtgagg tctcagcatc ttatgtatat ttacttctat tctcagttgc ctaagctgca    60
gcca    64

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: anchor
      primer

<400> SEQUENCE: 2
gacctcacac gatggctgca gctt    24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: anchor
      primer

<400> SEQUENCE: 3
gacctcacac gatggctgca gctt    24

<210> SEQ ID NO 4
<211> LENGTH: 64
<212> TYPE: DNA
<213> ORGANISM: Artificial Sequence
<220> FEATURE:
<223> OTHER INFORMATION: Description of Artificial Sequence: SNP probe

<400> SEQUENCE: 4

-continued

```
tttatatgta ttctacgact ctggagtgtg ctaccgacgt cgaatccgtt gactcttatc    60
ttca                                                                 64

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: SNP region
      of gene

<400> SEQUENCE: 5
ctagctcgta catataaatg aagataagat cctg                                34

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: anchor
      primer

<400> SEQUENCE: 6
gacctcacac gagtagcatg gctgcagctt                                     30

<210> SEQ ID NO 7
<211> LENGTH: 64
<212> TYPE: DNA
<213> ORGANISM: Homo sapiens

<400> SEQUENCE: 7
tcgtgtgagg tctcagcatc ttatgtatat ttacttctat tctcagttgc ctaagctgca    60
gcca                                                                 64

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: sequencing
      primer

<400> SEQUENCE: 8
aagctgcagc catcgtgtga gg                                             22

<210> SEQ ID NO 9
<211> LENGTH: 19
<212> TYPE: DNA
<213> ORGANISM: Homo sapiens

<400> SEQUENCE: 9
ggggaattca aaatttggc                                                 19
```

APPARATUS AND METHOD FOR SEQUENCING A NUCLEIC ACID

RELATED APPLICATIONS

This application claims the benefit of priority to U.S. Ser. No. 10/104,280 filed Mar. 21, 2002, abandoned; which is a continuation-in-part of U.S. Ser. No. 09/814,338 filed Mar. 21, 2001; which is a continuation-in-part of U.S. Ser. No. 09/664,197 filed Sep. 18, 2000, abandoned; which is a continuation-in-part of U.S. Ser. No. 09/398,833 filed Sep. 16, 1999, now U.S. Pat. No. 6,274,320. Each of the above referenced patent and patent applications is incorporated herein by reference in its entirety.

FIELD OF THE INVENTION

The invention relates to apparatus and methods for determining the sequence of a nucleic acid.

BACKGROUND OF THE INVENTION

Many diseases are associated with particular DNA sequences. The DNA sequences are often referred to as DNA sequence polymorphisms to indicate that the DNA sequence associated with a diseased state differs from the corresponding DNA sequence in non-afflicted individuals DNA sequence polymorphisms can include, e.g., insertions, deletions, or substitutions of nucleotides in one sequence relative to a second sequence. An example of a particular DNA sequence polymorphism is 5'-ATCG-3', relative to the sequence 5'-ATGG-3' at a particular location in the human genome. The first nucleotide 'G' in the latter sequence has been replaced by the nucleotide 'C' in the former sequence. The former sequence is associated with a particular disease state, whereas the latter sequence is found in individuals not suffering from the disease. Thus, the presence of the nucleotide sequence '5-ATCG-3' indicates the individual has the particular disease. This particular type of sequence polymorphism is known as a single-nucleotide polymorphism, or SNP, because the sequence difference is due to a change in one nucleotide.

Techniques which enable the rapid detection of as little as a single DNA base change are therefore important methodologies for use in genetic analysis. Because the size of the human genome is large, on the order of 3 billion base pairs, techniques for identifying polymorphisms must be sensitive enough to specifically identify the sequence containing the polymorphism in a potentially large population of nucleic acids.

Typically a DNA sequence polymorphism analysis is performed by isolating DNA from an individual, manipulating the isolated DNA, e.g., by digesting the DNA with restriction enzymes and/or amplifying a subset of sequences in the isolated DNA. The manipulated DNA is then examined further to determine if a particular sequence is present.

Commonly used procedures for analyzing the DNA include electrophoresis. Common applications of electrophoresis include agarose or polyacrylamide gel electrophoresis. DNA sequences are inserted, or loaded, on the gels and subjected to an electric field. Because DNA carries a uniform negative charge, DNA will migrate through the gel based on properties including sequence length, three-dimensional conformation and interactions with the gel matrix upon application of the electrical field. In most applications, smaller DNA molecules will migrate more rapidly through the gel than larger fragments. After electrophoresis has been continued for a sufficient length of time, the DNA molecules in the initial population of DNA sequences will have been separated according to their relative sizes.

Particular DNA molecules can then be detected using a variety of detection methodologies. For some applications, particular DNA sequences are identified by the presence of detectable tags, such as radioactive labels, attached to specific DNA molecules.

Electrophoretic-based separation analyses can be less desirable for applications in which it is desirable to rapidly, economically, and accurately analyze a large number of nucleic acid samples for particular sequence polymorphisms. For example, electrophoretic-based analysis can require a large amount of input DNA. In addition, processing the large number of samples required for electrophoretic-based nucleic acid based analyses can be labor intensive. Furthermore, these techniques can require samples of identical DNA molecules, which must be created prior to electrophoresis at costs that can be considerable.

Recently, automated electrophoresis systems have become available. However, electrophoresis can be ill suited for applications such as clinical sequencing, where relatively cost-effective units with high throughput are needed. Thus, the need for non-electrophoretic methods for sequencing is great. For many applications, electrophoresis is used in conjunction with DNA sequence analysis.

Several alternatives to electrophoretic-based sequencing have been described. These include scanning tunnel electron microscopy, sequencing by hybridization, and single molecule detection methods.

Another alternative to electrophoretic-based separation analysis is solid substrate-based nucleic acid analyses. These methods typically rely upon the use of large numbers of nucleic acid probes affixed to different locations on a solid support. These solid supports can include, e.g., glass surfaces, plastic microtiter plates, plastic sheets, thin polymers, or semi-conductors. The probes can be, e.g., adsorbed or covalently attached to the support, or can be microencapsulated or otherwise entrapped within a substrate matrix, membrane, or film.

Substrate-based nucleic acid analyses can include applying a sample nucleic acid known or suspected of containing a particular sequence polymorphism to an array of probes attached to the solid substrate. The nucleic acids in the population are allowed to hybridize to complementary sequences attached to the substrate, if present. Hybridizing nucleic acid sequences are then detected in a detection step.

Solid support matrix-based hybridization and sequencing methodologies can require a high sample-DNA concentration and can be hampered by the relatively slow hybridization kinetics of nucleic acid samples with immobilized oligonucleotide probes. Often, only a small amount of template DNA is available, and it can be desirable to have high concentrations of the target nucleic acid sequence. Thus, substrate based detection analyses often include a step in which copies of the target nucleic acid, or a subset of sequences in the target nucleic acid, is amplified. Methods based on the Polymerase Chain Reaction (PCR), e.g., can increase a small number of probe targets by several orders of magnitude in solution. However, PCR can be difficult to incorporate into a solid-phase approach because the amplified DNA is not immobilized onto the surface of the solid support matrix.

Solid-phase based detection of sequence polymorphisms has been described. An example is a "mini-sequencing" protocol based upon a solid phase principle described by Hultman, et al., 1988. _Nucl. Acid. Res._ 17: 4937-4946;

Syvanen, et al., 1990 *Genomics* 8: 684-692. In this study, the incorporation of a radiolabeled nucleotide was measured and used for analysis of a three-allelic polymorphism of the human apolipoprotein E gene. However, such radioactive methods are not well suited for routine clinical applications, and hence the development of a simple, highly sensitive non-radioactive method for rapid DNA sequence analysis has also been of great interest.

SUMMARY OF THE INVENTION

The invention is based in part on the use of arrays for determining the sequences of nucleic acids.

Accordingly, in one aspect, the invention involves an array including a planar surface with a plurality of reaction chambers disposed thereon, wherein the reaction chambers have a center to center spacing of between 5 to 200 μm and each chamber has a width in at least one dimension of between 0.3 μm and 100 μm. In some embodiments, the array is a planar surface with a plurality of cavities thereon, where each cavity forms an analyte reaction chamber. In a preferred embodiment, the array is fashioned from a sliced fiber optic bundle (i.e., a bundle of fused fiber optic cables) and the reaction chambers are formed by etching one surface of the fiber optic reactor array ("FORA"). The cavities can also be formed in the substrate via etching, molding or micromachining.

Specifically, each reaction chamber in the array typically has a width in at least one dimension of between 0.3 μm and 100 μm, preferably between 0.3 μm and 20 μm, mst preferably between 0.3 μm and 10 μm. In a separate embodiment, we contemplate larger reaction chambers, preferably having a width in at least one dimension of between 20 μm and 70 μm.

The array typically contains more than 1,000 reaction chambers, preferably more than 400,000, more preferably between 400,000 and 20,000,000, and most preferably between 1,000,000 and 16,000,000 cavities or reaction chambers. The shape of each cavity is frequently substantially hexagonal, but the cavities can also be cylindrical. In some embodiments, each cavity has a smooth wall surface, however, we contemplate that each cavity may also have at least one irregular wall surface. The bottom of each of the cavities can be planar or concave.

The array is typically constructed to have cavities or reaction chambers with a center-to-center spacing between 10 to 150 μm, preferably between 50 to 100 μm.

Each cavity or reaction chamber typically has a depth of between 10 μm and 100 μm; alternatively, the depth is between 0.25 and 5 times the size of the width of the cavity, preferably between 0.3 and 1 times the size of the width of the cavity.

In one embodiment, the arrays described herein typically include a planar top surface and a planar bottom surface, which is optically conductive such that optical signals from the reaction chambers can be detected through the bottom planar surface In these arrays, typically the distance between the top surface and the bottom surface is no greater than 10 cm, preferably no greater than 3 cm, most preferably no greater than 2 cm and usually between 0.5 mm to 5 mm.

In one embodiment, each cavity of the array contains reagents for analyzing a nucleic acid or protein. The array can also include a second surface spaced apart from the planar array and in opposing contact therewith such that a flow chamber is formed over the array.

In another aspect, the invention involves an array means for carrying out separate parallel common reactions in an aqueous environment, wherein the array means includes a substrate having at least 1,000 discrete reaction chambers. These chambers contain a starting material that is capable of reacting with a reagent. Each of the reaction chambers are dimensioned such that when one or more fluids containing at least one reagent is delivered into each reaction chamber, the diffusion time for the reagent to diffuse out of the well exceeds the time required for the starting material to react with the reagent to form a product. The reaction chambers can be formed by generating a plurality of cavities on the substrate, or by generating discrete patches on a planar surface, the patches having a different surface chemistry than the surrounding planar surface.

In one embodiment, each cavity or reaction chamber of the array contains reagents for analyzing a nucleic acid or protein. Typically those reaction chambers that contain a nucleic acid (not all reaction chambers in the array are required to) contain only a single species of nucleic acid (i.e., a single sequence that is of interest). There may be a single copy of this species of nucleic acid in any particular reaction chamber, or they may be multiple copies. It is generally preferred that a reaction chamber contain at least 100 copies of a nucleic acid sequence, preferably at least 100,000 copies, and most preferably between 100,000 to 1,000,000 copies of the nucleic acid. In one embodiment the nucleic acid species is amplified to provide the desired number of copies using PCR, RCA, ligase chain reaction, other isothermal amplification, or other conventional means of nucleic acid amplification. In one embodiment, the nucleic acid is single stranded. In other embodiments the single stranded DNA is a concatamer with each copy covalently linked end to end.

The nucleic acid may be immobilized in the reaction chamber, either by attachment to the chamber itself or by attachment to a mobile solid support that is delivered to the chamber. A bioactive agent could be delivered to the array, by dispersing over the array a plurality of mobile solid supports, each mobile solid support having at least one reagent immobilized thereon, wherein the reagent is suitable for use in a nucleic acid sequencing reaction.

The array can also include a population of mobile solid supports disposed in the reaction chambers, each mobile solid support having one or more bioactive agents (such as a nucleic acid or a sequencing enzyme) attached thereto. The diameter of each mobile solid support can vary, we prefer the diameter of the mobile solid support to be between 0.01 to 0.1 times the width of each cavity. Not every reaction chamber need contain one or more mobile solid supports. There are three contemplated embodiments; one where at least 5% to 20% of of the reaction chambers can have a mobile solid support having at least one reagent immobilized thereon; a second embodiment where 20% to 60% of the reaction chambers can have a mobile solid support having at least one reagent immobilized thereon; and a third embodiment where 50% to 100% of the reaction chambers can have a mobile solid support having at least one reagent immobilized thereon.

The mobile solid support typically has at least one reagent immobilized thereon. For the embodiments relating to pyrosequencing reactions or more generally to ATP detection, the reagent may be a polypeptide with sulfurylase or luciferase activity, or both. The mobile solid supports can be used in methods for dispersing over the array a plurality of mobile solid supports having one or more nucleic sequences or proteins or enzymes immobilized thereon.

In another aspect, the invention involves an apparatus for simultaneously monitoring the array of reaction chambers for light generation, indicating that a reaction is taking place at a particular site. In this embodiment, the reaction chambers are sensors, adapted to contain analytes and an enzymatic or fluorescent means for generating light in the reaction chambers. In this embodiment of the invention, the sensor is suitable for use in a biochemical or cell-based assay. The apparatus also includes an optically sensitive device arranged so that in use the light from a particular reaction chamber would impinge upon a particular predetermined region of the optically sensitive device, as well as means for determining the light level impinging upon each of the predetermined regions and means to record the variation of the light level with time for each of the reaction chamber.

In one specific embodiment, the instrument includes a light detection means having a light capture means and a second fiber optic bundle for transmitting light to the light detecting means. We contemplate one light capture means to be a CCD camera. The second fiber optic bundle is typically in optical contact with the array, such that light generated in an individual reaction chamber is captured by a separate fiber or groups of separate fibers of the second fiber optic bundle for transmission to the light capture means.

The above arrays may be used for carrying out separate parallel common reactions in an aqueous environment. The method includes delivering a fluid containing at least one reagent to the described arrays, wherein certain reaction chambers (not necessarily all) on the array contain a starting material that is capable of reacting with the reagent. Each of the reaction chambers is dimensioned such that when the fluid is delivered into each reaction chamber, the diffusion time for the reagent to diffuse out of the well exceeds the time required for the starting material to react with the reagent to form a product. The method also includes washing the fluid from the array in the time period after the starting material has reacted with the reagent to form a product in each reaction chamber but before the reagent delivered to any one reaction chamber has diffused out of that reaction chamber into any other reaction chamber. In one embodiment, the product formed in any one reaction chamber is independent of the product formed in any other reaction chamber, but is generated using one or more common reagents. The starting material can be a nucleic acid sequence and at least one reagent in the fluid is a nucleotide or nucleotide analog. The fluid can additionally have a polymerase capable of reacting the nucleic acid sequence and the nucleotide or nucleotide analog. The steps of the method can be repeated sequentially.

The apparatus includes a novel reagent delivery cuvette adapted for use with the arrays described herein, to provide fluid reagents to the array, and a reagent delivery means in communication with the reagent delivery cuvette. The invention includes a cuvette for monitoring light emission in an array of reaction chambers, where the cuvette comprises: a detection chamber adapted to accept an array having a top surface with multiple reaction chambers disposed thereon; at least one surface or opening to allow transmission of the light emission; a receptacle adapted to align the array with an optical detector; and affluent and effluent outlets to allow the array to be in fluid communication with one or more reagent reservoirs.

The disclosures of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art The examples of embodiments are for illustration purposes only. All patents and publications cited in this specification are incorporated by reference.

BRIEF DESCRIPTION OF THE DRAWINGS

FIGS. 1A-D are schematic illustrations of rolling circle-based amplification using an anchor primer.

DETAILED DESCRIPTION OF THE INVENTION

Figure 1A:
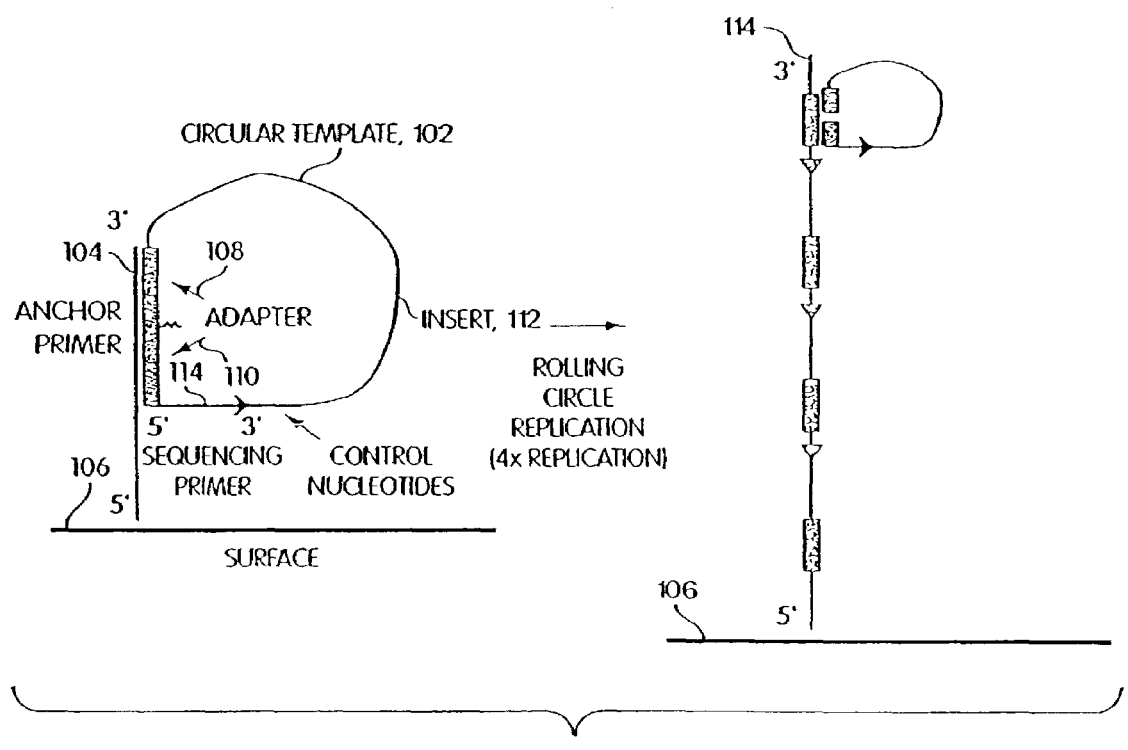

The methods and apparatuses described herein allow for the determination of nucleic acid sequence information without the need for first cloning a nucleic acid. In addition, the method is highly sensitive and can be used to determine the nucleotide sequence of a template nucleic acid, which is present in only a few copies in a starting population of nucleic acids. Further, the method can be used to determine simultaneously the sequences of a large number of nucleic acids.

The methods and apparatuses described are generally useful for any application in which the identification of any particular nucleic acid sequence is desired. For example, the methods allow for identification of single nucleotide polymorphisms (SNPs), haplotypes involving multiple SNPs or other polymorphisms on a single chromosome, and transcript profiling. Other uses include sequencing of artificial DNA constructs to confirm or elicit their primary sequence, or to identify specific mutant clones from random mutagenesis screens, as well as to obtain the sequence of cDNA from single cells, whole tissues or organisms from any developmental stage or environmental circumstance in order to determine the gene expression profile from that specimen. In addition, the methods allow for the sequencing of PCR products and/or cloned DNA fragments of any size isolated from any source.

The methods described herein include a sample preparation process that results in a solid or a mobile solid substrate array containing a plurality of anchor primers covalently linked to a nucleic acid containing one or more copies complementary to a target nucleic acid. Formation of the covalently linked anchor primer and one or more copies of the target nucleic acid preferably occurs by annealing the anchor primer to a complementary region of a circular nucleic acid, and then extending the annealed anchor primer with a polymerase to result in formation of a nucleic acid containing one or more copies of a sequence complementary to the circular nucleic acid.

Attachment of the anchor primer to a solid or mobile solid substrate can occur before during, or subsequent to extension of the annealed anchor primer. Thus, in one embodiment, one or more anchor primers are linked to the solid or a mobile solid substrate, after which the anchor primer is annealed to a target nucleic acid and extended in the presence of a polymerase. Alternatively, in a second embodiment, an anchor primer is first annealed to a target nucleic acid, and a 3' OH terminus of the annealed anchor primer is extended with a polymerase. The extended anchor primer is then linked to the solid or mobile solid substrate. By varying the sequence of anchor primers, it is possible to specifically amplify distinct target nucleic acids present in a population of nucleic acids.

Sequences in the target nucleic acid can be identified in a number of ways. Preferably, a sequencing primer is annealed to the amplified nucleic acid and used to generate a sequencing product. The nucleotide sequence of the sequence product is then determined, thereby allowing for the determination of the nucleic acid. Similarly, in one embodiment, the template nucleic acid is amplified prior to its attachment to the bead or other mobile solid support. In other embodiments, the template nucleic acid is attached to the bead prior to its amplification.

The methods of the present invention can be also used for the sequencing of DNA fragments generated by analytical techniques that probe higher order DNA structure by their differential sensitivity to enzymes, radiation or chemical treatment (e.g., partial DNase treatment of chromatin), or for the determination of the methylation status of DNA by comparing sequence generated from a given tissue with or without prior treatment with chemicals that convert methylcytosine to thymidine (or other nucleotide) as the effective base recognized by the polymerase. Further, the methods of the present invention can be used to assay cellular physiology changes occurring during development or senescence at the level of primary sequence.

The invention also provides methods of preparing nucleic acid sequences for subsequent analysis, e.g., sequencing.

I. Apparatus for Sequencing Nucleic Acids

This invention provides an apparatus for sequencing nucleic acids, which generally comprises one or more reaction chambers for conducting a sequencing reaction, means for delivering reactants to and from the reaction chamber(s), and means for detecting a sequencing reaction event. In another embodiment, the apparatus includes a reagent delivery cuvette containing a plurality of cavities on a planar surface. In a preferred embodiment, the apparatus is connected to at least one computer for controlling the individual components of the apparatus and for storing and/or analyzing the information obtained from detection of the sequence reaction event.

The invention also provides one or more reaction chambers are arranged in the form of an array on an inert substrate material, also referred to herein as a "solid support", that allows for combination of the reactants in a sequencing reaction in a defined space and for detection of the sequencing reaction event. Thus, as used herein, the terms "reaction chamber" or "analyte reaction chamber" refer to a localized area on the substrate material that facilitates interaction of reactants, e.g., in a nucleic acid sequencing reaction. As discussed more fully below, the sequencing reactions contemplated by the invention preferably occur on numerous individual nucleic acid samples in tandem, in particular simultaneously sequencing numerous nucleic acid samples derived from genomic and chromosomal DNA. The apparatus of the invention therefore preferably comprises an array having a sufficient number of reaction chambers to carry out such numerous individual sequencing reactions. In one embodiment, the array comprises at least 1,000 reaction chambers. In another embodiment, the array comprises greater than 400,000 reaction chambers, preferably between 400,000 and 20,000,000 reaction chambers. In a more preferred embodiment, the array comprises between 1,000,000 and 16,000,000 reaction chambers.

The reaction chambers on the array typically take the form of a cavity or well in the substrate material, having a width and depth, into which reactants can be deposited. One or more of the reactants typically are bound to the substrate material in the reaction chamber and the remainder of the reactants are in a medium which facilitates the reaction and which flows through the reaction chamber. When formed as cavities or wells, the chambers are preferably of sufficient dimension and order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In another embodiment, the shape of the well or cavity is substantially hexagonal. The cavity can have a smooth wall surface. In an additional embodiment, the cavity can have at least one irregular wall surface. The cavities can have a planar bottom or a concave bottom. The reaction chambers can be spaced between 5 μm and 200 μm apart. Spacing is determined by measuring the center-to-center distance between two adjacent reaction chambers. Typically, the reaction chambers can be spaced between 10 μm and 150 μm apart, preferably between 50 μm and 100 μm apart. In one embodiment, the reaction chambers have a width in one dimension of between 0.3 μm and 100 μm. The reaction chambers can have a width in one dimension of between 0.3 μm and 20 μm, preferably between 0.3 μm and 10 μm, and most preferably about 6 μm. In another embodiment, the reaction chambers have a width of between 20 μm and 70 μm. Ultimately the width of the chamber may be dependant on whether the nucleic acid samples require amplification. If no amplification is necessary, then smaller, e.g., 0.3 μm is preferred. If amplification is necessary, then larger, e.g., 6 μm is preferred. The depth of the reaction chambers are preferably between 10 μm and 100 μm. Alternatively, the reaction chambers may have a depth that is between 0.25 and 5 times the width in one dimension of the reaction chamber or, in another embodiment, between 0.3 and 1 times the width in one dimension of the reaction chamber.

In another aspect, the invention involves an apparatus for determining the nucleic acid sequence in a template nucleic acid polymer. The apparatus includes an array having a plurality of cavities on a planar surface. Each cavity forms an analyte reaction chamber, wherein the reaction chambers have a center-to-center spacing of between 5 to 200 μm. It also includes a nucleic acid delivery means for introducing a template nucleic acid polymers into the reaction chambers; and a nucleic acid delivery means to deliver reagents to the reaction chambers to create a polymerization environment in which the nucleic acid polymers will act as a template polymers for the synthesis of complementary nucleic acid polymers when nucleotides are added. The apparatus also includes a reagent delivery means for successively providing to the polymerization environment a series of feedstocks, each feedstock comprising a nucleotide selected from among the nucleotides from which the complementary nucleic acid polymer will be formed, such that if the nucleotide in the feedstock is complementary to the next nucleotide in the template polymer to be sequenced the nucleotide will be incorporated into the complementary polymer and inorganic pyrophosphate will be released. It also includes a detection means for detecting the formation of inorganic pyrophosphate enzymatically; and a data processing means to determine the identity of each nucleotide in the complementary polymers and thus the sequence of the template polymers In another aspect, the invention involves an apparatus for determining the base sequence of a plurality of nucleotides on an array. The apparatus includes a reagent cuvette containing a plurality of cavities on a planar surface. Each cavity forms an analyte reaction chamber, wherein the reaction chambers have a center-to-center spacing of between 5 to 200 µm. The apparatus also includes a reagent delivery means for adding an activated nucleotide 5'-triphosphate precursor of one known nitrogenous base to a reaction mixture in each reaction chamber. Each reaction mixture has a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates. The apparatus also includes a detection means for detecting whether or not the nucleoside 5'-triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triphosphate precursor. The apparatus also includes a means for sequentially repeating the second and third steps wherein each sequential repetition adds and, detects the incorporation of one type of activated nucleoside 5'-triphosphate precursor of known nitrogenous base composition. The apparatus also includes a data processing means for determining the base sequence of the unpaired nucleotide residues of the template in each reaction chamber from the sequence of incorporation of the nucleoside precursors Solid Support Material Any material can be used as the solid support material, as long as the surface allows for stable attachment of the primers and detection of nucleic acid sequences. The solid support material can be planar or can be cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In some embodiments, the solid support is optically transparent, e.g., glass.

An array of attachment sites on an optically transparent solid support can be constructed using lithographic techniques commonly used in the construction of electronic integrated circuits as described in, e.g., techniques for attachment described in U.S. Pat. Nos. 5,143,854, 5,445,934, 5,744,305, and 5,800,992; Chee et al., Science 274: 610-614 (1996); Fodor et al., Nature 364: 555-556 (1993); Fodor et al., Science 251: 767-773 (1991); Gushin, et al., Anal. Biochem. 250: 203-211 (1997); Kinosita et al., Cell 93: 21-24 (1998); Kato-Yamada et al., J. Biol. Chem. 273: 19375-19377 (1998); and Yasuda et al., Cell 93: 1117-1124 (1998). Photolithography and electron beam lithography sensitize the solid support or substrate with a linking group that allows attachment of a modified biomolecule (e.g., proteins or nucleic acids). See e.g., Service, Science 283: 27-28 (1999); Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997). Alternatively, an array of sensitized sites can be generated using thin-film technology as described in Zasadzinski et al., Science 263: 1726-1733 (1994).

Fiber Optic Substrate Arrays

The substrate material is preferably made of a material that facilitates detection of the reaction event. For example, in a typical sequencing reaction, binding of a dNTP to a sample nucleic acid to be sequenced can be monitored by detection of photons generated by enzyme action on phosphate liberated in the sequencing reaction. Thus, having the substrate material made of a transparent or optically (i.e., light) conductive material facilitates detection of the photons.

In some embodiments, the solid support can be coupled to a bundle of optical fibers that are used to detect and transmit the light product. The total number of optical fibers within the bundle may be varied so as to match the number of individual reaction chambers in the array utilized in the sequencing reaction. The number of optical fibers incorporated into the bundle is designed to match the resolution of a detection device so as to allow 1:1 imaging. The overall sizes of the bundles are chosen so as to optimize the usable area of the detection device while maintaining desirable reagent (flow) characteristics in the reaction chamber. Thus, for a 4096×4096 pixel CCD (charge-coupled device) array with 15 µm pixels, the fiber bundle is chosen to be approximately 60 mm×60 mm or to have a diameter of approximately 90 mm. The desired number of optical fibers are initially fused into a bundle or optical fiber array, the terminus of which can then be cut and polished so as to form a "wafer" of the required thickness (e.g. 1.5 mm). The resulting optical fiber wafers possess similar handling properties to that of a plane of glass. The individual fibers can be any size diameter (e.g., 3 µm to 100 µm).

In some embodiments two fiber optic bundles are used: a first bundle is attached directly to the detection device (also referred to herein as the fiber bundle or connector) and a second bundle is used as the reaction chamber substrate (the wafer or substrate). In this case the two are placed in direct contact, optionally with the use of optical coupling fluid, in order to image the reaction centers onto the detection device. If a CCD is used as the detection device, the wafer could be slightly larger in order to maximize the use of the CCD area, or slightly smaller in order to match the format of a typical microscope slide—25 mm×75 mm. The diameters of the individual fibers within the bundles are chosen so as to maximize the probability that a single reaction will be imaged onto a single pixel in the detection device, within the constraints of the state of the art. Exemplary diameters are 6-8 µm for the fiber bundle and 6-50 µm for the wafer, though any diameter in the range 3-100 µm can be used. Fiber bundles can be obtained commercially from CCD camera manufacturers. In these arrays, typically the distance between the top surface and the bottom surface is no greater than 10 cm, preferably no greater than 3 cm, most preferably no greater than 2 cm, and usually between 0.5 mm to 5 mm. For example, the wafer can be obtained from Incom, Inc. (Chariton, Mass.) and cut and polished from a large fusion of fiber optics, typically being 2 mm thick, though possibly being 0.5 to 5 mm thick. The wafer has handling properties similar to a pane of glass or a glass microscope slide.

Reaction chambers can be formed in the substrate made from fiber optic material. The surface of the optical fiber is cavitated by treating the termini of a bundle of fibers, e.g., with acid, to form an indentation in the fiber optic material. Thus, in one embodiment cavities are formed from a fiber optic bundle, preferably cavities can be formed by etching one end of the fiber optic bundle. Each cavitated surface can form a reaction chamber. Such arrays are referred to herein as fiber optic reactor arrays or FORA. The indentation ranges in depth from approximately one-half the diameter of all individual optical fiber tip to two to three times the diameter of the fiber. Cavities can be introduced into the termini of the fibers by placing one side of the optical fiber wafer into an acid bath for a variable amount of time. The amount of time can vary depending upon the overall depth of the reaction cavity desired (see e.g., Walt, et al, 1996. *Anal. Chem.* 70: 1888). A wide channel cavity can have uniform flow velocity dimensions of approximately 14 mm×43 mm. Thus, with this approximate dimension and at approximately $4.82 \times 10^{-4}$ cavities/um$^2$ density, the apparatus can have approximately 290,000 fluidically accessible cavities. Several methods are known in the art for attaching molecules (and detecting the attached molecules) in the cavities etched in the ends of fiber optic bundles. See, e.g., Michael, et al., *Anal. Chem.* 70: 1242-1248 (1998); Ferguson, et al., *Nature Biotechnology* 14: 1681-1684 (1996); Healey and Walt, *Anal. Chem.* 69: 2213-2216 (1997). A pattern of reactive sites can also be created in the microwell, using photolithographic techniques similar to those used in the generation of a pattern of reaction pads on a planar support. See, Healey, et al., *Science* 269: 1078-1080 (1995); Munkholm and Walt, *Anal. Chem.* 58: 1427-1430 (1986), and Bronk, et al., *Anal. Chem.* 67: 2750-2757 (1995).

The opposing side of the optical fiber wafer (i.e., the non-etched side) is typically highly polished so as to allow optical-coupling (e.g., by immersion oil or other optical coupling fluids) to a second, optical fiber bundle. This second optical fiber bundle exactly matches the diameter of the optical wafer containing the reaction chambers, and serve to act as a conduit for the transmission of light product to the attached detection device, such as a CCD imaging system or camera.

In one preferred embodiment, the fiber optic wafer is thoroughly cleaned, e.g. by serial washes in 15% $H_2O_2$/15% $NH_4OH$ volume:volume in aqueous solution, then six deionized water rinses, then 0.5M EDTA, then six deionized water, then 15% $H_2O_2$/15% $NH_4OH$, then six deionized water (one-half hour incubations in each wash).

The surface of the fiber optic wafer is preferably coated to facilitate its use in the sequencing reactions. A coated surface is preferably optically transparent, allows for easy attachment of proteins and nucleic acids, and does not negatively affect the activity of immobilized proteins. In addition, the surface preferably minimizes non-specific absorption of macromolecules and increases the stability of linked macromolecules (e.g., attached nucleic acids and proteins).

Suitable materials for coating the array include, e.g., plastic (e.g. polystyrene). The plastic can be preferably spin-coated or sputtered (0.1 µm thickness). Other materials for coating the array include gold layers, e.g. 24 karat gold. 0.1 µm thickness, with adsorbed self assembling monolayers of long chain thiol alkanes. Biotin is then coupled covalently to the surface and saturated with a biotin-binding protein (e.g. streptavidin or avidin).

Coating materials can additionally include those systems used to attach an anchor primer to a substrate. Organosilane reagents, which allow for direct covalent coupling of proteins via amino, sulfhydryl or carboxyl groups, can also be used to coat the array. Additional coating substances include photoreactive linkers, e.g. photobiotin, (Amos et al., "Biomaterial Surface Modification Using Photochemical Coupling Technology," in Encyclopedic Handbook of Biomaterials and Bioengineering, Part A: Materials, Wise et al. (eds.), New York, Marcel Dekker, pp. 895926, 1995).

Additional coating materials include hydrophilic polymer gels (polyacrylamide, polysaccharides), which preferably polymerize directly on the surface or polymer chains covalently attached post polymerization (Hjerten, *J. Chromatogr.* 347,191 (1985); Novotny, *Anal. Chem.* 62,2478 (1990), as well as pluronic polymers (triblock copolymers, e.g. PPO-PEO-PPO, also known as F-108), specifically adsorbed to either polystyrene or silanized glass surfaces (Ho et al., *Langmuir* 14:3889-94, 1998), as well as passively adsorbed layers of biotin-binding proteins. The surface can also be coated with an epoxide which allows the coupling of reagents via an amine linkage.

In addition, any of the above materials can be derivatized with one or more functional groups, commonly known in the art for the immobilization of enzymes and nucleotides, e.g. metal chelating groups (e.g. nitrilo triacetic acid, iminodiacetic acid, pentadentate chelator), which will bind 6×His-tagged proteins and nucleic acids.

Surface coatings can be used that increase the number of available binding sites for subsequent treatments, e.g. attachment of enzymes (discussed later), beyond the theoretical binding capacity of a 2D surface.

In a preferred embodiment, the individual optical fibers utilized to generate the fused optical fiber bundle/wafer are larger in diameter (i.e., 6 µm to 12 µm) than those utilized in the optical imaging system (i e., 3 µm). Thus, several of the optical imaging fibers can be utilized to image a single reaction site.

Summary of the Arrays of this Invention

In one aspect, the invention involves an array including a planar surface with a plurality of reaction chambers disposed thereon, wherein the reaction chambers have a center to center spacing of between 5 to 200 µm and each chamber has a width in at least one dimension of between 0.3 µm and 100 µm. In some embodiments, the array is a planar surface with a plurality of cavities thereon, where each cavity forms an analyte reaction chamber. In a preferred embodiment, the array is fashioned from a sliced fiber optic bundle (i.e., a bundle of fused fiber optic cables) and the reaction chambers are formed by etching one surface of the fiber optic reactor array ("FORA"). The cavities can also be formed in the substrate via etching, molding or micromachining.

Specifically, each reaction chamber in the array typically has a width in at least one dimension of between 0.3 µm and 100 µm, preferably between 0.3 µm and 20 µm, mst preferably between 0.3 µm and 10 µm. In a separate embodiment, we contemplate larger reaction chambers, preferably having a width in at least one dimension of between 20 µm and 70 µm.

The array typically contains more than 1,000 reaction chambers, preferably more than 400,000, more preferably between 400,000 and 20,000,000, and most preferably between 1,000,000 and 16,000,000 cavities or reaction chambers. The shape of each cavity is frequently substantially hexagonal, but the cavities can also be cylindrical. In some embodiments, each cavity has a smooth wall surface, however, we contemplate that each cavity may also have at least one irregular wall surface. The bottom of each of the cavities can be planar or concave.

The array is typically constructed to have cavities or reaction chambers with a center-to-center spacing between 10 to 150 µm, preferably between 50 to 100 µm.

Each cavity or reaction chamber typically has a depth of between 10 µm and 100 µm; alternatively, the depth is between 0.25 and 5 times the size of the width of the cavity, preferably between 0.3 and 1 times the size of the width of the cavity.

In one embodiment, the arrays described herein typically include a planar top surface and a planar bottom surface, which is optically conductive such that optical signals from the reaction chambers can be detected through the bottom planar surface. In these arrays, typically the distance between the top surface and the bottom surface is no greater than 10 cm, preferably no greater than 3 cm, most preferably no greater than 2 cm.

In one embodiment, each cavity of the array contains reagents for analyzing a nucleic acid or protein. The array can also include a second surface spaced apart from the planar array and in opposing contact therewith such that a flow chamber is formed over the array.

In another aspect, the invention involves an array means for carrying out separate parallel common reactions in an aqueous environment, wherein the array means includes a substrate having at least 1,000 discrete reaction chambers. These chambers contain a starting material that is capable of reacting with a reagent. Each of the reaction chambers are dimensioned such that when one or more fluids containing at least one reagent is delivered into each reaction chamber, the diffusion time for the reagent to diffuse out of the well exceeds the time required for the starting material to react with the reagent to form a product. The reaction chambers can be formed by generating a plurality of cavities on the substrate, or by generating discrete patches on a planar surface, the patches having a different surface chemistry than the surrounding planar surface.

In one embodiment, each cavity or reaction chamber of the array contains reagents for analyzing a nucleic acid or protein. Typically those reaction chambers that contain a nucleic acid (not all reaction chambers in the array are required to) contain only a single species of nucleic acid (i.e., a single sequence that is of interest). There may be a single copy of this species of nucleic acid in any particular reaction chamber, or they may be multiple copies. It is generally preferred that a reaction chamber contain at least 100 copies of a nucleic acid sequence, preferably at least 100,000 copies, and most preferably between 100,000 to 1,000,000 copies of the nucleic acid. The ordinarily skilled artisan will appreciate that changes in the number of copies of a nucleic acid species in any one reaction chamber will affect the number of photons generated in a pyrosequencing reaction, and can be routinely adjusted to provide more or less photon signal as is required.

In one embodiment the nucleic acid species is amplified to provide the desired number of copies using PCR, RCA, ligase chain reaction, other isothermal amplification, or other conventional means of nucleic acid amplification. In one embodimant, the nucleic acid is single stranded. In other embodiments the single stranded DNA is a concatamer with each copy covalently linked end to end.

Delivery Means

Figure 3:
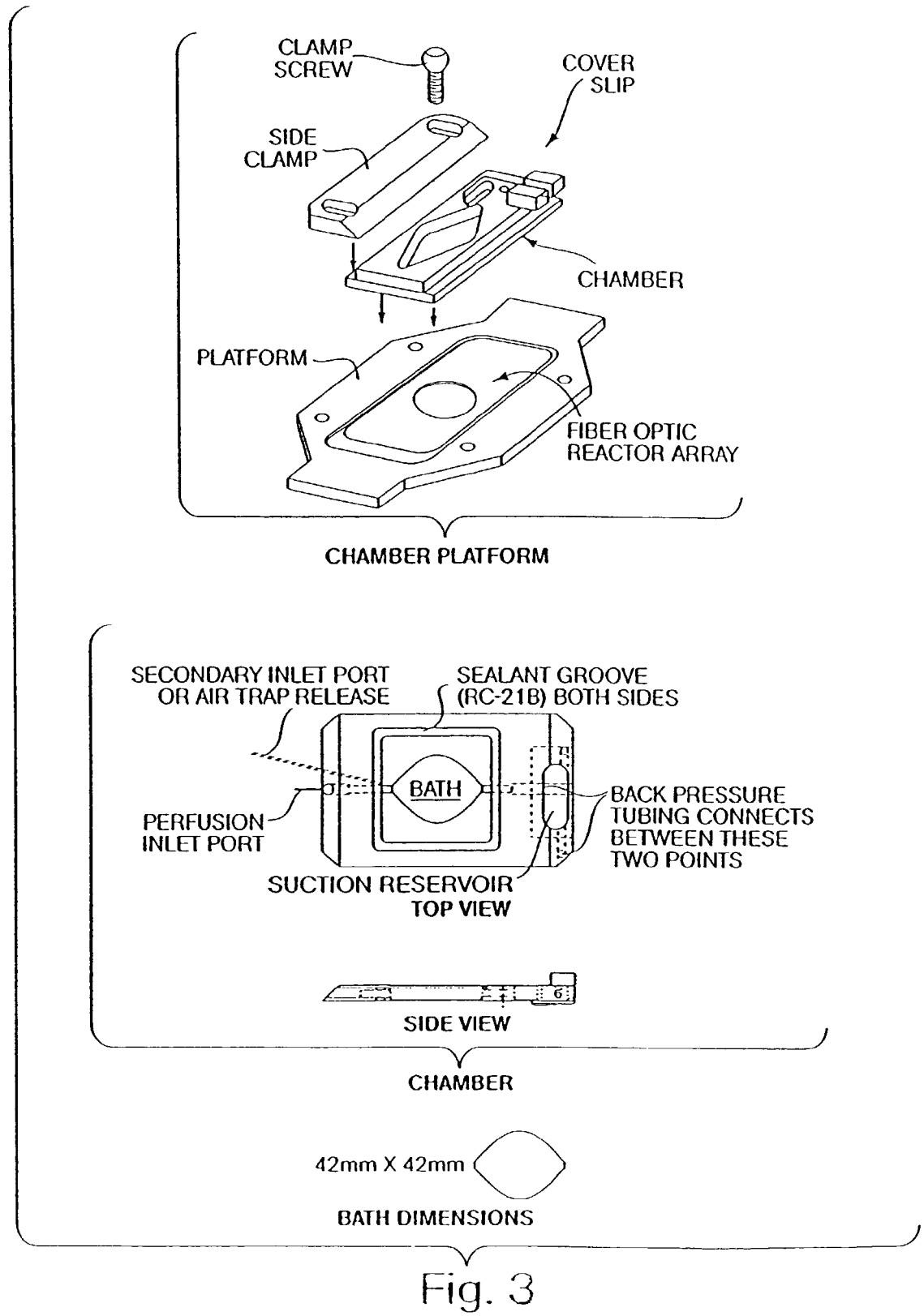
FIG. 3 is a drawing of a perfusion chamber according to the present invention.
Figure 4:
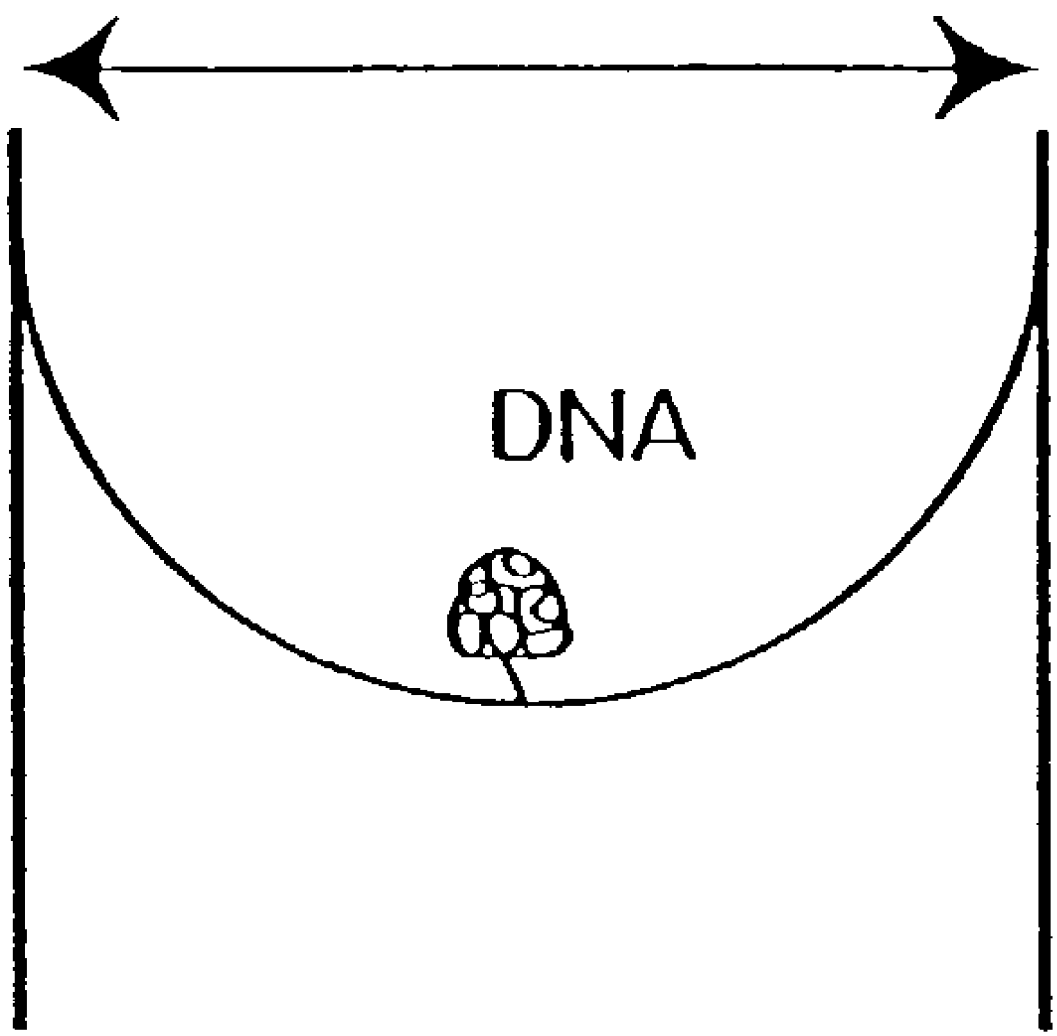
FIG. 4 is a drawing of a cavitated fiber optic terminus of the present invention.

An example of the means for delivering reactants to the reaction chamber is the perfusion chamber of the present invention is illustrated in FIG. 3. The perfusion chamber includes a sealed compartment with transparent tipper and lower slide. It is designed to allow flow of solution over the surface of the substrate surface and to allow for fast exchange of reagents. Thus, it is suitable for carrying out, for example, the pyrophosphate sequencing reactions. The shape and dimensions of the chamber can be adjusted to optimize reagent exchange to include bulk flow exchange, diffusive exchange, or both in either a laminar flow or a turbulent flow regime.

The correct exchange of reactants to the reaction chamber is important for accurate measurements in the present invention. In the absence of convective flow of bulk fluid, transport of reaction participants (and cross-contamination or "cross-talk" between adjacent reaction sites or microvessels) can take place only by diffusion. If the reaction site is considered to be a point source on a 2-D surface, the chemical species of interest (e.g., a reaction product) will diffuse radially from the site of its production, creating a substantially hemispherical concentration field above the surface.

The distance that a chemical entity can diffuse in any given time t may be estimated in a crude manner by considering the mathematics of diffusion (Crank, *The Mathematics of Diffusion*, $2^{nd}$ ed. 1975). The rate of diffusive transport in any given direction x(cm) is given by Fick's law as $$j = -D\frac{\partial C}{\partial x} \qquad \text{Eq. 1}$$

where j is the flux per unit area (g-mol/cm$^2$-s) of a species with diffusion coefficient D (cm$^2$/s), and $\partial C/\partial x$ is the concentration gradient of that species. The mathematics of diffusion are such that a characteristic or "average" distance an entity can travel by diffusion alone scales with the one-half power of both the diffusion coefficient and the time allowed for diffusion to occur. Indeed, to order of magnitude, this characteristic diffusion distance can be estimated as the square root of the product of the diffusion coefficient and time—as adjusted by a numerical factor of order unity that takes into account the particulars of the system geometry and initial and/or boundary conditions imposed on the diffusion process.

It will be convenient to estimate this characteristic diffusion distance as the root-mean-square distance $d_{rms}$ that a diffusing entity can travel in time t:

$$d_{rms} = \sqrt{2Dt} \qquad \text{Eq. 2}$$

As stated above, the distance that a diffusing chemical typically travels varies with the square root of the time available for it to diffuse—and inversely, the time required for a diffusing chemical to travel a given distance scales with the square of the distance to be traversed by diffusion. Thus, for a simple, low-molecular-weight biomolecule characterized by a diffusion coefficient D of order $1 \cdot 10^{-5}$ cm$^2$/s, the root-mean-square diffusion distances $d_{rms}$ that can be traversed in time intervals of 0.1 s. 1.0 s, 2.0 s, and 10 s are estimated by means of Equation 2 as 14 µm, 45 µm, 63 µm, and 141 µm, respectively.

The relative importance of convection and diffusion in a transport process that involves both mechanisms occurring simultaneously can be gauged with the aid of a dimensionless number—namely, the Peclet number Pe. This Peclet number can be viewed as a ratio of two rates or velocities—namely, the rate of a convective flow divided by the rate of a diffusive "flow" or flux. More particularly, the Peclet number is a ratio of a characteristic flow velocity V(in cm/s) divided by a characteristic diffusion velocity D/L (also expressed in units of cm/s)—both taken in the same direction:

$$Pe = \frac{VL}{D} \qquad \text{Eq. 3}$$

In Equation 3, V is the average or characteristic speed of the convective flow, generally determined by dividing the volumetric flow rate Q (in cm$^3$/s) by the cross-sectional area A (cm$^2$) available for flow. The characteristic length L is a representative distance or system dimension measured in a direction parallel to the directions of flow and of diffusion (i.e., in the direction of the steepest concentration gradient) and selected to be representative of the typical or "average" distance over which diffusion occurs in the process. And finally D (cm$^2$/s) is the diffusion coefficient for the diffusing species in question. (An alternative but equivalent formulation of the Peclet number Pe views it as the ratio of two characteristic times—namely, of representative times for diffusion and convection. Equation 3 for the Peclet number can equally well be obtained by dividing the characteristic diffusion time $L^2/D$ by the characteristic convection time L/V.)

The convective component of transport can be expected to dominate over the diffusive component in situations where the Peclet number Pe is large compared to unity. Conversely, the diffusive component of transport can be expected to dominate over the convective component in situations where the Peclet number Pe is small compared to unity. In extreme situations where the Peclet number is either very much larger or very much smaller than one, transport may be accurately presumed to occur either by convection or by diffusion alone, respectively. Finally, in situations where the estimated Peclet number is of order unity, then both convection and diffusion can be expected to play significant roles in the overall transport process.

The diffusion coefficient of a typical low-molecular-weight biomolecule will generally be of the order of $10^{-5}$ cm$^2$/s (e.g., $0.52 \cdot 10^{-5}$ cm/s for sucrose, and $1.06 \cdot 10^{-5}$ cm/s for glycine). Thus, for reaction centers, cavities, or wells separated by a distance of 100 µm (i.e., 0.01 cm), the Peclet number Pe for low-molecular-weight solutes such as these will exceed unity for flow velocities greater than about 10 µm/sec (0.001 cm/s). For cavities separated by only 10 µm (i.e., 0.001 cm), the Peclet number Pe for low-molecular-weight solutes will exceed unity for flow velocities greater than about 100 µm/sec (0.01 cm/s). Convective transport is thus seen to dominate over diffusive transport for all but very slow flow rates and/or very short diffusion distances.

Where the molecular weight of a diffusible species is substantially larger—for example as it is with large biomolecules like DNA/RNA, DNA fragments, oligonucleotides, proteins, and constructs of the former—then the species diffusivity will be correspondingly smaller, and convection will play an even more important role relative to diffusion in a transport process involving both mechanisms. For instance, the aqueous-phase diffusion coefficients of proteins fall in about a 10-fold range (Tanford, *Physical Chemistry of Macromolecules*, 1961). Protein diffusivities are bracketed by values of $1.19 \times 10^{-6}$ cm$^2$/s for ribonuclease (a small protein with a molecular weight of 13.683 Daltons) and $1.16 \times 10^{-7}$ cm$^2$/s for myosin (a large protein with a molecular weight of 493,000 Daltons). Still larger entities (e.g., tobacco mosaic virus or TMV at 40.6 million Daltons) are characterized by still lower diffusivities (in particular, $4.6 \times 10^{-8}$ cm$^2$/s for TMV) (Lehninger, *Biochemistry*, 2$^{nd}$ ed. 1975). The fluid velocity at which convection and diffusion contribute roughly equally to transport (i.e., Pe of order unity) scales in direct proportion to species diffusivity.

With the aid of the Peclet number formalism it is possible to gauge the impact of convection on reactant supply to—and product removal from—reaction chambers, cavities or wells. On the one hand, it is clear that even modest convective flows can appreciably increase the speed at which reactants are delivered to the interior of the cavities in an array or FORA. In particular, suppose for the sake of simplicity that the criteria for roughly equal convective and diffusive flows is considered to be Pe=1. One may then estimate that a convective flow velocity of the order of only 0.004 cm/s will suffice to carry reactant into a 25-µm-deep well it roughly the same rate as it could be supplied to the bottom of the well by diffusion alone, given an assumed value for reactant diffusivity of $1 \times 10^{-5}$ cm$^2$/s. The corresponding flow velocity required to match the rate of diffusion of such a species from the bottom to the top of a 2.5-µm-deep microwell is estimated to be of order 0.04 cm/s. Flow velocities through a FORA much higher than this are possible, thereby illustrating the degree to which a modest convective flow can augment the diffusive supply of reactants to FORA reaction centers, cavities or wells.

The perfusion chamber is preferably detached from the imaging system while it is being prepared and only placed on the imaging system when sequencing analysis is performed. In one embodiment, the solid support (i.e., a DNA chip or glass slide) is held in place by a metal or plastic housing, which may be assembled and disassembled to allow replacement of said solid support. The lower side of the solid support of the perfusion chamber carries the reaction chamber array and, with a traditional optical-based focal system, a high numerical aperture objective lens is used to focus the image of the reaction center array onto the CCD imaging system.

An alternative system for the analysis is to use an array format wherein samples are distributed over a surface, for example a microfabricated chip, and thereby an ordered set of samples may be immobilized in a 2-dimensional format. Many samples can thereby be analyzed in parallel. Using the method of the invention, many immobilized templates may be analyzed in this was by allowing the solution containing the enzymes and one nucleotide to flow over the surface and then detecting the signal produced for each sample. This procedure can then be repeated. Alternatively, several different oligonucleotides complementary to the template may be distributed over the surface followed by hybridization of the template. Incorporation of deoxynucleotides or dideoxynucleotides may be monitored for each oligonucleotide by the signal produced using the various oligonucleotides as primer. By combining the signals from different areas of the surface, sequence-based analyses may be performed by four cycles of polymerase reactions using the various dideoxynucleotides.

When the support is in the form of a cavitated array, e.g., in the termini of a FORA or other array of microwells, suitable delivery means for reagents include flowing and washing and also, e.g., flowing, spraying, electrospraying, ink jet delivery, stamping, ultrasonic atomization (Sonotek Corp., Milton, N.Y.) and rolling. Preferably, all reagent solutions contain 10-20% ethylene glycol to minimize evaporation. When spraying is used, reagents are delivered to the FORA surface in a homogeneous thin layer produced by industrial type spraying nozzles (Spraying Systems. Co, Wheaton, Ill.) or atomizers used in thin layer chromatography (TLC), such as CAMAG TLC Sprayer (Camag Scientific Inc., Wilmington, N.C.). These sprayers atomize reagents into aerosol spray particles in the size range of 0.3 to 10 µm.

Electrospray deposition (ESD) of protein and DNA solutions is currently used to generate ions for mass spectrometric analysis of these molecules. Deposition of charged electrospray products on certain areas of a FORA substrate under control of electrostatic forces is suggested. It was also demonstrated that the ES-deposited proteins and DNA retain their ability to specifically bind antibodies and matching DNA probes, respectively, enabling use of the ESD fabricated matrixes in Dot Immuno-Binding (DIB) and in DNA hybridization assays. (Morozov and Morozova *Anal. Chem.* 71 (15):3110-7 (1999)).

Inkjet delivery is applicable to protein solutions and other biomacromolecules, as documented in the literature (e.g. Roda et al., *Biotechniques* 28(3): 492-6 (2000)). It is also commercially available e.g. from MicroFab Technologies. Inc. (Piano, Tex.).

Reagent solutions can alternatively be delivered to the FORA surface by a method similar to lithography. Rollers (stamps; hydrophilic materials should be used) would be first covered with a reagent layer in reservoirs with dampening sponges and then rolled over (pressed against) the FORA surface.

Successive reagent delivery steps are preferably separated by wash steps using techniques commonly known in the art. These washes can be performed, e.g., using the above described methods, including high-flow sprayers or by a liquid flow over the FORA or microwell array surface. The washes can occur in any time period after the starting material has reacted with the reagent to form a product in each reaction chamber but before the reagent delivered to any one reaction chamber has diffused out of that reaction chamber into any other reaction chamber. In one embodiment, any one reaction chamber is independent of the product formed in any other reaction chamber, but is generated using one or more common reagents.

Figure 2:
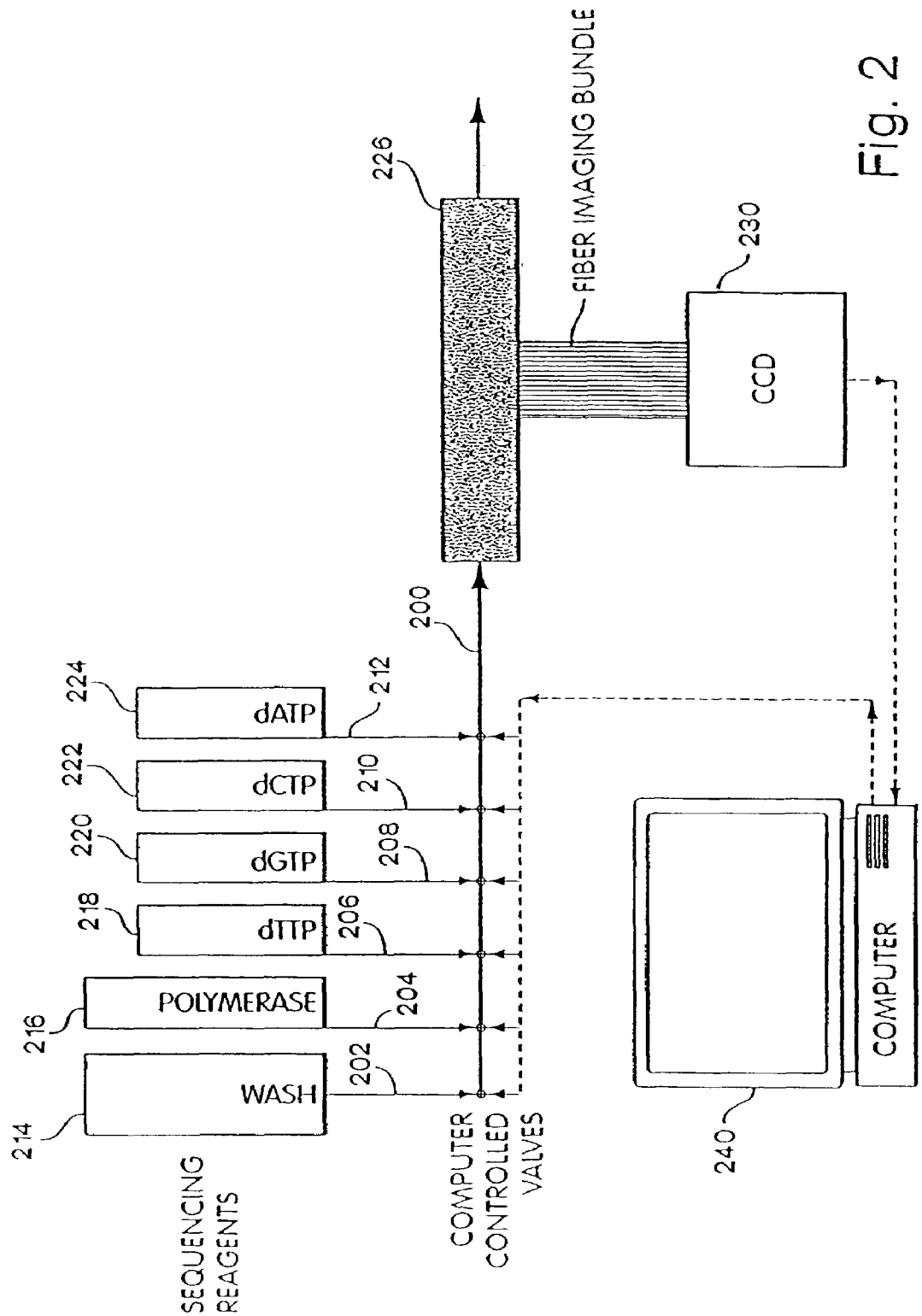
FIG. 2 is a drawing of a sequencing apparatus according to the present invention.

An embodiment of a complete apparatus is illustrated in FIG. 2. The apparatus includes an inlet conduit 200 in communication with a detachable perfusion chamber 226. The inlet conduit 200 allows for entry of sequencing reagents via a plurality of tubes 202-212, which are each in communication with a plurality of sequencing dispensing reagent vessels 214-224.

Reagents are introduced through the conduit 200 into the perfusion chamber 226 using either a pressurized system or pumps to drive positive flow. Typically, the reagent flow rates are from 0.05 to 50 ml/minute (e.g., 1 to 50 ml/minute) with volumes from 0.100 ml to continuous flow (for washing). Valves are under computer control to allow cycling of nucleotides and wash reagents. Sequencing reagents, e.g., polymerase can be either premixed with nucleotides or added in stream. A manifold brings all six tubes 202-212 together into one for feeding the perfusion chamber. Thus several reagent delivery ports allow access to the perfusion chamber. For example, one of the ports may be utilized to allow the input of the aqueous sequencing reagents, while another port allows these reagents (and any reaction products) to be withdrawn from the perfusion chamber.

The perfusion chamber 226 contains the substrate comprising the plurality of reaction chambers. The perfusion chamber allows for a uniform, linear flow of the required sequencing reagents, in aqueous solution, over the amplified nucleic acids and allows for the rapid and complete exchange of these reagents. Thus, it is suitable for performing pyrophosphate-based sequencing reactions. The perfusion chamber can also be used to prepare the anchor primers and perform amplification reactions, e.g., the RCA reactions described herein.

The invention also provides a method for delivering nucleic acid sequencing enzymes to an array. In some embodiments, one of the nucleic acid sequencing enzymes can be a polypeptide with sulfurylase activity or the nucleic acid sequencing enzyme can be a polypeptide with luciferase activity. In another embodiment, one of the nucleic acid sequencing enzymes can be a polypeptide with both sulfurylase and luciferase activity. In a more preferred embodiment, the reagent can be suitable for use in a nucleic acid sequencing reaction.

In a preferred embodiment, one or more reagents are delivered to an array immobilized or attached to a population of mobile solid supports, e.g., a bead or microsphere. The bead or microsphere need not be spherical, irregular shaped beads may be used. They are typically constructed from numerous substances, e.g., plastic, glass or ceramic and bead sizes ranging from nanometers to millimeters depending on the width of the reaction chamber. Preferably, the diameter of each mobile solid support can be between 0.01 and 0.1 times the width of each cavity. Various bead chemistries can be used e.g., methylstyrene, polystyrene, acrylic polymer, latex, paramagnetic, thoria sol, carbon graphite and titanium dioxide. The construction or chemistry of the bead can be chosen to facilitate the attachment of the desired reagent.

In another embodiment, the bioactive agents are synthesized first, and then covalently attached to the beads. As is appreciated by someone skilled in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" beads may be used that have surface chemistries that facilitate the attachment of the desired functionality by the user. Additional examples of these surface chemistries for blank beads include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155-200, incorporated here by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the candidate agent) may be derivatized using well known linkers (see Pierce catalog). For example, carbodiimides activate carboxyl groups for attack by good nucleophiles such as amines (see Torchilin et al., *Critical Rev. Thereapeutic Drug Carrier Systems*, 7(4):275-308 (1991)). Proteinaceous candidate agents may also be attached using other techniques known in the art, for example for the attachment of antibodies to polymers; see Slinkin et al., *Bioconj. Chem.* 2:342-348 (1991); Torchilin et al., supra; Trubetskoy et al., *Bioconj Chem.* 3:323-327 (1992); King et al., *Cancer Res.* 54:6176-6185 (1994); and Wilbur et al., *Bioconjugate Chem.* 5:220-235 (1994). It should be understood that the candidate agents may be attached in a variety of ways, including those listed above. Preferably, the manner of attachment does not significantly alter the functionality of the candidate agent; that is, the candidate agent should be attached in such a flexible manner as to allow its interaction with a target.

Specific techniques for immobilizing enzymes on beads are known in the prior art. In one case, $NH_2$ surface chemistry beads are used. Surface activation is achieved with a 2.5% glutaraldehyde in phosphate buffered saline (10 mM) providing a pH of 6.9 (138 mM NaCl, 2.7 mM KCl). This mixture is stirred on a stir bed for approximately 2 hours at room temperature. The beads are then rinsed with ultrapure water plus 0.01% Tween 20 (surfactant) –0.02%, and rinsed again with a pH 7.7 PBS plus 0.01% tween 20. Finally, the enzyme is added to the solution, preferably after being prefiltered using a 0.45 µm amicon micropure filter.

The population of mobile solid supports are disposed in the reaction chambers. In some embodiments, 5% to 20% of the reaction chambers can have a mobile solid support with at least one reagent immobilized thereon, 20% to 60% of the reaction chambers can have a mobile solid support with at least one reagent immobilized thereon or 50% to 100% of the reaction chambers can have a mobile solid support with at least one reagent immobilized thereon. Preferably, at least one reaction chamber has a mobile solid support having at least one reagent immobilized thereon and the reagent is suitable for use in a nucleic acid sequencing reaction.

In some embodiments, the reagent immobilized to the mobile solid support can be a polypeptide with sulfurylase activity, a polypeptide with luciferase activity or a chimeric polypeptide having both sulfurylase and luciferase activity. In one embodiment, it can be a ATP sulfurylase and luciferase fusion protein. Since the product of the sulfurylase reaction is consumed by luciferase, proximity between these two enzymes may be achieved by covalently linking the two enzymes in the form of a fusion protein. This invention would be useful not only in substrate channeling but also in reducing production costs and potentially doubling the number of binding sites on streptavidin-coated beads.

In another embodiment, the sulfurylase is a thermostable ATP sulfurylase. In a preferred embodiment, the thermostable sulfurylase is active at temperatures above ambient (to at least 50° C.). In one embodiment, the ATP sulfurylase is from a thermophile. In an additional embodiment, the mobile solid support can have a first reagent and a second reagent immobilized thereon, the first reagent is a polypeptide with sulfurylase activity and the second reagent is a polypeptide with luciferase activity.

In another embodiment, the reagent immobilized to the mobile solid support can be a nucleic acid; preferably the nucleic acid is a single stranded concatamer. In a preferred embodiment, the nucleic acid can be used for sequencing a nucleic acid, e.g., a pyrosequencing reaction.

The invention also provides a method for detecting or quantifying ATP activity using a mobile solid support; preferably the ATP can be detected or quantified as part of a nucleic acid sequencing reaction.

Figure 7:
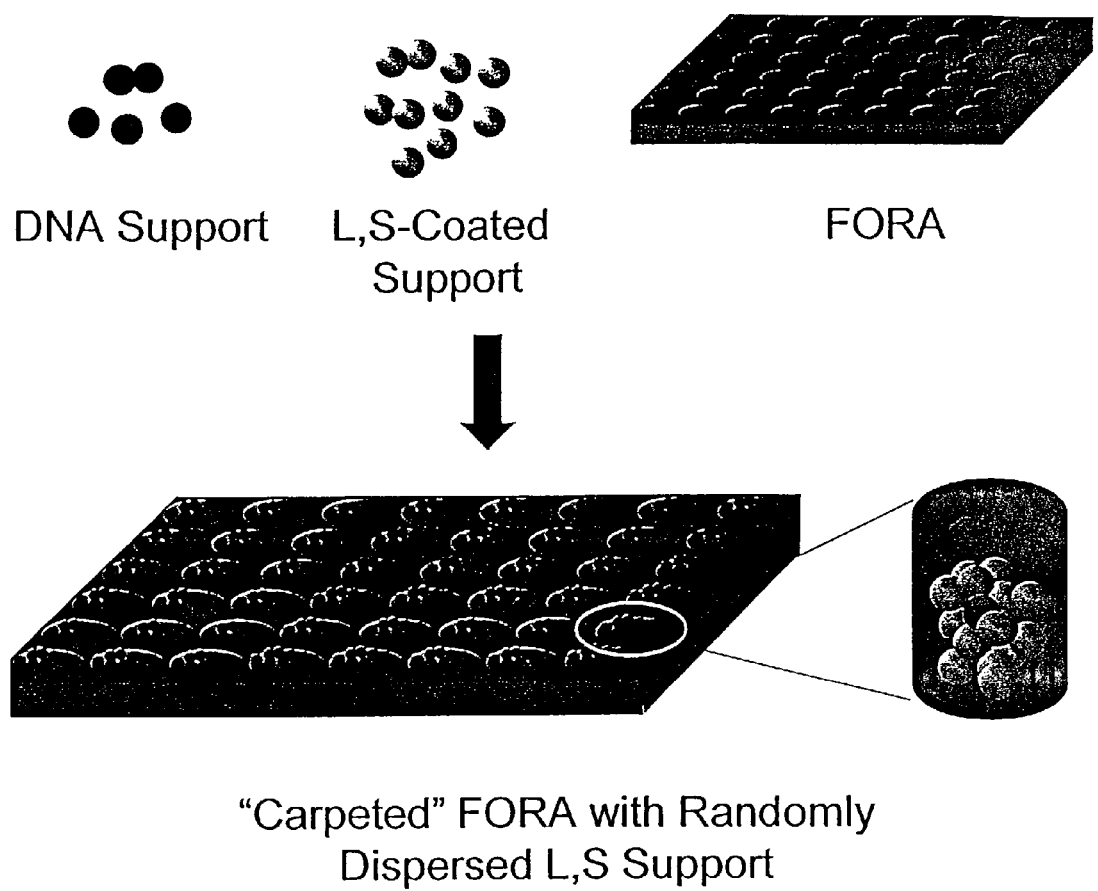
FIG. 7 is a schematic illustration for the the preparation of a carpeted FORA.
Figure 8:
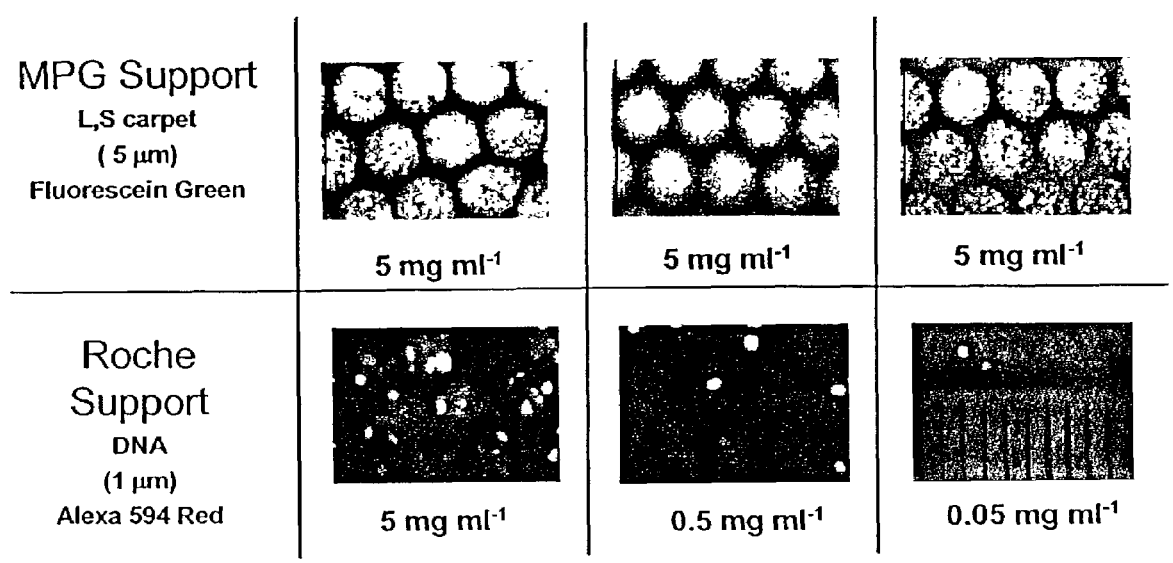
FIG. 8 is a micrograph for single well DNA delivery.
Figure 9:
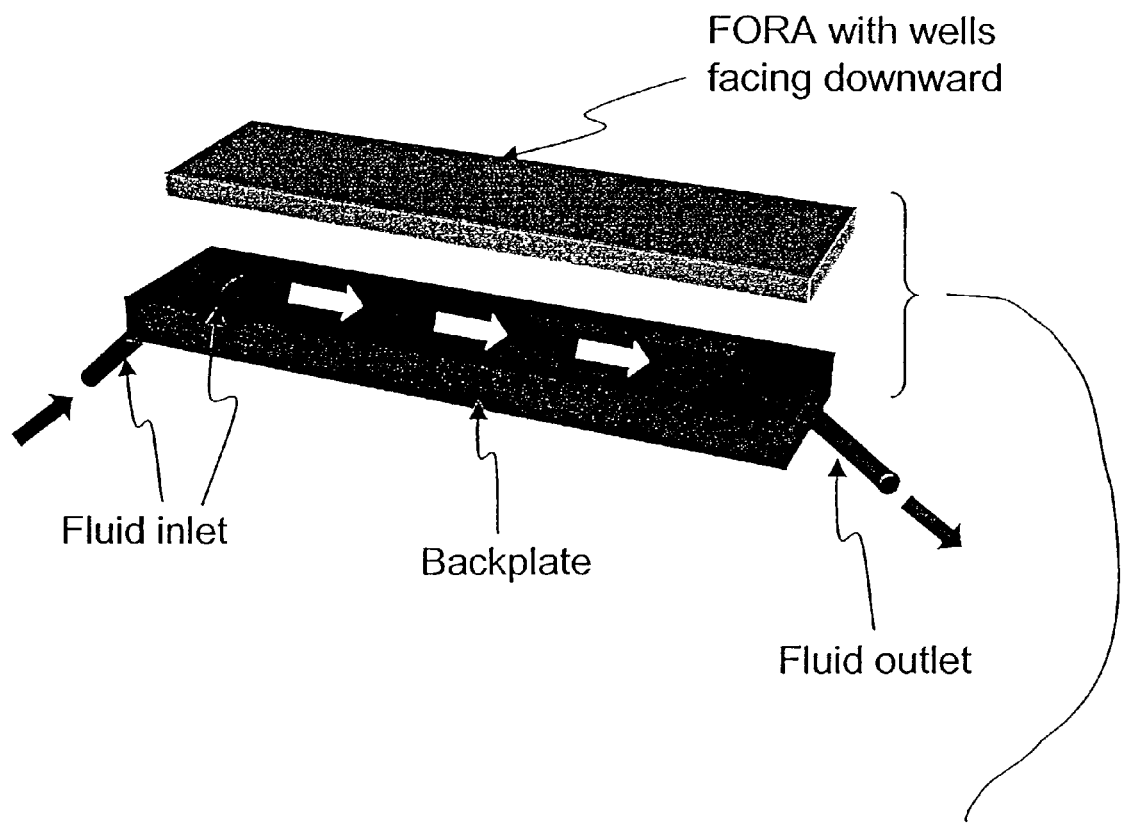
FIG. 9 is a schematic illustration of the Flow Chamber and FORA.
Figure 10:
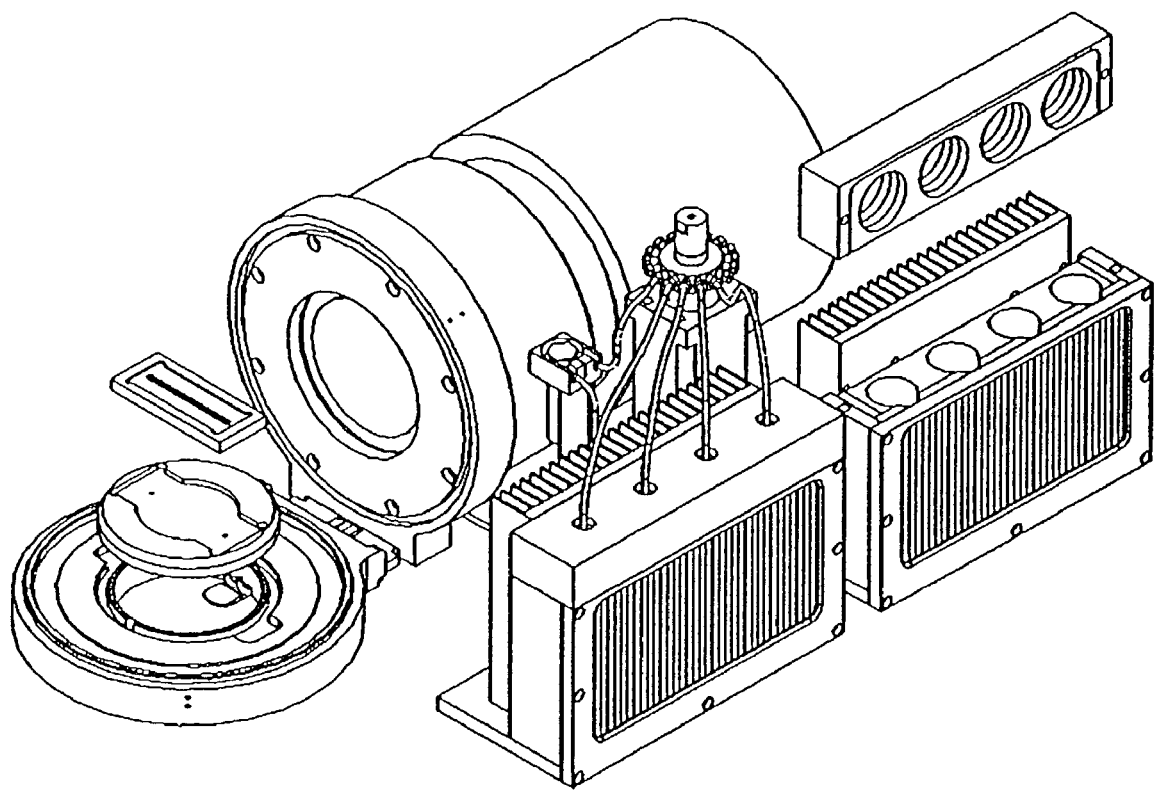
FIG. 10 is a diagram of the analytical instrument of the present invention.
Figure 11:
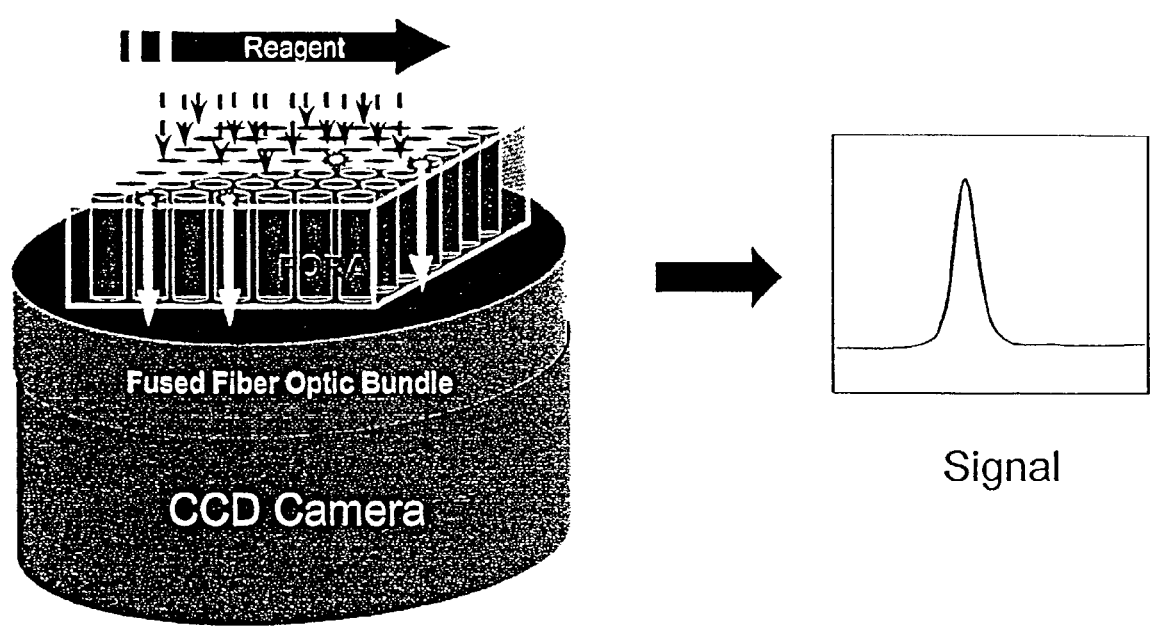
FIG. 11 is a schematic illustration of microscopic parallel sequencing reactions within a FORA.
Figure 12:
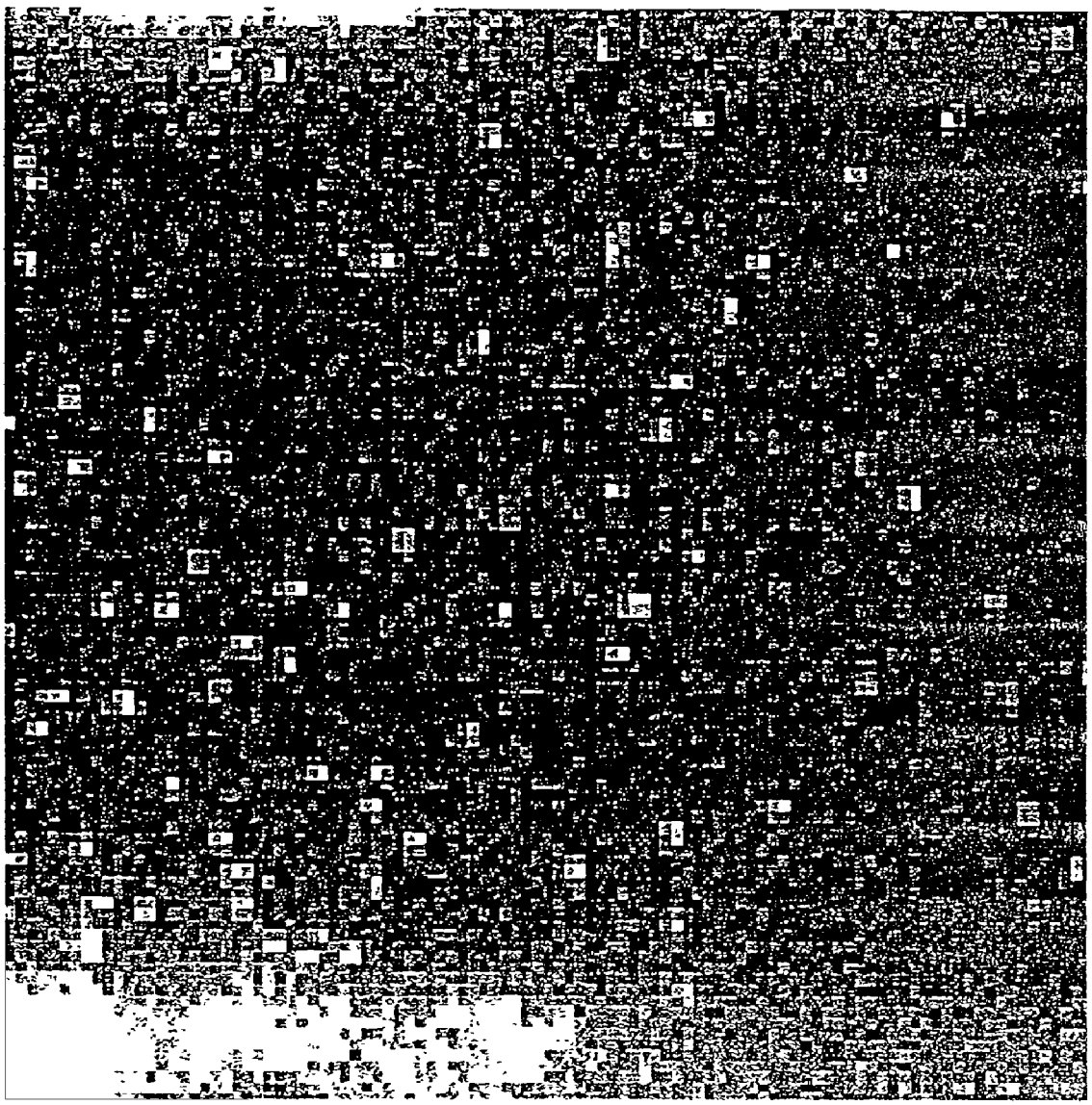
FIG. 12 is a micrograph of single well reactions.

A FORA that has been "carpeted" with mobile solid supports with either nucleic acid or reagent enzymes attached thereto is shown as FIG. 7.

The solid support is optically linked to an imaging system 230, which includes a CCD system in association will conventional optics or a fiber optic bundle. In one embodiment the perfusion chamber substrate includes a fiber optic array wafer such that light generated near the aqueous interface is transmitted directly through the optical fibers to the exterior of the substrate or chamber. When the CCD system includes a fiber optic connector, imaging can be accomplished by placing the perfusion chamber substrate in direct contact with the connector. Alternatively, conventional optics can be used to image the light, e.g., by using a 1-1 magnification high numerical aperture lens system, from the exterior of the fiber optic substrate directly onto the CCD sensor. When the substrate does not provide for fiber optic coupling, a lens system can also be used as described above, in which case either the substrate or the perfusion chamber cover is optically transparent. An exemplary CCD imaging system is described above.

The imaging system 230 is used to collect light from the reactors on the substrate surface. Light can be imaged, for example, onto a CCD using a high sensitivity low noise apparatus known in the art. For fiber-optic based imaging, it is preferable to incorporate the optical fibers directly into the cover slip or for a FORA to have the optical fibers that form the microwells also be the optical fibers that convey light to the detector.

The imaging system is linked to a computer control and data collection system 240. In general, any commonly available hardware and software package can be used. The computer control and data collection system is also linked to the conduit 200 to control reagent delivery.

The photons generated by the pyrophosphate sequencing reaction are captured by the CCD only if they pass through a focusing device (e.g., an optical lens or optical fiber) and are focused upon a CCD element. However, the emitted photons will escape equally in all directions. In order to maximize their subsequent "capture" and quantitation when utilizing a planar array (e.g., a DNA chip), it is preferable to collect the photons as close as possible to the point at which they are generated, e.g. immediately at the planar solid support. This is accomplished by either: (i) utilizing optical immersion oil between the cover slip and a traditional optical lens or optical fiber bundle or, preferably, (ii) incorporating optical fibers directly into the cover slip itself. Similarly, when a thin, optically transparent planar surface is used, the optical fiber bundle can also be placed against its back surface eliminating the need to "image" through the depth of the entire reaction/perfusion chamber.

Detection Means

The reaction event, e.g., photons generated by luciferase, may be detected and quantified using a variety of detection apparatuses, e.g., a photomultiplier tube, a CCD, CMOS, absorbance photometer, a luminometer, charge injection device (CID), or other solid state detector, as well as the apparatuses described herein. In a preferred embodiment, the quantitation of the emitted photons is accomplished by the use of a CCD camera fitted with a fused fiber optic bundle. In another preferred embodiment, the quantitation of the emitted photons is accomplished by the use of a CCD camera fitted with a microchannel plate intensifier. A back-thinned CCD can be used to increase sensitivity. CCD detectors are described in, e.g., Bronks, et al., 1995. *Anal. Chem.* 65: 2750-2757.

An exemplary CCD system is a Spectral Instruments, Inc. (Tucson, Ariz.) Series 600 4-port camera with a Lockheed-Martin LM485 CCD chip and a 1-1 fiber optic connector (bundle) with 6-8 µm individual fiber diameters. This system has 4096×4096, or greater than 16 million pixels and has a quantum efficiency ranging from 10% to >40%. Thus, depending on wavelength, as much as 40% of the photons imaged onto the CCD sensor are converted to detectable electrons.

In other embodiments, a fluorescent moiety can be used as a label and the detection of a reaction event can be carried out using a confocal scanning microscope to scan the surface of an array with a laser or other techniques such as scanning near-field optical microscopy (SNOM) are available which are capable of smaller optical resolution, thereby allowing the use of "more dense" arrays. For example, using SNOM, individual polynucleotides may be distinguished when separated by a distance of less than 100 nm, e.g., 10 nm×10 nm. Additionally, scanning tunneling microscopy (Binning et al., *Helvetica Physica Acta,* 55:726-735, 1982) and atomic force microscopy (Hanswa et al., *Annu Rev Biophys Biomol Struct,* 23:115-139, 1994) can be used.

The invention provides an apparatus for simultaneously monitoring an array of reaction chambers for light indicating that a reaction is taking place at a particular site. The apparatus can include an array of reaction chambers formed from a planar substrate having a plurality of cavitated surfaces, each cavitated surface forming a reaction chamber adapted to contain analytes. The reaction chambers can have a center-to-center spacing of between 5 to 200 µm and the array can have more than 400,000 discrete reaction chambers. The apparatus can also include an optically sensitive device arranged so that in use the light from a particular reaction chamber will impinge upon a particular predetermined region of said optically sensitive device. The apparatus can further include a means for determining the light level impinging upon each predetermined region and a means to record the variation of said light level with time for each of said reaction chamber.

The invention also provides an analytic sensor, which can include an array formed from a first bundle of optical fibers with a plurality of cavitated surfaces at one end thereof, each cavitated surface forming a reaction chamber adapted to contain analytes. The reaction chambers can have a center-to-center spacing of between 5 to 200 µm and the array can have more than 400,000 discrete reaction chambers. The analytic sensor can also include an enzymatic or fluorescent means for generating light in the reaction chambers. The analytic sensor can further include a light detection means comprising a light capture means and a second fiber optic bundle for transmitting light to the light detecting means. The second fiber optic bundle can be in optical contact with the array, such that light generated in an individual reaction chamber is captured by a separate fiber or groups of separate fibers of the second fiber optic bundle for transmission to the light capture means. The light capture means can be a CCD camera as described herein. The reaction chambers can contain one or more mobile solid supports with a bioactive agent immobilized thereon. In some embodiments, the analytic sensor is suitable for use in a biochemical assay or suitable for use in a cell-based assay Methods of Sequencing Nucleic Acids The invention also provides a method for sequencing nucleic acids which generally comprises (a) providing one or more nucleic acid anchor primers and a plurality of single-stranded circular nucleic acid templates disposed within a plurality of reaction chambers or cavities; (b) annealing an effective amount of the nucleic acid anchor primer to at least one of the single-stranded circular templates to yield a primed anchor primer-circular template complex; (c) combining the primed anchor primer-circular template complex with a polymerase to form an extended anchor primer covalently linked to multiple copies of a nucleic acid complementary to the circular nucleic acid template; (d) annealing an effective amount of a sequencing primer to one or more copies of said covalently linked complementary nucleic acid, (e) extending the sequencing primer with a polymerase and a predetermined nucleotide triphosphate to yield a sequencing product and, if the predetermined nucleotide triphosphate is incorporated onto the 3' end of said sequencing primer, a sequencing reaction byproduct; and (f) identifying the sequencing reaction byproduct, thereby determining the sequence of the nucleic acid. In one embodiment, the sequencing byproduct is PPi. In another embodiment, a dATP or ddATP analogue is used in place of deoxy- or dideoxy adenosine triphosphate. This analogue is capable of acting as a substrate for a polymerase but incapable of acting as a substrate for a PPi-detection enzyme. This method can be carried out in separate parallel common reactions in an aqueous environment.

In another aspect, the invention includes a method of determining the base sequence of a plurality of nucleotides on an array, which generally comprises (a) providing a plurality of sample DNAs, each disposed within a plurality of cavities on a planar surface; (b) adding an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates; (c) detecting whether or not the nucleoside 5'-triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triphosphate precursor; and (d) sequentially repeating steps (b) and (c), wherein each sequential repetition adds and, detects the incorporation of one type of activated nucleoside 5'-triphosphate precursor of known nitrogenous base composition; and (e) determining the base sequence of the unpaired nucleotide residues of the template in each reaction chamber from the sequence of incorporation of said nucleoside precursors.

In one embodiment of the invention, the anchor primer is linked to a particle. The anchor primer could be linked to the particle prior to or after formation of the extended anchor primer. The sequencing reaction byproduct could be PPi and a coupled sulfurylase/luciferase reaction is used to generate light for detection. Either or both of the sulfurylase and luciferase could be immobilized on one or more mobile solid supports disposed at each reaction site.

In another aspect, the invention involves, a method of determining the base sequence of a plurality of nucleotides on an array. The method includes providing a plurality of sample DNAs, each disposed within a plurality of cavities on a planar surface, each cavity forming an analyte reaction chamber, wherein the reaction chambers have a center to center spacing of between 5 to 200 μm. Then an activated nucleotide 5'-triphosphate precursor of one known nitrogenous base is added to a reaction mixture in each reaction chamber. Each reaction mixture includes a template-directed nucleotide polymerase and a single-stranded polynucleotide template hybridized to a complementary oligonucleotide primer strand at least one nucleotide residue shorter than the templates to form at least one unpaired nucleotide residue in each template at the 3' end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates. Then it is detected whether or not the nucleoside 5'-triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triphosphate precursor. Then these steps are sequentially repeated, wherein each sequential repetition adds and, detects the incorporation of one type of activated nucleoside 5'-triphosphate precursor of known nitrogenous base composition. The base sequence of the unpaired nucleotide residues of the template in each reaction chamber is then determined from the sequence of incorporation of the nucleoside precursors.

In another aspect, the invention involves a method for determining the nucleic acid sequence in a template nucleic acid polymer. The method includes introducing a plurality of template nucleic acid polymers into a plurality of cavities on a planar surface, each cavity forming an analyte reaction chamber, wherein the reaction chambers have a center to center spacing of between 5 to 200 μm. Each reaction chamber also has a polymerization environment in which the nucleic acid polymer will act as a template polymer for the synthesis of a complementary nucleic acid polymer when nucleotides are added. A series of feedstocks is successively provided to the polymerization environment, each feedstock having a nucleotide selected from among the nucleotides from which the complementary nucleic acid polymer will be formed, such that if the nucleotide in the feedstock is complementary to the next nucleotide in the template polymer to be sequenced the nucleotide will be incorporated into the complementary polymer and inorganic pyrophosphate will be released. Then the formation of inorganic pyrophosphate is detected to determine the identity of each nucleotide in the complementary polymer and thus the sequence of the template polymer.

In another aspect, the invention involves, a method of identifying the base in a target position in a DNA sequence of sample DNA. The method includes providing a sample of DNA disposed within a plurality of cavities on a planar surface, each cavity forming an analyte reaction chamber, wherein the reaction chambers have a center to center spacing of between 5 to 200 μm, the DNA being rendered single stranded either before or after being disposed in the reaction chambers. An extension primer is then provided which hybridizes to the immobilized single-stranded DNA at a position immediately adjacent to the target position. The immobilized single-stranded DNA is subjected to a polymerase reaction in the presence of a predetermined nucleotide triphosphate, wherein if the predetermined nucleotide triphosphate is incorporated onto the 3' end of the sequencing primer then a sequencing reaction byproduct is formed. The sequencing reaction byproduct is then identified, thereby determining the nucleotide complementary to the base at the target position.

In another aspect, the invention involves a method of identifying a base at a target position in a sample DNA sequence. The method includes providing sample DNA disposed within a plurality of cavities on a planar surface, each cavity forming an analyte reaction chamber, wherein the reaction chambers have a center to center spacing of between 5 to 200 μm, the DNA being rendered single stranded either before or after being disposed in the reaction chambers and providing an extension primer which hybridizes to the sample DNA immediately adjacent to the target position. The sample DNA sequence and the extension primer are then subjected to a polymerase reaction in the presence of a nucleotide triphosphate whereby the nucleotide triphosphate will only become incorporated and release pyrophosphate (PPi) if it is complementary to the base in the target position, the nucleotide triphosphate being added either to separate aliquots of sample-primer mixture or successively to the same sample-primer mixture. The release of PPi is then detected to indicate which nucleotide is incorporated.

In another aspect, the invention involves a method of identifying a base at a target position in a single-stranded sample DNA sequence. The method includes providing an extension primer which hybridizes to sample DNA immediately adjacent to the target position, the sample DNA disposed within a plurality of cavities on a planar surface, each cavity forming an analyte reaction chamber, wherein the reaction chambers have a center to center spacing of between 5 to 200 um, the DNA being rendered single stranded either before or after being disposed in the reaction chambers. The sample DNA and extension primer is subjected to a polymerase reaction in the presence of a predetermined deoxynucleotide or dideoxynucleotide whereby the deoxynucleotide or dideoxynucleotide will only become incorporated and release pyrophosphate (PPi) if it is complementary to the base in the target position, the predetermined deoxynucleotides or dideoxynucleotides being added either to separate aliquots of sample-primer mixture or successively to the same sample-primer mixture. Any release of PPi is detected enzymatically to indicate which deoxynucleotide or dideoxynucleotide is incorporated. Characterized in that, the PPi-detection enzyme(s) are included in the polymerase reaction step and in that in place of deoxy- or dideoxy adenosine triphosphate (ATP) a dATP or ddATP analogue is used which is capable of acting as a substrate for a polymerase but incapable of acting as a substrate for a the PPi—detection enzyme.

In another aspect, the invention involves a method for sequencing a nucleic acid. The method includes providing one or more nucleic acid anchor primers; and a plurality of nucleic acid templates disposed within a plurality of cavities on the above described arrays. An effective amount of the nucleic acid anchor primer is annealed to at least one of the single-stranded circular templates to yield a primed anchor primer-circular template complex. The primed anchor primer-circular template complex is then combined with a polymerase to form an extended anchor primer covalently linked to multiple copies of a nucleic acid complementary to the circular nucleic acid template; followed by annealing of an effective amount of a sequencing primer to one or more copies of the covalently linked complementary nucleic acid. The sequencing primer is then extended with a polymerase and a predetermined nucleotide triphosphate to yield a sequencing product and, if the predetermined nucleotide triphosphate is incorporated onto the 3' end of the sequencing primer, a sequencing reaction byproduct. Then the sequencing reaction byproduct is identified, thereby determining the sequence of the nucleic acid.

Structure of Anchor Primers

The anchor primers of the invention generally comprise a stalk region and at least one adaptor region. In a preferred embodiment the anchor primer contains at least two contiguous adapter regions. The stalk region is present at the 5' end of the anchor primer and includes a region of nucleotides for attaching the anchor primer to the solid substrate.

The adaptor region(s) comprise nucleotide sequences that hybridize to a complementary sequence present in one or more members of a population of nucleic acid sequences. In some embodiments, the anchor primer includes two adjoining adaptor regions, which hybridize to complementary regions ligated to separate ends of a target nucleic acid sequence. This embodiment is illustrated in FIG. 1, which is discussed in more detail below. In additional embodiments, the adapter regions in the anchor primers are complementary to non-contiguous regions of sequence present in a second nucleic acid sequence. Each adapter region, for example, can be homologous to each terminus of a fragment produced by digestion with one or more restriction endonucleases. The fragment can include, e.g., a sequence known or suspected to contain a sequence polymorphism. Additionally, the anchor primer may contain two adapter regions that are homologous to a gapped region of a target nucleic acid sequence, i.e., one that is non-contiguous because of a deletion of one or more nucleotides. When adapter regions having these sequences are used, an aligning oligonucleotide corresponding to the gapped sequence may be annealed to the anchor primer along with a population of template nucleic acid molecules.

The anchor primer may optionally contain additional elements such as one or more restriction enzyme recognition sites, RNA polymerase binding sites, e.g., a T7 promoter site, or sequences present in identified DNA sequences, e.g., sequences present in known genes. The adapter region(s) may also include sequences known to flank sequence polymorphisms. Sequence polymorphisms include nucleotide substitutions, insertions, deletions, or other rearrangements which result in a sequence difference between two otherwise identical nucleic acid sequences. An example of a sequence polymorphism is a single nucleotide polymorphism (SNP).

In general, any nucleic acid capable of base-pairing can be used as an anchor primer. In some embodiments, the anchor primer is an oligonucleotide. As utilized herein the term oligonucleotide includes linear oligomers of natural or modified monomers or linkages, e.g., deoxyribonucleosides, ribonucleosides, anomeric forms thereof, peptide nucleic acids (PNAs), and the like, that are capable of specifically binding to a target polynucleotide by way of a regular pattern of monomer-to-monomer interactions. These types of interactions can include, e.g., Watson-Crick type of base-pairing, base stacking, Hoogsteen or reverse-Hoogsteen types of base-pairing, or the like. Generally, the monomers are linked by phosphodiester bonds, or analogs thereof, to form oligonucleotides ranging in size from, e.g., 3-200, 8-150, 10-100, 20-80, or 25-50 monomeric units. Whenever an oligonucleotide is represented by a sequence of letters, it is understood that the nucleotides are oriented in the 5'→3' direction, from left-to-right, and that the letter "A" donates deoxyadenosine, the letter "T" denotes thymidine, the letter "C" denotes deoxycytosine, and the letter "G" denotes deoxyguanosine, unless otherwise noted herein. The oligonucleotides of the present invention can include non-natural nucleotide analogs. However, where, for example, processing by enzymes is required, or the like, oligonucleotides comprising naturally occurring nucleotides are generally required for maintenance of biological function.

Linking Primers to Solid Substrates

Anchor primers are linked to the solid substrate at the sensitized sites. A region of a solid substrate containing a linked primer is referred to herein as an anchor pad. Thus, by specifying the sensitized states on the solid support, it is possible to form an array or matrix of anchor pads. The anchor pads can be, e.g., small diameter spots etched at evenly spaced intervals on the solid support. The anchor pads can be located at the bottoms of the cavitations or wells if the substrate has been cavitated, etched, or other vise micromachined as discussed above.

In one embodiment, the anchor primer is linked to a particle. The anchor primer can be linked to the particle prior to formation of the extended anchor primer or after formation of the extended anchor primer.

The anchor primer can be attached to the solid support via a covalent or non-covalent interaction. In general, any linkage recognized in the art can be used. Examples of such linkages common in the art include any suitable metal (e.g., $Co^{2+}$, $Ni^{2+}$)-hexahistidine complex, a biotin binding protein, e.g., NEUTRAVIDIN™ modified avidin (Pierce Chemicals, Rockford, Ill.), streptavidin/biotin, avidin/biotin, glutathione S-transferase (GST)/glutathione, monoclonal antibody/antigen, and maltose binding protein/maltose, and pluronic coupling technologies. Samples containing the appropriate tag are incubated with the sensitized substrate so that zero, one, or multiple molecules attach at each sensitized site.

One biotin-(strept-)avidin-based anchoring method uses a thin layer of a photoactivatable biotin analog dried onto a solid surface. (Hengsakul and Cass, 1996. *Bioconjugate Chem.* 7: 249-254). The biotin analog is then exposed to white light through a mask, so as to create defined areas of activated biotin. Avidin (or streptavidin) is then added and allowed to bind to the activated biotin. The avidin possesses free biotin binding sites which can be utilized to "anchor" the biotinylated oligonucleotides through a biotin-(strept-)avidin linkage.

Alternatively, the anchor primer can be attached to the solid support with a biotin derivative possessing a photo-removable protecting group. This moiety is covalently bound to bovine serum albumin (BSA), which is attached to the solid support, e.g., a glass surface. See Pirrung and Huang, 1996, *Bioconjugate Chem.* 7: 317-321. A mask is then used to create activated biotin within the defined irradiated areas Avidin may then be localized to the irradiated area, with biotinylated DNA subsequently attached through a BSA-biotin-avidin-biotin link. If desired, an intermediate layer of silane is deposited in a self-assembled monolayer on a silicon dioxide silane surface that can be patterned to localize BSA binding in defined regions. See e.g., Mooney, et al., 1996. *Proc. Natl. Acad. Sci. USA* 93: 12287-12291.

In pluronic based attachment, the anchor primers are first attached to the termini of a polyethylene oxide-polypropylene oxide-polyethylene oxide triblock copolymer, which is also known as a pluronic compound. The pluronic moiety can be used to attach the anchor primers to a solid substrate. Pluronics attach to hydrophobic surfaces by virtue of the reaction between the hydrophobic surface and the polypropylene oxide. The remaining polyethylene oxide groups extend off the surface, thereby creating a hydrophilic environment. Nitrilotriacetic acid (NTA) can be conjugated to the terminal ends of the polyethylene oxide chains to allow for hexahistidine tagged anchor primers to be attached. In another embodiment, pyridyl disulfide (PDS) can be conjugated to the ends of the polyethylene chains allowing for attachment of a thiolated anchor primer via a disulfide bond. In one preferred embodiment, Pluronic F108 (BASF Corp.) is used for the attachment.

Each sensitized site on a solid support is potentially capable of attaching multiple anchor primers. Thus, each anchor pad may include one or more anchor primers. It is preferable to maximize the number of pads that have only a single productive reaction center (e.g., the number of pads that, after the extension reaction, have only a single sequence extended from the anchor primer). This can be accomplished by techniques which include, but are not limited to: (i) varying the dilution of biotinylated anchor primers that are washed over the surface; (ii) varying the incubation time that the biotinylated primers are in contact with the avidin surface; (iii) varying the concentration of open- or closed-circular template so that, on average, only one primer on each pad is extended to generate the sequencing template; or (iv) reducing the size of the anchor pad to approach single-molecule dimensions (<1 µm) such that binding of one anchor inhibits or blocks the binding of another anchor (e.g. by photoactivation of a small spot), or (v) reducing the size of the anchor pad such that binding of one circular template inhibits or blocks the binding of a second circular template.

In some embodiments, each individual pad contains just one linked anchor primer. Pads having only one anchor primer can be made by performing limiting dilutions of a selected anchor primer on to the solid support such that, on average, only one anchor primer is deposited on each pad. The concentration of anchor primer to be applied to a pad can be calculated utilizing, for example, a Poisson distribution model.

In order to maximize the number of reaction pads that contain a single anchor primer, a series of dilution experiments are performed in which a range of anchor primer concentrations or circular template concentrations are varied. For highly dilute concentrations of primers, primers and circular templates binding to the same pad will be independent of each other, and a Poisson distribution will characterize the number of anchor primers extended on any one pad. Although there will be variability in the number of primers that are actually extended, a maximum of 37% of the pads will have a single extended anchor primer (the number of pads with a single anchor oligonucleotide). This number can be obtained as follows.

Let $N_p$ be the average number of anchor primers on a pad and f be the probability that an anchor primer is extended with a circular template. Then the average number of extended anchor primers per pad is $N_p f$, which is defined as the quantity a. There will be variability in the number of primers that are actually extended. In the low-concentration limit, primers and circular templates binding to the same pad will be independent of each other, and a Poisson distribution P(n) will characterize the number of anchor primers n extended on any pad. This distribution may be mathematically defined by: $P(n)=(a^n/n!)\exp(-a)$, with $P(1)=a \exp(-a)$. The probability P(1) assumes its maximum value $\exp(-1)$ for a=1, with 37% of pads having a single extended anchor primer.

A range of anchor primer concentrations and circular template concentrations may be subsequently scanned to find a value of $N_p f$ closest to 1. A preferable method to optimize this distribution is to allow multiple anchor primers on each reaction pad, but use a limiting dilution of circular template so that, on average, only one primer on each pad is extended to generate the sequencing template.

Alternatively, at low concentrations of anchor primers, at most one anchor primer will likely be bound on each reaction pad. A high concentration of circular template may be used so that each primer is likely to be extended.

Where the reaction pads are arrayed on a planar surface or a fiber optic array, the individual pads are approximately 10 µm on a side, with a 100 µm spacing between adjacent pads. Hence, on a 1 cm² surface a total of approximately 10,000 microreactors could be deposited, and, according to the Poisson distribution, approximately 3700 of these will contain a single anchor primer. In certain embodiments, after the primer oligonucleotide has been attached to the solid support, modified, e.g., biotinylated, enzymes are deposited to bind to the remaining, unused avidin binding sites on the surface.

In other embodiments multiple anchor primers are attached to any one individual pad in an array. Limiting dilutions of a plurality of circular nucleic acid templates (described in more detail below) may be hybridized to the anchor primers so immobilized such that, on average, only one primer on each pad is hybridized to a nucleic acid template. Library concentrations to be used may be calculated utilizing, for example, limiting dilutions and a Poisson distribution model.

Nucleic Acid Templates

The nucleic acid templates that can be sequenced according to the invention, e.g., a nucleic acid library, in general can include open circular or closed circular nucleic acid molecules. A "closed circle" is a covalently closed circular nucleic acid molecule, e.g. a circular DNA or RNA molecule. An "open circle" is a linear single-stranded nucleic acid molecule having a 5' phosphate group and a 3' hydroxyl group. In one embodiment, the single stranded nucleic acid contains at least 100 copies of nucleic acid sequence, each copy covalently linked end to end. In some embodiments, the open circle is formed in situ from a linear double-stranded nucleic acid molecule. The ends of a given open circle nucleic acid molecule can be ligated by DNA ligase. Sequences at the 5' and 3' ends of the open circle molecule are complementary to two regions of adjacent nucleotides in a second nucleic acid molecule, e.g., an adapter region of an anchor primer, or to two regions that are nearly adjoining in a second DNA molecule. Thus, the ends of the open-circle molecule can be ligated using DNA ligase, or extended by DNA polymerase in a gap-filling reaction. Open circles are described in detail in Lizardi, U.S. Pat. No. 5,854,033. An open circle can be converted to a closed circle in the presence of a DNA ligase (for DNA) or RNA ligase following, e.g., annealing of the open circle to an anchor primer.

If desired, nucleic acid templates can be provided as padlock probes. Padlock probes are linear oligonucleotides that include target-complementary sequences located at each end, and which are separated by a linker sequence. The linkers can be ligated to ends of members of a library of nucleic acid sequences that have been, e.g., physically sheared or digested with restriction endonucleases. Upon hybridization to a target-sequence, the 5'-and 3'-terminal regions of these linear oligonucleotides are brought in juxtaposition. This juxtaposition allows the two probe segments (if properly hybridized) to be covalently-bound by enzymatic ligation (e.g., with T4 DNA ligase), thus converting the probes to circularly-closed molecules which are catenated to the specific target sequences (see e.g., Nilsson, et al, 1994. *Science* 265: 2085-2088). The resulting probes are suitable for the simultaneous analysis of many gene sequences both due to their specificity and selectivity for gene sequence variants (see e.g., Lizardi, et al., 1998. *Nat. Genet.* 19: 225-232; Nilsson, et al, 1997. *Nat. Genet.* 16: 252-255) and due to the fact that the resulting reaction products remain localized to the specific target sequences. Moreover, intramolecular ligation of many different probes is expected to be less susceptible to non-specific cross-reactivity than multiplex PCR-based methodologies where non-cognate pairs of primers can give rise to irrelevant amplification products (see e.g., Landegren and Nilsson, 1997. *Ann. Med.* 29: 585-590).

A starting library can be constructed comprising either single-stranded or double-stranded nucleic acid molecules provided that the nucleic acid sequence includes a region that, if present in the library, is available for annealing, or can be made available for annealing, to an anchor primer sequence. For example, when used as a template for rolling circle amplification, a region of a double-stranded template needs to be at least transiently single-stranded in order to act as a template for extension of the anchor primer Library templates can include multiple elements, including, but not limited to, one or more regions that are complementary to the anchor primer. For example, the template libraries may include a region complementary to a sequencing primer, a control nucleotide region, and an insert sequence comprised of the sequencing template to be subsequently characterized. As is explained in more detail below, the control nucleotide region is used to calibrate the relationship between the amount of byproduct and the number of nucleotides incorporated. As utilized herein the term "complement" refers to nucleotide sequences that are able to hybridize to a specific nucleotide sequence to form a matched duplex.

In one embodiment, a library template includes: (i) two distinct regions that are complementary to the anchor primer, (ii) one region homologous to the sequencing primer, (iii) one optional control nucleotide region, (iv) an insert sequence of, e.g., 30-500, 50-200, or 60-100 nucleotides, that is to be sequenced. The template can, of course, include two, three or all four of these features.

The template nucleic acid can be constructed from any source of nucleic acid, e.g., any cell, tissue, or organism, and can be generated by any art-recognized method. Suitable methods include, e.g., sonication of genomic DNA and digestion with one or more restriction endonucleases (RE) to generate fragments of a desired range of lengths from an initial population of nucleic acid molecules. Preferably, one or more of the restriction enzymes have distinct four-base recognition sequences. Examples of such enzymes include, e.g., Sau3A1, MspI, and TaqI. Preferably, the enzymes are used in conjunction with anchor primers having regions containing recognition sequences for the corresponding restriction enzymes. In some embodiments, one or both of the adapter regions of the anchor primers contain additional sequences adjoining known restriction enzyme recognition sequences, thereby allowing for capture or annealing to the anchor primer of specific restriction fragments of interest to the anchor primer. In other embodiments, the restriction enzyme is used with a type IIS restriction enzyme.

Alternatively, template libraries can be made by generating a complementary DNA (cDNA) library from RNA, e.g., messenger RNA (mRNA). The cDNA library can, if desired, be further processed with restriction endonucleases to obtain a 3' end characteristic of a specific RNA, internal fragments, or fragments including the 3' end of the isolated RNA. Adapter regions in the anchor primer may be complementary to a sequence of interest that is thought to occur in the template library, e.g., a known or suspected sequence polymorphism within a fragment generated by endonuclease digestion.

In one embodiment, an indexing oligonucleotide can be attached to members of a template library to allow for subsequent correlation of a template nucleic acid with a population of nucleic acids from which the template nucleic acid is derived. For example, one or more samples of a starting DNA population can be fragmented separately using any of the previously disclosed methods (e g, restriction digestion, sonication). An indexing oligonucleotide sequence specific for each sample is attached to, e.g., ligated to, the termini of members of the fragmented population. The indexing oligonucleotide can act as a region for circularization, amplification and, optionally, sequencing, which permits it to be used to index, or code, a nucleic acid so as to identify the starting sample from which it is derived Distinct template libraries made with a plurality of distinguishable indexing primers can be mixed together for subsequent reactions. Determining the sequence of the member of the library allows for the identification of a sequence corresponding to the indexing oligonucleotide. Based on this information, the origin of any given fragment can be inferred.

Annealing and Amplification of Primer-Template Nucleic Acid Complexes

Libraries of nucleic acids are annealed to anchor primer sequences using recognized techniques (see, e.g., Hatch, et al, 1999. *Genet Anal. Biomol Engineer.* 15:35-40; Kool, U.S. Pat. No. 5,714,320 and Lizardi, U.S. Pat. No. 5,854,033). In general, any procedure for annealing the anchor primers to the template nucleic acid sequences is suitable as long as it results in formation of specific, i.e., perfect or nearly perfect, complementarily between the adapter region or regions in the anchor primer sequence and a sequence present in the template library.

A number of in vitro nucleic acid amplification techniques may be utilized to extend the anchor primer sequence. The size of the amplified DNA preferably is smaller than the size of the anchor pad and also smaller than the distance between anchor pads.

The amplification is typically performed in the presence of a polymerase, e.g., a DNA or RNA-directed DNA polymerase, and one, two, three, or four types of nucleotide triphosphates, and, optionally, auxiliary binding proteins. In general, any polymerase capable of extending a primed 3'-OH group can be used a long as it lacks a 3' to 5' exonuclease activity. Suitable polymerases include, e.g., the DNA polymerases from *Bacillus stearothermophilus*, *Thermus acquaticus*, *Pyrococcus furiosis*, *Thermococcus litoralis*, and *Thermus thermophilus*, bacteriophage T4 and T7, and the *E coli* DNA polymerase I Klenow fragment. Suitable RNA-directed DNA polymerases include, e.g., the reverse transcriptase from the Avian Myeloblastosis Virus, the reverse transcriptase from the Moloney Murine Leukemia Virus, and the reverse transcriptase from the Human Immunodeficiency Virus-I.

A number of in vitro nucleic acid amplification techniques have been described. These amplification methodologies may be differentiated into those methods: (i) which require temperature cycling—polymerase chain reaction (PCR) (see e.g., Saiki, et al., 1995. *Science* 230: 1350-1354), ligase chain reaction (see e.g., Barany, 1991. *Proc. Natl. Acad. Sci. USA* 88: 189-193; Barringer, et al., 1990. *Gene* 89: 117-122) and transcription-based amplification (see e.g., Kwoh, et al, 1989. *Proc. Natl. Acad. Sci. USA* 86:1173-1177) and (ii) isothermal amplification systems—self-sustaining, sequence replication (see e.g., Guatelli, et al., 1990. *Proc. Natl. Aced Sci. USA* 87: 1874-1878); the Qβ replicase system (see e.g., Lizardi, et al, 1988. *Biotechnology* 6: 1197-1202); strand displacement amplification Nucleic Acids Res. 1992 Apr. 11: 20(7):1691-6; and the methods described in PNAS 1992 Jan. 1; 89(1): 392-6; and NASBA J Virol Methods. 1991 December; 35(3):273-86.

Isothermal amplification also includes rolling circle-based amplification (RCA). RCA is discussed in, e.g., Kool, U.S. Pat. No. 5,714,320 and Lizardi, U.S. Pat. No. 5,854,033; Hatch, et al., 1999. *Genet. Anal Biomol. Engineer.* 15: 35-40. The result of the RCA is a single DNA strand extended from the 3' terminus of the anchor primer (and thus is linked to the solid support matrix) and including a concatamer containing multiple copies of the circular template annealed to a primer sequence. Typically, 1,000 to 10,000 or more copies of circular templates, each having a size of, e.g., approximately 30-500, 50-200, or 60-100 nucleotides size range, can be obtained with RCA.

The product of RCA amplification following annealing of a circular nucleic acid molecule to an anchor primer is shown schematically in FIG. 1A. A circular template nucleic acid 102 is annealed to an anchor primer 104, which has been linked to a surface 106 at its 5' end and has a free 3' OH available for extension. The circular template nucleic acid 102 includes two adapter regions 108 and 110 which are complementary to regions of sequence in the anchor primer 104. Also included in the circular template nucleic acid 102 is an insert 112 and a region 114 homologous to a sequencing primer, which is used in the sequencing reactions described below.

Upon annealing, the free 3'-OH on the anchor primer 104 can be extended using sequences within the template nucleic acid 102. The anchor primer 102 can be extended along the template multiple times, with each iteration adding to the sequence extended from the anchor primer a sequence complementary to the circular template nucleic acid. Four iterations, or four rounds of rolling circle replication, are shown in FIG. 1A as the extended anchor primer amplification product 114. Extension of the anchor primer results in an amplification product covalently or otherwise physically attached to the substrate 106.

Figure 1B:
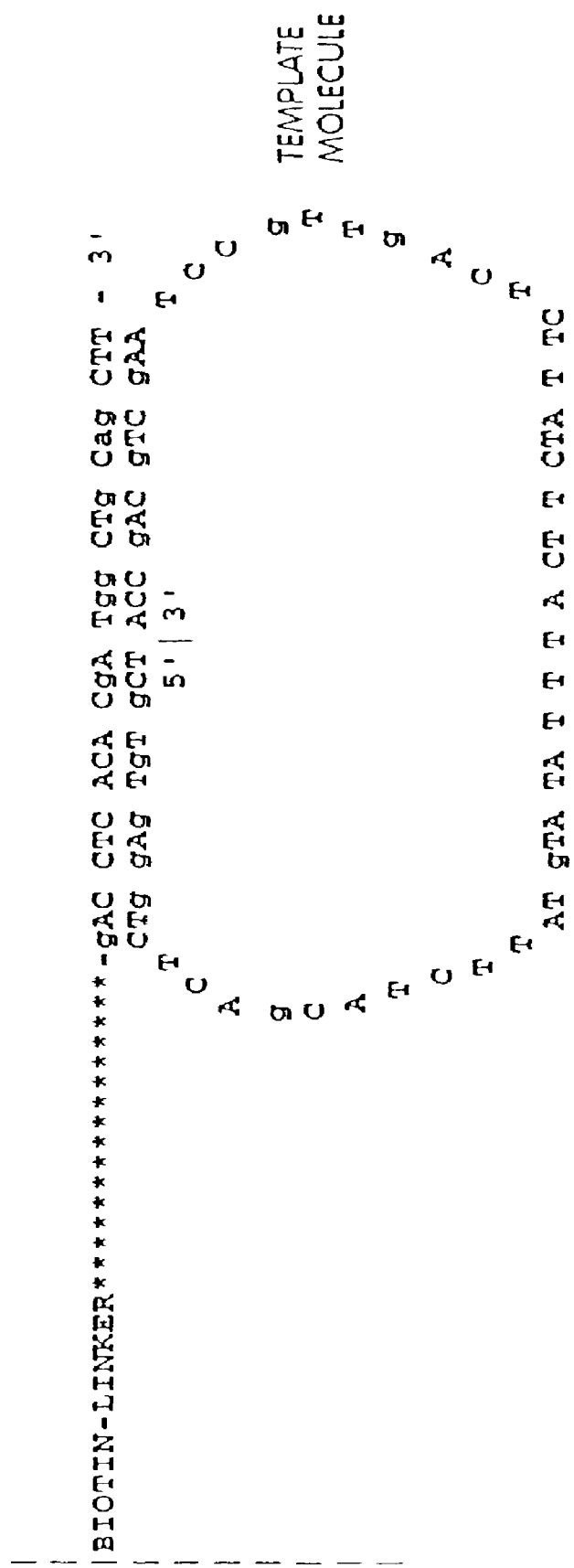
Figure 1D:
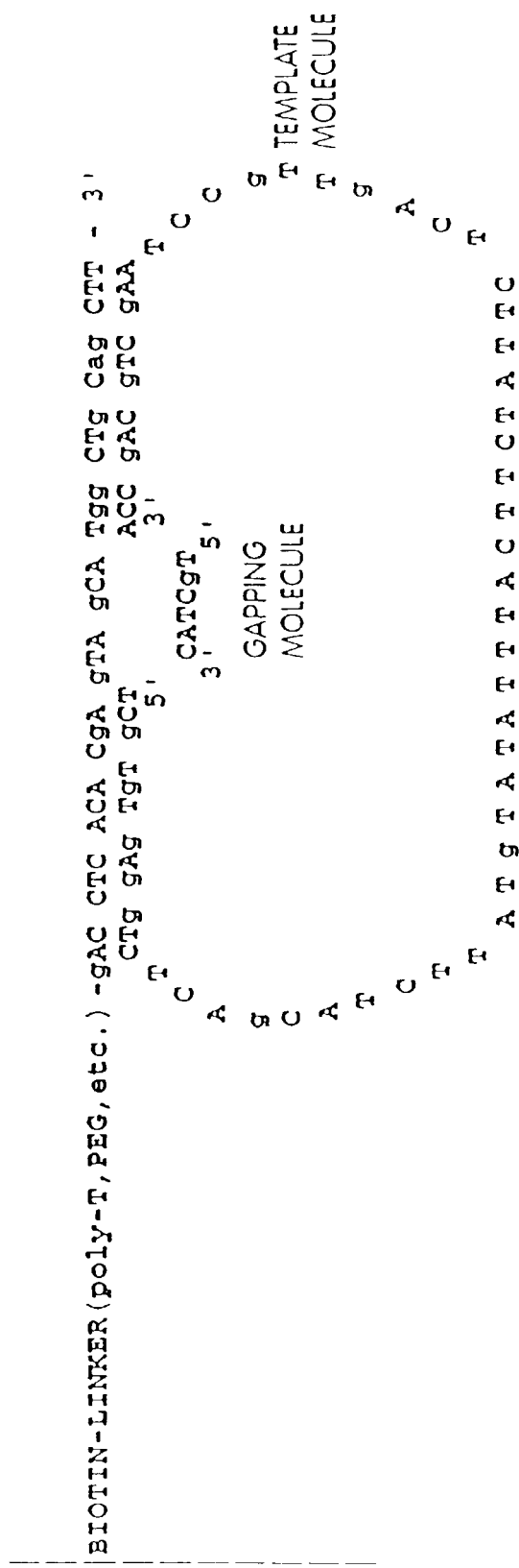

Additional embodiments of circular templates and anchor primers are shown in more detail in FIGS. 1B-1D. FIG. 1B illustrates an annealed open circle linear substrate that can serve, upon ligation, as a template for extension of an anchor primer. A template molecule having the sequence 5'-TCg TgT gAg gTC TCA gCA TCT TAT gTA TAT TTA CTT CTA TTC TCA gTT gCC TAA gCT gCA gCC A-3' (SEQ ID NO:1) is annealed to an anchor primer having a biotin linker at its 5' terminus and the sequence 5'-gAC CTC ACA CgA Tgg CTg CAg CTT-3' (SEQ ID NO:2). Annealing of the template results in juxtaposition of the 5' and 3' ends of the template molecule. The 3'OH of the anchor primer can be extended using the circular template.

The use of a circular template and an anchor primer for identification of single nucleotide polymorphisms is shown in FIG. 1C. Shown is a generic anchor primer having the sequence 5'-gAC CTC ACA CgA Tgg CTg CAg CTT-3' (SEQ ID NO:3). The anchor primer anneals to an SNP probe having the sequence 5'-TTT ATA TgT ATT CTA CgA CTC Tgg AgT gTg CTA CCg ACg TCg AAt CCg TTg ACT CTT ATC TTC A-3' (SEQ ID NO:4). The SNP probe in turn hybridizes to a region of a SNP-containing region of a gene having the sequence 5'-CTA gCT CgT ACA TAT AAA TgA AgA TAA gAT CCT g-3' (SEQ ID NO:5). Hybridization of a nucleic acid sequence containing the polymorphism to the SNP probe complex allows for subsequent ligation and circularization of the SNP probe. The SNP probe is designed so that its 5' and 3' termini anneal to the genomic region so as to abut in the region of the polymorphic site, as is indicated in FIG. 1C. The circularized SNP probe can be subsequently extended and sequenced using the methods described herein. A nucleic acid lacking the polymorphism does not hybridize so as to result in juxtaposition of the 5' and 3' termini of the SNP probe. In this case, the SNP probe cannot be ligated to form a circular substrate needed for subsequent extension.

FIG. 1D illustrates the use of a gap oligonucleotide to along with a circular template molecule. An anchor primer having the sequence 5'-gAC CTC ACA CgA gTA gCA Tgg CTg CAg CTT-3' (SEQ ID NO:6) is attached to a surface through a biotin linker. A template molecule having the sequence 5'-TCg TgT gAg gTC TCA gCA TCT TAT gTA TAT TTA CTT CTA TTC TCA gTT gCC TAA gCT gCA gCC A-3' (SEQ ID NO:7) is annealed to the anchor primer to result in partially single stranded, or gapped region, in the anchor primer flanked by a double-stranded region A gapping molecule having the sequence 5'-TgC TAC-3' then anneals to the anchor primer. Ligation of both ends of the gap oligonucleotide to the template molecule results in formation of a circular nucleic acid molecule that can act as a template for rolling circle amplification.

Circular oligonucleotides that are generated during polymerase-mediated DNA replication are dependent upon the relationship between the template and the site of replication initiation. In double-stranded DNA templates, the critical features include whether the template is linear or circular in nature, and whether the site of initiation of replication (r e, the replication "fork") is engaged in synthesizing both strands of DNA or only one. In conventional double-stranded DNA replication, the replication fork is treated as the site at which the new strands of DNA are synthesized.

However, in linear molecules (whether replicated unidirectionally or bidirectionally), the movement of the replication fork(s) generate a specific type of structural motif. If the template is circular, one possible spatial orientation of the replicating molecule takes the form of a θ structure.

Alternatively, RCA can occur when the replication of the duplex molecule begins at the origin. Subsequently, a nick opens one of the strands, and the free 3'-terminal hydroxyl moiety generated by the nick is extended by the action of DNA polymerase. The newly synthesized strand eventually displaces the original parental DNA strand. This aforementioned type of replication is known as rolling-circle replication (RCR) because the point of replication may be envisaged as "rolling around" the circular template strand and, theoretically, it could continue to do so indefinitely. Additionally, because the newly synthesized DNA strand is covalently-bound to the original template, the displaced strand possesses the original genomic sequence (e.g., gene or other sequence of interest) at its 5'-terminus. In RCR, the original genomic sequence is followed by any number of "replication units" complementary to the original template sequence, wherein each replication unit is synthesized by continuing revolutions of said original template sequence. Hence, each subsequent revolution displaces the DNA which is synthesized in the previous replication cycle.

In vivo, RCR is utilized in several biological systems. For example, the genome of several bacteriophage are single-stranded, circular DNA. During replication, the circular DNA is initially converted to a duplex form, which is then replicated by the aforementioned rolling-circle replication mechanism. The displaced terminus generates a series of genomic units that can be cleaved and inserted into the phage particles. Additionally, the displaced single-strand of a rolling-circle can be converted to duplex DNA by synthesis of a complementary DNA strand. This synthesis can be used to generate the concatemeric duplex molecules required for the maturation of certain phage DNAs. For example, this provides the principle pathway by which λ bacteriophage matures RCR is also used in vivo to generate amplified rDNA in Xenopus oocytes, and this fact may help explain why the amplified rDNA is comprised of a large number of identical repeating units. In this case, a single genomic repeating unit is converted into a rolling-circle. The displaced terminus is then converted into duplex DNA which is subsequently cleaved from the circle so that the two termini can be ligated together so as to generate the amplified circle of rDNA.

Through the use of the RCA reaction, a strand may be generated which represents many tandem copies of the complement to the circularized molecule. For example, RCA has recently been utilized to obtain an isothermal cascade amplification reaction of circularized padlock probes in vitro in order to detect single-copy genes in human genomic DNA samples (see Lizardi, et al., 1998. *Nat. Genet.* 19: 225-232). In addition, RCA has also been utilized to detect single DNA molecules in a solid phase-based assay, although difficulties arose when this technique was applied to in situ hybridization (see Lizardi, et al., 1998. *Nat. Genet.* 19: 225-232).

If desired, RCA can be performed at elevated temperatures, e.g., at temperatures greater than 37° C., 42° C., 45° C., 50° C., 60° C., or 70° C. In addition, RCA can be performed initially at a lower temperature, e.g., room temperature, and then shifted to an elevated temperature. Elevated temperature RCA is preferably performed with thermostable nucleic acid polymerases and with primers that can anneal stably and with specificity at elevated temperatures.

RCA can also be performed with non-naturally occurring oligonucleotides, e.g., peptide nucleic acids. Further, RCA can be performed in the presence of auxiliary proteins such as single-stranded binding proteins.

The development of a method of amplifying short DNA molecules which have been immobilized to a solid support, termed RCA has been recently described in the literature (see e.g., Hatch, et al., 1999. *Genet. Anal. Biomol. Engineer.* 15: 35-40; Zhang, et al., 1998. *Gene* 211: 277-85; Baner, et al., 1998. *Nucl. Acids Res.* 26: 5073-5078; Liu, et al., 1995. *J. Am. Chem. Soc.* 118: 1587-1594; Fire and Xu, 1995. *Proc. Natl. Acad. Sci. USA* 92: 4641-4645; Nilsson, et al., 1994. *Science* 265: 2085-2088). RCA targets specific DNA sequences through hybridization and a DNA ligase reaction. The circular product is then subsequently used as a template in a rolling circle replication reaction.

RCA driven by DNA polymerase can replicate circularized oligonucleotide probes with either linear or geometric kinetics under isothermal conditions. In the presence of two primers (one hybridizing to the +strand, and the other, to the −strand of DNA), a complex pattern of DNA strand displacement ensues which possesses the ability to generate $1 \times 10^9$ or more copies of each circle in a short period of time (i.e., less-than 90 minutes), enabling the detection of single-point mutations within the human genome. Using a single primer, RCA generates hundreds of randomly-linked copies of a covalently closed circle in several minutes. If solid support matrix-associated, the DNA product remains bound at the site of synthesis, where it may be labeled, condensed, and imaged as a point light source. For example, linear oligonucleotide probes, which can generate RCA signals, have been bound covalently onto a glass surface. The color of the signal generated by these probes indicates the allele status of the target, depending upon the outcome of specific, target-directed ligation events. As RCA permits millions of individual probe molecules to be counted and sorted, it is particularly amenable for the analysis of rare somatic mutations. RCA also shows promise for the detection of padlock probes bound to single-copy genes in cytological preparations.

In addition, a solid-phase RCA methodology has also been developed to provide an effective method of detecting constituents within a solution. Initially, a recognition step is used to generate a complex h a circular template is bound to a surface. A polymerase enzyme is then used to amplify the bound complex. RCA uses small DNA probes that are amplified to provide an intense signal using detection methods, including the methods described in more detail below.

Other examples of isothermal amplification systems include, e.g., (i) self-sustaining, sequence replication (see e.g., Guatelli, et al., 1990. *Proc. Natl. Acad. Sci. USA* 87: 1874-1878), (ii) the Qβ replicase system (see e.g., Lizardi, et al., 1988. *BioTechnology* 6: 1197-1202), and (iii) nucleic acid sequence-based amplification (NASBA™; see Kievits, et al., 1991. *J. Virol. Methods* 35: 273-286).

Methods for Determining the Nucleotide Sequence of the Amplified Product

Amplification of a nucleic acid template as described above results in multiple copies of a template nucleic acid sequence covalently linked to an anchor primer. In one embodiment, a region of the sequence product is determined by annealing a sequencing primer to a region of the template nucleic acid, and then contacting the sequencing primer with a DNA polymerase and a known nucleotide triphosphate, i.e., dATP, dCTP, dGTP, dTTP, or an analog of one of these nucleotides. The sequence can be determined by detecting a sequence reaction byproduct, as is described below.

The sequence primer can be any length or base composition, as long as it is capable of specifically annealing to a region of the amplified nucleic acid template. No particular structure for the sequencing primer is required so long as it is able to specifically prime a region on the amplified template nucleic acid. Preferably, the sequencing primer is complementary to a region of the template that is between the sequence to be characterized and the sequence hybridizable to the anchor primer. The sequencing primer is extended with the DNA polymerase to form a sequence product. The extension is performed in the presence of one or more types of nucleotide triphosphates, and if desired, auxiliary binding proteins.

Incorporation of the dNTP is preferably determined by assaying for the presence of a sequencing byproduct. In a preferred embodiment, the nucleotide sequence of the sequencing product is determined by measuring inorganic pyrophosphate (PPi) liberated from a nucleotide triphosphate (dNTP) as the dNMP is incorporated into an extended sequence primer. This method of sequencing, termed Pyrosequencing™ technology (PyroSequencing AB, Stockholm, Sweden) can be performed in solution (liquid phase) or as a solid phase technique. PPi-based sequencing methods are described generally in, e.g., WO9813523A1, Ronaghi, et al., 1996. Anal. Biochem. 242: 84-89, and Ronaghi, et al., 1998. Science 281: 363-365 (1998). These disclosures of PPi sequencing are incorporated herein in their entirety, by reference.

Pyrophosphate released under these conditions can be detected enzymatically (e.g., by the generation of light in the luciferase-luciferin reaction). Such methods enable a nucleotide to be identified in a given target position, and the DNA to be sequenced simply and rapidly while avoiding the need for electrophoresis and the use of potentially dangerous radiolabels.

PPi can be detected by a number of different methodologies, and various enzymatic methods have been previously described (see e.g., Reeves, et al., 1969. Anal. Biochem. 28: 282-287; Guillory, et al., 1971. Anal. Biochem. 39: 170-180; Johnson, et al., 1968. Anal. Biochem. 15: 273: Cook, et al., 1978. Anal Biochem. 91: 557-565; and Drake, et al., 1979. Anal. Biochem 94: 117-120).

PPi liberated as a result of incorporation of a dNTP by a polymerase can be converted to ATP using, e.g., an ATP sulfurylase. This enzyme has been identified as being involved in sulfur metabolism. Sulfur, in both reduced and oxidized forms, is an essential mineral nutrient for plant and animal growth (see e.g., Schmidt and Jager, 1992. Ann Rev. Plant Physiol. Plan Mol. Biol. 43: 325-349). In both plants and microorganisms, active uptake of sulfate is followed by reduction to sulfide. As sulfate has a very low oxidation/reduction potential relative to available cellular reductants, the primary step in assimilation requires its activation via an ATP-dependent reaction (see e.g., Leyh, 1993. Crit. Rev. Biochem. Mol. Biol 28: 515-542). ATP sulfurylase (ATP: sulfate adenylyltransferase; EC 2.7.7.4) catalyzes the initial reaction in the metabolism of inorganic sulfate ($SO_4^{-2}$); see e.g., Robbins and Lipmann, 1958. J. Biol. Chem 233: 686-690; Hawes and Nicholas, 1973. Biochem. J. 133: 541-550). In this reaction $SO_4^{-2}$ is activated to adenosine 5'-phosphosulfate (APS).

ATP sulfurylase has been highly purified from several sources, such as Saccharomyces cerevisiae (see e.g., Hawes and Nicholas, 1973. Biochem J. 133: 541-550); Penicillium chrysogenum (see e.g., Renosto, et al., 1990. J. Biol Chem 265: 10300-10308), rat liver (see e.g., Yu et al., 1989. Arch. Biochem. Biophys. 269. 165-174); and plants (see e.g., Shaw and Anderson. 1972. Biochem. J. 127: 237-247; Osslund, et al., 1982. Plant Physiol. 70: 39-45) Furthermore, ATP sulfurylase genes have been cloned from prokaryotes (see e.g., Leyh, et al., 1992. J Biol. Chem. 267: 10405-10410, Schwedock and Long, 1989. Mol. Plant Microbe Interaction 2: 181-194; Laue and Nelson, 1994. J. Bacteriol. 176: 3723-3729); eukaryotes (see e.g., Cherest, et al., 1987. Mol. Gen. Genet. 210: 307-313; Mountain and Korch, 1991. Yeast 7: 873-880; Foster, et al., 1994. J. Biol. Chem. 269: 19777-19786); plants (see e.g., Leustek, et al., 1994. Plant Physiol. 105: 897-90216); and animals (see e.g., Li, et al., 1995. J. Biol. Chem. 270: 29453-29459). The enzyme is a homooligomer or heterodimer, depending upon the specific source (see e.g., Leyh and Suo, 1992. J. Biol. Chem. 267: 542-545).

In some embodiments, a thermostable sulfurylase is used. Thermostable sulfurylases can be obtained from, e.g., Archaeoglobus or Pyrococcus spp. Sequences of thermostable sulfurylases are available at database Acc. No. 028606, Ace. No. Q9YCR4, and Acc. No. P56863.

ATP sulfurylase has been used for many different applications, for example, bioluminometric detection of ADP at high concentrations of ATP (see e.g., Schultz, et al., 1993. Anal. Biochem. 215: 302-304); continuous monitoring of DNA polymerase activity (see e.g., Nyrbn, 1987. Anal. Biochem. 167: 235-238); and DNA sequencing (see e.g., Ronaghi, et al., 1996. Anal. Biochem. 242: 84-89; Ronaghi, et al., 1998. Science 281: 363-365; Ronaghi, et al., 1998. Anal. Biochem. 267: 65-71).

Several assays have been developed for detection of the forward ATP sulfurylase reaction. The colorimetric molybdolysis assay is based on phosphate detection (see e.g., Wilson and Bandurski, 1958. J. Biol. Chem. 233: 975-981), whereas the continuous spectrophotometric molybdolysis assay is based upon the detection of NADH oxidation (see e.g., Seubert, et al., 1983. Arch. Biochem. Biophys. 225: 679-691; Seubert, et al., 1985. Arch. Biochem. Biophys. 240: 509-523). The later assay requires the presence of several detection enzymes. In addition, several radioactive assays have also been described in the literature (see e.g., Daley, et al., 1986. Anal. Biochem. 157: 385-395). For example, one assay is based upon the detection of $^{32}$PPi released from $^{32}$P-labeled ATP (see e.g., Seubert, et al., 1985. Arch. Biochem. Biophys 240: 509-523) and another on the incorporation of $^{35}$S into [$^{35}$S]-labeled APS (this assay also requires purified APS kinase as a coupling enzyme; see e.g, Seubert, et al., 1983. Arch Biochem. Biophys. 225: 679-691); and a third reaction depends upon the release of $^{35}SO_4^{-2}$ from [$^{35}$S]-labeled APS (see e.g., Daley, et al., 1986. Anal. Biochem. 157: 385-395).

For detection of the reversed ATP sulfurylase reaction a continuous spectrophotometric assay (see e.g., Segel, et al, 1987. Methods Enzymol. 143: 334-349); a bioluminometric assay (see e.g, Balharry and Nicholas, 1971. Anal. Biochem. 40: 1-17); an $^{35}SO_4^{-2}$ release assay (see e.g., Seubert, et al., 1985. Arch. Biochem. Biophys. 240: 509-523); and a $^{32}$PPi incorporation assay (see e.g., Osslund, et al., 1982. Plant Physiol. 70: 39-45) have been previously described.

ATP produced by an ATP sulfurylase can be hydrolyzed using enzymatic reactions to generate light. Light-emitting chemical reactions (i.e., chemiluminescence) and biological reactions (i.e., bioluminescence) are widely used in analytical biochemistry for sensitive measurements of various metabolites. In bioluminescent reactions, the chemical reaction that leads to the emission of light is enzyme-catalyzed. For example, the luciferin-luciferase system allows for specific assay of ATP and the bacterial luciferase-oxidoreductase system can be used for monitoring of NAD(P)H. Both systems have been extended to the analysis of numerous substances by means of coupled reactions involving the production or utilization of ATP or NAD(P)H (see e.g., Kricka, 1991. Chemiluminescent and bioluminescent techniques. *Clin. Chem.* 37: 1472-1281).

The development of new reagents have made it possible to obtain stable light emission proportional to the concentrations of ATP (see e.g., Lundin, 1982. Applications of firefly luciferase In; *Luminescent Assays* (Raven Press, New York) or NAD(P)H (see e.g., Lovgren, et al., Continuous monitoring of NADH-converting reactions by bacterial luminescence. *J. Appl. Biochem.* 4: 103-111). With such stable light emission reagents, it is possible to make end-point assays and to calibrate each individual assay by addition of a known amount of ATP or NAD(P)H. In addition, a stable light-emitting system also allows continuous monitoring of ATP- or NAD(P)H-converting systems.

Suitable enzymes for converting ATP into light include luciferases, e.g., insect luciferases. Luciferases produce light as an end-product of catalysis. The best known light-emitting enzyme is that of the firefly, *Photinus pyralis* (*Coleoptera*). The corresponding gene has been cloned and expressed in bacteria (see e.g., de Wet, et al., 1985. *Proc Natl Acad. Sci. USA* 80: 7870-7873) and plants (see e.g, Ow, et al, 1986. *Science* 234: 856-859), as well as in insect (see e.g. Jha, et al., 1990. *FEBS Lett.* 274: 24-26) and mammalian cells (see e.g., de Wet, et al. 1987. *Mol Cell. Biol.* 7: 725-7373; Keller, et al., 1987. *Proc Natl Acad. Sci. USA* 82: 3264-3268). In addition, a number of luciferase genes from the Jamaican click beetle, *Pyroplorus plagiophihalamus* (*Coleoptera*), have recently been cloned and partially characterized (see e.g. Wood, et al., 1989. *J. Biolumin. Chemilumin.* 4: 289-301; Wood, et al, 1989. *Science* 244: 700-702). Distinct luciferases can sometimes produce light of different wavelengths, which may enable simultaneous monitoring of light emissions at different wavelengths. Accordingly, these aforementioned characteristics are unique, and add new dimensions with respect to the utilization of current reporter systems.

Firefly luciferase catalyzes bioluminescence in the presence of luciferin, adenosine 5'-triphosphate (ATP), magnesium ions, and oxygen, resulting in a quantum yield of 0.88 (see e.g., McElroy and Selinger, 1960. *Arch. Biochem. Biophys.* 88: 136-145). The firefly luciferase bioluminescent reaction can be utilized as an assay for the detection of ATP with a detection limit of approximately $1\times10^{-13}$ M (see e.g., Leach, 1981. *J. Appl. Biochem.* 3: 473-517). In addition, the overall degree of sensitivity and convenience of the luciferase-mediated detection systems have created considerable interest in the development of firefly luciferase-based biosensors (see e.g., Green and Kricka, 1984. *Talanta* 31: 173-176; Blum, et al., 1989. *J. Biolumin. Chemilumin.* 4: 543-550).

Using the above-described enzymes, the sequence primer is exposed to a polymerase and a known dNTP. If the dNTP is incorporated onto the 3' end of the primer sequence, the dNTP is cleaved and a PPi molecule is liberated. The PPi is then converted to ATP with ATP sulfurylase. Preferably, the ATP sulfurylase is present at a sufficiently high concentration that the conversion of PPi proceeds with first-order kinetics with respect to PPi. In the presence of luciferase, the ATP is hydrolyzed to generate a photon. The reaction preferably has a sufficient concentration of luciferase present within the reaction mixture such that the reaction, $ATP \rightarrow ADP + PO_4^{3-} + $ photon (light), proceeds with first-order kinetics with respect to ATP. The photon can be measured using methods and apparatuses described below. In one embodiment, the PPi and a coupled sulfurylase/luciferase reaction is used to generate light for detection. In some embodiments, either or both the sulfurylase and luciferase are immobilized on one or more mobile solid supports disposed at each reaction site.

The present invention thus permits PPi release to be detected during the polymerase reaction giving a real-time signal. The sequencing reactions may be continuously monitored in real-time. A procedure for rapid detection of PPi release is thus enabled by the present invention. The reactions have been estimated to take place in less than 2 seconds (Nyren and Lundin, supra). The rate limiting step is the conversion of PPi to ATP by ATP sulfurylase, while the luciferase reaction is fast and has been estimated to take less than 0.2 seconds Incorporation rates for polymerases have also been estimated by various methods and it has been found, for example, that in the case of Klenow polymerase, complete incorporation of one base may take less than 0.5 seconds. Thus, the estimated total time for incorporation of one base and detection by this enzymatic assay is approximately 3 seconds. It will be seen therefore that very fast reaction times are possible, enabling real-time detection. The reaction times could further be decreased by using a more thermostable luciferase.

For most applications it is desirable to use reagents free of contaminants like ATP and PPi. These contaminants may be removed by flowing the reagents through a pre-column containing apyrase and/-or pyrophosphatase bound to resin. Alternatively, the apyrase or pyrophosphatase can be bound to magnetic beads and used to remove contaminating ATP and PPi present in the reagents. In addition it is desirable to wash away diffusible sequencing reagents, e.g., unincorporated dNTPs, with a wash buffer. Any wash buffer used in pyrophosphate sequencing can be used.

In some embodiments, the concentration of reactants in the sequencing reaction include 1 pmol DNA, 3 pmol polymerase, 40 pmol dNTP in 0.2 ml buffer. See Ronaghi, et al., *Anal. Biochem.* 242: 84-89 (1996).

The sequencing reaction can be performed with each of four predetermined nucleotides, if desired. A "complete" cycle generally includes sequentially administering sequencing reagents for each of the nucleotides dATP, dGTP, dCTP and dTTP (or dUTP), in a predetermined order. Unincorporated dNTPs are washed away between each of the nucleotide additions. Alternatively, unincorporated dNTPs are degraded by apyrase (see below). The cycle is repeated as desired until the desired amount of sequence of the sequence product is obtained. In some embodiments, about 10-1000, 10-100, 10-75, 20-50, or about 30 nucleotides of sequence information is obtained from extension of one annealed sequencing primer.

In some embodiments, the nucleotide is modified to contain a disulfide-derivative of a hapten such as biotin. The addition of the modified nucleotide to the nascent primer annealed to the anchored substrate is analyzed by a post-polymerization step that includes i) sequentially binding of, in the example where the modification is a biotin, an avidin- or streptavidin-conjugated moiety linked to an enzyme molecule, ii) the washing away of excess avidin- or streptavidin-linked enzyme, iii) the flow of a suitable enzyme substrate under conditions amenable to enzyme activity, and iv) the detection of enzyme substrate reaction product or products. The hapten is removed in this embodiment through the addition of a reducing agent. Such methods enable a nucleotide to be identified in a given target position, and the DNA to be sequenced simply and rapidly while avoiding the need for electrophoresis and the use of potentially dangerous radiolabels.

A preferred enzyme for detecting the hapten is horseradish peroxidase. If desired, a wash buffer, can be used between the addition of various reactants herein. Apyrase can be used to remove unreacted dNTP used to extend the sequencing primer. The wash buffer can optionally include apyrase.

Example haptens, e.g., biotin, digoxygenin, the fluorescent dye molecules cy3 and cy5, and fluorescein, are incorporated at various efficiencies into extended DNA molecules. The attachment of the hapten can occur through linkages via the sugar, the base, and via the phosphate moiety on the nucleotide. Example means for signal amplification include fluorescent, electrochemical and enzymatic. In a preferred embodiment using enzymatic amplification, the enzyme, e.g. alkaline phosphatase (AP), horse-radish peroxidase (HRP), beta-galactosidase, luciferase, can include those for which light-generating substrates are known, and the means for detection of these light-generating (chemiluminescent) substrates can include a CCD camera.

In a preferred mode, the modified base is added, detection occurs, and the hapten-conjugated moiety is removed or inactivated by use of either a cleaving or inactivating agent For example, if the cleavable-linker is a disulfide, then the cleaving agent can be a reducing agent, for example dithiothreitol (DTT), beta-mercaptoethanol, etc. Other embodiments of inactivation include heat, cold, chemical denaturants, surfactants, hydrophobic reagents, and suicide inhibitors.

Luciferase can hydrolyze dATP directly with concomitant release of a photon. This results in a false positive signal because the hydrolysis occurs independent of incorporation of the dATP into the extended sequencing primer. To avoid this problem, a dATP analog can be used which is incorporated into DNA, i.e., it is a substrate for a DNA polymerase, but is not a substrate for luciferase. One such analog is α-thio-dATP. Thus, use of α-thio-dATP avoids the spurious photon generation that can occur when dATP is hydrolyzed without being incorporated into a growing nucleic acid chain.

Typically, the PPi-based detection is calibrated by the measurement of the light released following the addition of control nucleotides to the sequencing reaction mixture immediately after the addition of the sequencing primer. This allows for normalization of the reaction conditions. Incorporation of two or more identical nucleotides in succession is revealed by a corresponding increase in the amount of light released. Thus, a two-fold increase in released light relative to control nucleotides reveals the incorporation of two successive dNTPs into the extended primer.

If desired, apyrase may be "washed" or "flowed" over the surface of the solid support so as to facilitate the degradation of any remaining, non-incorporated dNTPs within the sequencing reaction mixture. Apyrase also degrades the generated ATP and hence "turns off" the light generated from the reaction. Upon treatment with apyrase, any remaining reactants are washed away in preparation for the following dNTP incubation and photon detection steps. Alternatively, the apyrase may be bound to the solid or mobile solid support.

When the support is planar, the pyrophosphate sequencing reactions preferably take place in a thin reaction chamber that includes one optically transparent solid support surface and an optically transparent cover. In some embodiments, the array has a planar top surface and a planar bottom surface, the planar top surface has at least 1,000 cavities thereon each cavity forming a reaction chamber. In additional embodiments, the planar bottom surface is optically conductive such that optical signals from the reaction chambers can be detected through the bottom planar surface. In a preferred embodiment, the distance between the top surface and the bottom surface is no greater than 10 cm. Sequencing reagents may then be delivered by flowing them across the surface of the substrate. More preferably, the cavities contain reagents for analyzing a nucleic acid or protein. In an additional embodiment, the array has a second surface spaced apart from the planar array and in opposing contact therewith such that a flow chamber is formed over the array. When the support is not planar, the reagents may be delivered by dipping the solid support into baths of any given reagents.

In a preferred embodiment, an array can be used to carry out separate parallel common reactions in an aqueous environment. The array can have a substrate having at least 1,000 discrete reaction chambers containing a starting material that is capable of reacting with a reagent, each of the reaction chambers being dimensioned such that when one or more fluids containing at least one reagent is delivered into each reaction chamber, the diffusion time for the reagent to diffuse out of the well exceeds the time required for the starting material to react with the reagent to form a product. The reaction chambers can be formed by generating a plurality of cavities on the substrate. The plurality of cavities can be formed in the substrate via etching, molding or micromaching. The cavities can have a planar bottom or a concave bottom. In a preferred embodiment, the substrate is a fiber optic bundle. In an additional embodiment, the reaction chambers are formed by generating discrete patches on a planar surface. The patches can have a different surface chemistry than the surrounding planar surface.

In various embodiments, some components of the reaction are immobilized, while other components are provided in solution. For example, in some embodiments, the enzymes utilized in the pyrophosphate sequencing reaction (e.g., sulfurylase, luciferase) may be immobilized if desired onto the solid support. Similarly, one or more or of the enzymes utilized in the pyrophosphate sequencing reaction, e.g., sulfurylase, luciferase may be immobilized at the termini of a fiber optic reactor array. When luciferase is immobilized, it is preferably less than 50 µm from an anchored primer. Other components of the reaction, e.g., a polymerase (such as Klenow fragment), nucleic acid template, and nucleotides can be added by flowing, spraying, or rolling. In still further embodiments, one more of the reagents used in the sequencing reactions is delivered on beads.

In some embodiments, reagents are dispensed using an expandable, flexible membrane to dispense reagents and seal reactors on FORA surface during extension reactions. Reagents can be sprayed or rolled onto either the FORA surface or onto the flexible membrane. The flexible membrane could then be either rapidly expanded or physically moved into close proximity with the FORA thereby sealing the wells such that PPi would be unable to diffuse from well to well. Preferably, data acquisition takes place at a reasonable time after reaction initiation to allow maximal signal to generate.

A sequence in an extended anchor primer can also be identified using sequencing methods other than by detecting a sequence byproduct. For example, sequencing can be performed by measuring incorporation of labeled nucleotides or other nucleotide analogs.

These methods can be used in conjunction with fluorescent or electrochemiluminescent-based methods.

Alternatively, sequence byproducts can be generated using dideoxynucleotides having a label on the 3' carbon. Preferably, the label can be cleaved to reveal a 3' hydroxyl group. In this method, addition of a given nucleotide is scored as positive or negative, and one base is determined at each trial. In this embodiment, solid phase enzymes are not required and multiple measurements can be made.

In another embodiment, the identity of the extended anchor primer product is determined using labeled deoxynucleotides. The labeled deoxynucleotides can be, e.g., fluorescent nucleotides. Preferably the fluorescent nucleotides can be detected following laser-irradiation. Preferably, the fluorescent label is not stable for long periods of exposure. If desired, the fluorescent signal can be quenched, e.g., photobleached, to return signal to background levels prior to addition of the next base. A preferred electrochemiluminescent label is ruthenium-tris-bi-pyridyl.

In one embodiment, a single stranded circular nucleic acid is immobilized in the reaction chamber; preferably each reaction chamber has no more than one single stranded circular nucleic acid disposed therein. More preferably, a single stranded circular nucleic acid is immobilized on a mobile solid support disposed in the reaction chamber. In another embodiment, each single stranded circular nucleic acid contains at least 100 copies of a nucleic acid sequence, each copy covalently linked end to end.

The invention also comprises kits for use in methods of the invention which could include one or more of the following components: (a) a test specific primer which hybridizes to sample DNA so that the target position is directly adjacent to the 3' end of the primer; (b) a polymerase; (c) detection enzyme means for identifying PPi release; (d) deoxynucleotides including, in place of dATP, a dATP analogue which is capable of acting as a substrate for a polymerase but incapable of acting as a substrate for a said PPi-detection enzyme; and (e) optionally dideoxynucleotides optionally ddATP being replaced by a ddATP analogue which is capable of acting as a substrate for a polymerase but incapable of acting as a substrate for a said PPi-detection enzyme. If the kit is for use with initial PCR amplification then it could also include the following components: (i) a pair of primers for PCR, at least one primer having means permitting immobilization of said primer; (ii) a polymerase which is preferably heat stable, for example Taq 1 polymerase; (iii) buffers for the PCR reaction; and (iv) deoxynucleotides. Where an enzyme label is used to evaluate PCR, the kit will advantageously contain a substrate for the enzyme and other components of a detection system.

Mathematical Analysis Underlying Optimization of the Pyrophosphate Sequencing Reaction While not wishing to be bound by theory, it is believed that optimization of reaction conditions can be performed using assumptions underlying the following analyses.

Solid phase pyrophosphate sequencing was initially developed by combining a solid-phase technology and a sequencing-by-synthesis technique utilizing bioluminescence (see e.g, Ronaghi, et al, 1996. Real-time DNA sequencing using detection of pyrophosphate release. *Anal. Biochem.* 242: 84-89). In the solid-phase methodology, an immobilized, primed DNA strand is incubated with DNA polymerase, ATP sulfurylase, and luciferase. By stepwise nucleotide addition with intermediate washings the event of sequential polymerization can be followed. The signal-to-noise ratio was increased by the use of α-thio dATP in the system. This dATP analog is efficiently incorporated by DNA polymerase but does not serve as a substrate for luciferase. This reduces background bioluminescence and facilitates performance of the sequencing reaction in real-time. In these early studies, sequencing of a PCR product using streptavidin-coated magnetic beads as a solid support was presented. However, it was found that the loss of the beads during washing, which was performed between each nucleotide and enzyme addition, limited the technique to short sequences.

Currently, pyrophosphate sequencing methodologies have a reasonably well-established history for ascertaining the DNA sequence from many identical copies of a single DNA sequencing template (see e.g., Ronaghi, et al., 1996. Real-Time DNA Sequencing Using Detection of Pyrophosphate Release, *Anal. Biochem.* 242: 84-89; Nyrén, et al., Method of Sequencing DNA, patent WO9813523A1 (issued Apr. 2, 1998; filed Sep. 26, 1997); Ronaghi, et al., 1998. A Sequencing Method Based on Real-Time Pyrophosphate *Science* 281: 363-365 (1998). Pyrophosphate (PPi)-producing reactions can be monitored by a very sensitive technique based on bioluminescence (see e.g., Nyrén, et al., 1996. pp.466-496 (*Proc. 9$^{th}$ Inter. Symp. Biolumin. Chemilumin.*). These bioluminometric assays rely upon the detection of the PPi released in the different nucleic acid-modifying reactions. In these assays, the PPi which is generated is subsequently converted to ATP by ATP sulfurylase and the ATP production is continuously monitored by luciferase. For example, in polymerase-mediated reactions, the PPi is generated when a nucleotide is incorporated into a growing nucleic acid chain being synthesized by the polymerase. While generally, a DNA polymerase is utilized to generate PPi during a pyrophosphate sequencing reaction (see e.g., Ronaghi, et al., 1998. *Doctoral Dissertation,* The Royal Institute of Technology, Dept. of Biochemistry (Stockholm, Sweden)), it is also possible to use reverse transcriptase (see e.g., Karamohamamed, et al., 1996. pp. 319-329 (*Proc. 9$^{th}$ Inter. Symp. Biolumin. Chemilumin.*) or RNA polymerase (see e.g, Karamohamamed, et al, 1998. *BioTechniques* 24: 302-306) to follow the polymerization event.

For example, a bioluminometric primer extension assay has been utilized to examine single nucleotide mismatches at the 3'-terminus (see e.g, Nyrén, et al, 1997. *Anal Biochem* 244:367-373). A phage promoter is typically attached onto at least one of the arbitrary primers and following amplification, a transcriptional unit may be obtained which can then be subjected to stepwise extension by RNA polymerase. The transcription-mediated PPi-release can then be detected by a bioluminometric assay (e.g., ATP sulfurylase-luciferase). By using this strategy, it is likely to be possible to sequence double-stranded DNA without any additional specific sequencing primer. In a series of "run-off" assays, the extension by T7 phage RNA polymerase has been examined and was found to be rather slow (see e.g., Kwok, et al., 1990. *Nucl Acids Res.* 18: 999-1005). The substitution of an α-thio nucleotide analogs for the subsequent, correct natural deoxynucleotide after the 3'-mismatch termini, could decrease the rate of polymerization by 5-fold to 13-fold. However, after incorporation of a few bases, the rate of DNA synthesis is comparable with the rate observed for a normal template/primer.

Single-base detection by this technique has been improved by incorporation of apyrase to the system, which catalyzes NTP hydrolysis and reduces the nucleotide concentration far below the $K_m$ of DNA polymerase, effectively removing dNTP from a preceding step before proceeding to addition of the subsequent dNTP. The above-described technique provides a rapid and real-time analysis for applications in the areas of mutation detection and single-nucleotide polymorphism (SNP) analysis.

The pyrophosphate sequencing system uses reactions catalyzed sequentially by several enzymes to monitor DNA synthesis. Enzyme properties such as stability, specificity, sensitivity. $K_M$ and $k_{CAT}$ are important for the optimal performance of the system. In the pyrophosphate sequencing system, the activity of the detection enzymes (i.e., sulfurylase and luciferase) generally remain constant during the sequencing reaction, and are only very slightly inhibited by high amounts of products (see e.g., Ronaghi, et al., 1998. *Doctoral Dissertation,* The Royal Institute of Technology, Dept. of Biochemistry (Stockholm, Sweden)). Sulfurylase converts each PPi to ATP in approximately 2.0 seconds (see e.g., Nyrén and Lundin, 1985. *Anal. Biochem.* 151: 504-509). The reported reaction conditions for 1 pmol PPi in 0.2 ml buffer (5 nM) are 0.3 U/ml ATP sulfurylase (ATP:sulfate adenylyltransferase; Prod. No. A8957; Sigma Chemical Co., St. Louis, Mo.) and 5 µM APS (see e.g, Ronaghi, et al., 1996. Real-Time DNA Sequencing Using Detection of Pyrophosphate Release, *Anal Biochem* 242: 84-89). The manufacturer's information (Sigma Chemical Co., St. Louis, Mo.) for sulfurylase reports an activity of 5-20 units per mg protein (i.e., one unit will produce 1.0 µmole of ATP from APS and PPi per minute at pH 8.0 at 30 C), whereas the specific activity has been reported elsewhere as 140 units per mg (see Karamohamed, et al., 1999 Purification, and Luminometric Analysis of Recombinant *Saccharomyces cerevisiae* MET3 Adenosine Triphosphate Sulfurylase Expressed in *Escherichia coli. Prot. Express. Purification* 15: 381-388). Due to the fact that the reaction conditions utilized in the practice of the present invention are similar to those reaction conditions reported in the aforementioned reference, the sulfurylase concentration within the assay was estimated as 4.6 nM. The $K_M$ values for sulfurylase are [APS]=0.5 µM and [PPi]=7 µM. The generation of light by luciferase takes place in less than 0.2 seconds. The most critical reactions are the DNA polymerization and the degradation of nucleotides. The value of constants characterizing the enzymes utilized in the pyrophosphate sequencing methodology are listed below for reference:

| Enzyme | $K_M$ (µM) | $k_{CAT}$ (S$^{-1}$) |
|---|---|---|
| Klenow | 0.18 (dTTP) | 0.92 |
| T$_7$ DNA Polymerase | 0.36 (dTTP) | 0.52 |
| ATP Sulfurylase | 0.56 (APS); 7.0 (PPi) | 38 |
| Firefly Luciferase | 20 (ATP) | 0.015 |
| Apyrase | 120 (ATP); 200 (ADP) | 500 (ATP) |

The enzymes involved in these four reactions compete for the same substrates Therefore, changes in substrate concentrations are coupled. The initial reaction is the binding of a dNTP to a polymerase/DNA complex for chain elongation. For this step to be rapid, the nucleotide triphosphate concentration must be above the $K_M$ of the DNA polymerase. If the concentration of the nucleotide triphosphates is too high, however, lower fidelity of the polymerase may be observed (see e.g., Cline, et al., 1996. PCR fidelity of Pfu DNA polymerase and other thermostable DNA polymerases. *Nucl. Acids Res.* 24: 3546-3551). A suitable range of concentrations is established by the $K_M$ for the misincorporation, which is usually much higher (see e.g., Capson, et al., 1992. Kinetic characterization of the polymerase and exonuclease activity of the gene 43 protein of bacteriophage T4. *Biochemistry* 31: 10984-10994). Although a very high fidelity can be achieved by using polymerases with inherent exonuclease activity, their use also holds the disadvantage that primer degradation may occur.

Although the exonuclease activity of the Klenow fragment of DNA polymerase I (Klenow) is low, it has been demonstrated that the 3'-terminus of a primer may be degraded with longer incubations in the absence of nucleotide triphosphates (see e.g, Ronaghi, et al, 1998. *Doctoral Dissertation,* The Royal Institute of Technology, Dept. of Biochemistry (Stockholm, Sweden)). Fidelity is maintained without exonuclease activity because an induced-fit binding mechanism in the polymerization step provides a very efficient selectivity for the correct dNTP. Fidelities of $1 \times 10^5$ to $1 \times 10^6$ have been reported (see e.g., Wong, et al, 1991. An induced-fit kinetic mechanism for DNA replication fidelity *Biochemistry* 30: 526-537). In pyrophosphate sequencing, exonuclease-deficient (exo-) polymerases, such as exo-Klenow or Sequenase®, have been confirmed to have high fidelity.

Estimates for the spatial and temporal constraints on the pyrophosphate sequencing methodology of the present invention have been calculated, wherein the system possesses a 1 cm$^2$ area with height approximately 50 µm, for a total volume of 5 µl. With respect to temporal constraints, the molecular species participating in the cascade of reactions are initially defined, wherein:

N=the DNA attached to the surface
PPi=the pyrophosphate molecule released
ATP=the ATP generated from the pyrophosphate
L=the light released by luciferase It is further specified that N(0) is the DNA with no nucleotides added, N(1) has 1 nucleotide added, N(2) has 2 nucleotides added, and so on. The pseudo-first-order rate constants which relate the concentrations of molecular species are:

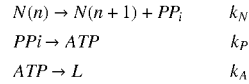

$$N(n) \to N(n+1) + PP_i \quad k_N$$
$$PPi \to ATP \quad k_P$$
$$ATP \to L \quad k_A$$

In addition, the diffusion constants $D_P$ for PPi and $D_A$ for ATP must also be specified. These values may be estimated from the following exemplar diffusion constants for biomolecules in a dilute water solution (see Weisiger, 1997. Impact of Extracellular and Intracellular Diffusion on Hepatic Uptake Kinetics).

| Molecule | D/10$^{-5}$ cm$^2$/sec | Method | Original Reference |
|---|---|---|---|
| Albumin | 0.066 | lag time | 1 |
| Albumin | 0.088 | light scattering | 2 |
| Water | 1.940 | NMR | 3 | wherein, Original Reference 1 is: Longsworth, 1954. Temperature dependence of diffusion in aqueous solutions, *J. Phys. Chem.* 58: 770-773; Original Reference 2 is: Gaigalas, et al., 1992. Diffusion of bovine serum albumin in aqueous solutions, *J. Phys. Chem.* 96: 2355-2359; and Original Reference 3 is: Cheng, 1993. Quantitation of non-Einstein diffusion behavior of water in biological tissues by proton NMR diffusion imaging: Synthetic image calculations, *Magnet. Reson. Imaging* 11: 569-583.

In order to estimate the diffusion constant of PPi, the following exemplar values may be utilized (see *CRC Handbook of Chemistry and Physics*, 1983. (W. E. Weast. Ed.) CRC Press, Inc., Boca Raton, Fla.):

| Molecule | $D/10^{-5}$ cm$^2$/sec | Molecular Weight/amu |
|---|---|---|
| sucrose | 0.5226 | 342.30 |
| mannitol | 0.682 | 182.18 |
| penta-erythritol | 0.761 | 136.15 |
| glycolamide | 1.142 | N/A |
| glycine | 1.064 | 75.07 |

The molecular weight of PPi is 174 amu. Based upon the aforementioned exemplar values, a diffusion constant of approximately $0.7 \times 10^{-5}$ cm$^2$/sec for PPi is expected.

Enzymes catalyzing the three pyrophosphate sequencing reactions are thought to approximate Michaelis-Menten kinetics (see e.g. Stryer, 1988. *Biochemistry*, W. H. Freeman and Company, New York), which may be described:

$$K_M = [E][S]/[ES],$$

$$\text{velocity} = V_{max}[S]/(K_M + [S]),$$

$$V_{max} = k_{CAT}[E_T]$$

where [S] is the concentration of substrate, [E] is the concentration of free enzyme, [ES] is the concentration of the enzyme-substrate complex, and [$E_T$] is the total concentration of enzyme=[E]+[ES].

It is preferable that the reaction times are at least as fast as the solution-phase pyrophosphate-based sequencing described in the literature. That rate that a substrate is converted into product is $$-d[S]/dt = k_{CAT}[E_T][S]/(K_M+[S])$$

The effective concentration of substrate may be estimated from the size of a replicated DNA molecule, at most (10 μm)$^3$ and the number of copies (approximately 10,000), yielding a concentration of approximately 17 nM. This is smaller than the $K_M$ for the enzymes described previously, and therefore the rate can be estimated to be $$-d[S]/dt = (k_{CAT}/K_M)[E_T][S].$$

Thus, with pseudo first-order kinetics, the rate constant for disappearance of substrate depends on $k_{CAT}$ and $K_M$, which are constants for a given enzyme, and [$E_T$]. Using the same enzyme concentrations reported in the literature will therefore produce similar rates.

The first step in the pyrophosphate sequencing reaction (i.e., incorporation of a new nucleotide and release of PPi) will now be examined in detail. The preferred reaction conditions are: 1 pmol DNA, 3 pmol polymerase, 40 pmol dNTP in 0.2 ml buffer. Under the aforementioned, preferred reaction conditions, the $K_M$ for nucleotide incorporation for the Klenow fragment of DNA polymerase 1 is 0.2 μM and for Sequenase 2.0™ (US Biochemicals, Cleveland, Ohio) is 0.4 μM, and complete-incorporation of 1 base is less than 0.2 see (see e.g., Ronaghi, et al., 1996. Real-Time DNA Sequencing Using Detection of Pyrophosphate Release, *Anal. Biochem.* 242: 84-89) with a polymerase concentration of 15 nM.

In a 5 μl reaction volume, there are a total of 10,000 anchor primers with 10,000 sequencing primer sites each, or $1 \times 10^8$ total extension sites=0.17 fmol. Results which have been previously published in the literature suggest that polymerase should be present at 3-times abundance, or 0.5 fmol, within the reaction mixture. The final concentration of polymerase is then 0.1 nM. It should be noted that these reaction conditions are readily obtained in the practice of the present invention.

As previously stated, the time required for the nucleotide addition reaction is no greater than 0.2 sec per nucleotide. Hence if the reaction is allowed to proceed for a total of T seconds, then nucleotide addition should be sufficiently rapid that stretches of up to (T/0.2) identical nucleotides should be completely filled-in by the action of the polymerase. As discussed previously, the rate-limiting step of the pyrophosphate sequencing reaction is the sulfurylase reaction, which requires a total of approximately 2 sec to convert one PPi to ATP. Accordingly, a total reaction time which allows completion of the sulfurylase reaction, should be sufficient to allow the polymerase to "fill-in" stretches of up to 10 identical nucleotides. In random DNA species, regions of 10 or more identical nucleotides have been demonstrated to occur with a per-nucleotide probability of approximately $4^{-10}$, which is approximately $1 \times 10^{-6}$. In the 10,000 sequences which are extended from anchor primers in a preferred embodiment of the present invention, each of which will be extended at least 30 nucleotides and preferably 100 nucleotides, it is expected that approximately one run of 10 identical nucleotides will be present. Thus, it may be concluded that runs of identical nucleotides should not pose a difficulty in the practice of the present invention.

The overall size of the resulting DNA molecule is, preferably, smaller than the size of the anchoring pads (i.e., 10 μm) and must be smaller than the distance between the individual anchoring pads (i.e., 100 μm). The radius of gyration of a single-stranded DNA concatamer with N total nucleotides may be mathematically-estimated by the following equation: radius=$b(N/N_0)^{0.6}$, where b is the persistence length and $N_0$ is the number of nucleotides per persistence length; the exponent 0.6 is characteristic of a self-avoiding walk (see e.g., Doi, 1986. *The Theory of Polymer Dynamics* (Clarendon Press, New York); Flory, 1953. *Principles of Polymer Chemistry* (Cornell University Press, New York)). Using single-stranded DNA as an example, b is 4 nm and $N_0$ is 13.6 nucleotides. (see e.g., Grosberg, 1994. *Statistical Physics of Macromolecules* (AIP Press, New York)). Using 10,000 copies of a 100-mer, $N=1 \times 10^6$ and the radius of gyration is 3.3 μm.

The diffusion of PPi will now be discussed in detail. In the reaction conditions utilized in the present invention, [$PP_i$] is approximately 0.17 fmol in 5 μl, or 0.03 nM, and [sulfurylase] is 4.6 nM as described previously. In the first 2 sec of the reaction, about 7% (0.002 nM) of PPi is consumed by sulfurylase, using GEPASI simulation software (see Mendes, P. (1993) GEPASI: a software package for modeling the dynamics, steady states and control of biochemical and other systems. Comput. Appl. Biosci. 9,563-571.). The parameters used in simulation were $K_M$(PPi)=7 μM, $k_{CAT}$=38 s$^{-1}$, and [sulfurylase]=4.6 nM. Therefore, it may be concluded that at least 93% of PPi molecules may diffuse away before being converted to ATP during the 2 sec reaction time.

The mean time for each PPi to react is $1/k_P$=2 seconds. The mean square distance it diffuses in each direction is approximately $2D_P/k_P$, or $2.8 \times 10^3$ μm$^2$. The RMS distance in each direction is 53 μm. This value indicates that each of the individual anchor primers must be more than 50 µm apart, or PPi which is released from one anchor could diffuse to the next, and be detected.

Another method which may be used to explain the aforementioned phenomenon is to estimate the amount of PPi over a first anchor pad that was generated at said first anchor pad relative to the amount of PPi that was generated at a second anchor pad and subsequently diffused over to the location of said first anchor pad. When these two quantities approach each other in magnitude, it becomes difficult to distinguish the "true" signal from that of the background. This may be mathematically-described by defining a as the radius of an anchor pad and $1/b^2$ as the density of an anchor pad. Based upon previously published data, a is approximately equal to 10 µm and b is approximately equal to 100 µm. The amount of PPi which is present over said first anchor pad may be described by: $\exp(-k_P t)[1-\exp(-a^2/2D_P t)]$ and the amount of PPi present over the second anchor pads may be mathematically approximated by:

$(1/3)\exp(-k_P t)[pa^2/b^2]\exp(-b^2/2D_P t)$. The prefactor 1/3 assumes that ¼ of the DNA sequences will incorporate 1 nucleotide, ¼ of these will then incorporate a second nucleotide, etc., and thus the sum of the series is 1/3. The amounts of PPi over the first and second anchor pads become similar in magnitude when $2D_P t$ is approximately equal to $b^2$, thus indicating that the RMS distance a molecule diffuses is equal to the distance between adjacent anchor pads. In accord, based upon the assay conditions utilized in the practice of the present invention, the anchor pads must be placed no closer than approximately 50 µm apart, and preferable are at least 3-times further apart (i.e., 150 µm).

Although the aforementioned findings set a limit on the surface density of anchor pads, it is possible to decrease the distance requirements, while concomitantly increasing the overall surface density of the anchor pads, by the use of a number of different approaches. One approach is to detect only the early light, although this has the disadvantage of losing signal, particularly from DNA sequences which possess a number of contiguous, identical nucleotides.

A second approach to decrease the distance between anchor pads is to increase the concentration of sulfurylase in the reaction mixture. The reaction rate $k_P$, is directly proportional to the sulfurylase concentration, and the diffusion distance scales as $k_P^{-1/2}$. Therefore, if the sulfurylase enzyme concentration is increased by a factor of 4-times, the distance between individual anchor pads may be concomitantly reduced by a factor of 2-times.

A third approach is to increase the effective concentration of sulfurylase (which will also work for other enzymes described herein) by binding the enzyme to the surface of the anchor pads. The anchor pad can be approximated as one wall of a cubic surface enclosing a sequencing reaction center. Assuming a 10 µm×10 µm surface for the pad, the number of molecules bound to the pad to produce a concentration of a 1 µM is approximately 600,000 molecules.

The sulfurylase concentration in the assay is estimated as 5 nM. The number of bound molecules to reach this effective concentration is about 3000 molecules. Thus, by binding more enzyme molecules, a greater effective concentration will be attained. For example, 10,000 molecules could be bound per anchor pad.

As previously estimated, each sulfurylase molecule occupies a total area of 65 nm² on a surface. Accordingly, anchoring a total of 10,000 sulfurylase enzyme molecules on a surface (i.e., so as to equal the 10,000 PPi released) would require 1.7 µm². This value is only approximately 2% of the available surface area on a 10 µm×10 µm anchor pad. Hence, the concentration of the enzyme may be readily increased to a much higher value.

A fourth approach to allow a decrease in the distance between individual anchor pads, is to utilize one or more agents to increase the viscosity of the aqueous-based, pyrophosphate sequencing reagents (e.g., glycerol, polyethylene glycol (PEG), and the like) so as to markedly increase the time it takes for the PPi to diffuse. However, these agents will also concomitantly increase the diffusion time for other non-immobilized components within the sequencing reaction, thus slowing the overall reaction kinetics. Additionally the use of these agents may also function to chemically-interfere with the sequencing reaction itself.

A fifth, and preferred, methodology to allow a decrease in the distance between individual anchor pads, is to conduct the pyrophosphate sequencing reaction in a spatial-geometry which physically-prevents the released PPi from diffusing laterally. For example, uniform cavities or microwells, such as those generated by acid-etching the termini of optical fiber bundles, may be utilized to prevent such lateral diffusion of PPi (see Michael, et al., 1998. Randomly Ordered Addressable High-Density Optical Sensor Arrays, *Anal. Chem.* 70: 1242-1248). In this embodiment, the important variable involves the total diffusion time for the PPi to exit a cavity of height h, wherein h is the depth of the etched cavity. This diffusion time may be calculated utilizing the equation: $2D_P t=h^2$. By use of the preferred pyrophosphate sequencing reaction conditions of the present invention in the aforementioned calculations, it may be demonstrated that a cavity 50 µm in depth would be required for the sequencing reaction to proceed to completion before complete diffusion of the PPi from said cavity. Moreover, this type of geometry has the additional advantage of concomitantly reducing background signal from the PPi released from adjacent anchor pads.

Additionally, to prevent background generated by diffusion of PPi from one pad to another, the region of substrate between the pads can be coated with immobilized phosphatase.

Subsequently, once ATP has been formed by use of the preferred reaction conditions of the present invention, the reaction time, $1/k_A$, has been shown to be 0.2 seconds. Because this reaction time is much lower than the time which the PPi is free to diffuse, it does not significantly alter any of the aforementioned conclusions regarding the assay geometry and conditions utilized in the present invention.

In order to mitigate the generation of background light, it is preferable to "localize" (e.g., by anchoring or binding) the luciferase in the region of the DNA sequencing templates. It is most preferable to localize the luciferase to a region that is delineated by the distance a PPi molecule can diffuse before it forms ATP. Methods for binding luciferase to a solid support matrix are well-known in the literature (see e.g., Wang, et al., 1997. Specific Immobilization of Firefly Luciferase through a Biotin Carboxyl Carrier Protein Domain, *Analytical Biochem.* 246: 133-139). Thus, for a 2 second diffusion time, the luciferase is anchored within a 50 µm distance of the DNA strand. It should be noted, however, that it would be preferable to decrease the diffusion time and thus to further limit the surface area which is required for luciferase binding.

Additionally, to prevent background generated by diffusion of ATP from one pad to another, the region of substrate between the pads can be coated with immobilized ATPase, especially one that hydrolyzes ATP to ADP, e.g. alkaline phosphatase.

In order to determine the concentration of luciferase which it is necessary to bind, previously published conditions were utilized in which luciferase is used at a concentration which gives a response of 200 mV for 0.1 µm ATP (see Ronaghi, et al., 1996, Real-Time DNA Sequencing Using Detection of Pyrophosphate Release, *Analytical Biochem* 242: 84-89). More specifically, it is known from the literature that, in a 0.2 ml reaction volume, 2 ng of luciferase gives a response of 10 mV for 0.1 µM ATP (see Karamohamed and Nyrén, 1999. Real-Time Detection and Quantification of Adenosine Triphosphate Sulfurylase Activity by a Bioluminometric Approach, *Analytical Biochem.* 271: 81-85). Accordingly, a concentration of 20 ng of luciferase within a 0.2 ml total reaction volume would be required to reproduce these previously-published literature conditions. In the volume of a 10 µm cube around each of the individual anchor pads of the present invention, a luciferase concentration of $1 \times 10^{-16}$ grams would be required, and based upon the 71 kDa molecular weight of luciferase, this concentration would be equivalent to approximately 1000 luciferase molecules. As previously stated, the surface area of luciferase has been computed at 50 $nm^2$. Thus, assuming the luciferase molecules were biotinylated and bound to the anchor pad, 1000 molecules would occupy a total area of 0.05 $\mu m^2$. From these calculations it becomes readily apparent that a plethora of luciferase molecules may be bound to the anchor pad, as the area of each anchor pad area is 100 $\mu m^2$.

Again, based upon previously published results in the literature, each nucleotide takes approximately 3 seconds to sequence (i e., 0.2 second to add a nucleotide; 2 seconds to make ATP; 0.2 seconds to get bioluminescence). Accordingly, a cycle time of approximately 60 seconds per nucleotide is reasonable, requiring approximately 30 minutes per experiment to generate 30 nucleotides of information per sequencing template.

In an alternative embodiment to the aforementioned sequencing methodology (i.e., polymerase→PPi→sulfurylase→ATP→luciferase→-light), a polymerase may be developed (e.g., through the use of protein fusion and the like) which possesses the ability to generate light when it incorporates a nucleotide into a growing DNA chain. In yet another alternative embodiment, a sensor may be developed which directly measures the production of PPi in the sequencing reaction. As the production of PPi changes the electric potential of the surrounding buffer, this change could be measured and calibrated to quantify the concentration of PPi produced.

As previously discussed, the polymerase-mediated incorporation of dNTPs into the nucleotide sequence in the pyrophosphate sequencing reaction causes the release of a photon (i.e., light). The photons generated by the pyrophosphate sequencing reaction may subsequently be "captured" and quantified by a variety of methodologies including, but not limited to: a photomultiplier tube, CCD, absorbance photometer, a luminometer, and the like.

The photons generated by the pyrophosphate sequencing reaction are captured by the CCD. The efficiency of light capture increases if they pass through a focusing device (eg, an optical lens or optical fiber) and are focused upon a CCD element. The fraction of these photons which are captured may be estimated by the following calculations. First, it is assumed that the lens that focuses the emitted photons is at a distance r from the surface of the solid surface (i.e., DNA chip or etched fiber optic well), where r=1 cm, and that the photons must pass through a region of diameter b (area=$\pi b^2/4$) so as to be focused upon the array element, where b=100 µm. (This produces an optical system with numerical aperture of approximately 0.01 in air.) It should also be noted that the emitted photons should escape equally in all directions. At distance r, the photons are dispersed over an area of which is equal to $4\pi r^2$. Thus, the fraction of photons which pass through the lens is described by: $(1/2)[1-(1+b^2/4r^2)^{-1/2}]$. When the value of r is much larger than that of b, the fraction which pass through the lens may then be described by: $b^2/16r^2$. For the aforementioned values of r and b, this fraction of photons is $6 \times 10^{-6}$. Note that the fraction of captured photons increases as b increases or r decreases (i.e. as the numerical aperture of the imaging system increases). Use of FORA in which the microwells are etched into the termini of optical fibers, which then also serve to focus the light onto a CCD, greatly increases the numerical aperture from the example given above, with the numerical aperture of many fiber optics being in the range of 0.7. For each nucleotide addition, it is expected that approximately 10,000 PPi molecules will be generated and, if all are converted by sulfurylase and luciferase, these PPi will result in the emission of approximately $1 \times 10^4$ photons. In order to maximize their subsequent "capture" and quantitation when utilizing a planar array (e.g., a DNA chip), it is preferable to collect the photons immediately at the planar solid support (e.g., the cover slip). This may be accomplished by either: (i) utilizing optical immersion oil between the cover slip and a traditional optical lens or optical fiber bundle or, preferably, (ii) incorporating optical fibers directly into the cover slip itself. Performing the previously described calculations (where in this case, b=100 µm and r=50 µm), the fraction collected is found to be 0.15, which equates to the capture of approximately $1 \times 10^3$ photons. This value would be sufficient to provide an adequate signal.

The following examples are meant to illustrate, not limit, the invention.

EXAMPLE 1

Construction of Anchor Primers Linked to a Cavitated Terminus Fiber Optic Array

The termini of a thin wafer fiber optic array are cavitated by inserting the termini into acid as described by Healey et al., *Anal Chem.* 69: 2213-2216 (1997).

A thin layer of a photoactivatable biotin analog is dried onto the cavitated surface as described in Hengsakul and Cass (*Bioconjugate Chem.* 7: 249-254, 1996) and exposed to white light through a mask to create defined pads, or areas of active biotin. Next, avidin is added and allowed to bind to the biotin. Biotinylated oligonucleotides are then added. The avidin has free biotin binding sites that can anchor biotinylated oligonucleotides through a biotin-avidin-biotin link.

The pads are approximately 10 µm on a side with a 100 µm spacing. Oligonucleotides are added so that approximately 37% of the pads include one anchored primer. On a 1 $cm^2$ surface are deposited 10,000 pads, yielding approximately 3700 pads with a single anchor primer.

EXAMPLE 2

Annealing and Amplification of Members of a Circular Nucleic Acid Library

A library of open circle library templates is prepared from a population of nucleic acids suspected of containing a single nucleotide polymorphism on a 70 bp Sau3A1-MspI fragment The templates include adapters that are complementary to the anchor primer, a region complementary to a sequencing primer, and an insert sequence that is to be characterized. The library is generated using Sau3A1 and MspI to digest the genomic DNA. Inserts approximately 65-75 nucleotides are selected and ligated to adapter oligonucleotides 12 nucleotides in length. The adapter oligonucleotides have sequences complementary to sequences to an anchor primers linked to a substrate surface as described in Example 1.

The library is annealed to the array of anchor primers. A DNA polymerase is added, along with dNTPs, and rolling circle replication is used to extend the anchor primer. The result is a single DNA strand, still anchored to the solid support, that is a concatenation of multiple copies of the circular template. 10,000 or more copies of circular templates in the hundred nucleotide size range.

EXAMPLE 3

Sequence Analysis of Nucleic Acid Linked to the Terminus of a Fiber Optic Substrate The fiber optic array wafer containing amplified nucleic acids as described in Example 2 is placed in a perfusion chamber and attached to a bundle of fiber optic arrays, which are themselves linked to a 16 million pixel CCD camera. A sequencing primer is delivered into the perfusion chamber and allowed to anneal to the amplified sequences. Then sulfurylase, apyrase, and luciferase are attached to the cavitated substrate using biotin-avidin.

The sequencing primer primes DNA synthesis extending into the insert suspected of having a polymorphism, as shown in FIG. 1. The sequencing primer is first extended by delivering into the perfusion chamber, in succession, a wash solution, a DNA polymerase, and one of dTTP, dGTP, dCTP, or α thio dATP (a dATP analog). The sulfurylase, luciferase, and apyrase, attached to the termini convert any PPi liberated as part of the sequencing reaction to detectable light. The apyrase present degrades any unreacted dNTP. Light is typically allowed to collect for 3 seconds (although 1-100, e.g., 2-10 seconds is also suitable) by a CCD camera linked to the fiber imaging bundle, after which additional wash solution is added to the perfusion chamber to remove excess nucleotides and byproducts. The next nucleotide is then added, along with polymerase, thereby repeating the cycle.

During the wash the collected light image is transferred from the CCD camera to a computer. Light emission is analyzed by the computer and used to determine whether the corresponding dNTP has been incorporated into the extended sequence primer. Addition of dNTPs and pyrophosphate sequencing reagents is repeated until the sequence of the insert region containing the suspected polymorphism is obtained.

EXAMPLE 4

Sequence Analysis of a Tandem Repeat Template Generated Using Rolling Circle Amplification A primer having the sequence 5'-gAC CTC ACA CgA Tgg CTg CAg CTT-3' (SEQ ID NO:2) was annealed to a 88 nucleotide template molecule having the sequence 5'-TCg TgT gAg gTC TCA gCA TCT TAT gTA TAT TTA CTT CTA TTC TCA gTT gCC TAA gCT gCA gCC A-3' (SEQ ID NO:1). Annealing of the template to the primer resulted in juxtaposition of the 5' and 3' ands of the template molecule.

The annealed template was exposed to ligase, which resulted in ligation of the 5' and 3' ends of the template to generate a circular molecule.

The annealed primer was extended using Klenow fragment and nucleotides in rolling circle amplification for 12 hours at 37° C. The product was purified using the SPRI technique (Seradyn, Indianapolis, Ind.). Rolling circle amplification resulted in formation of tandem repeats of a sequence complementary to the circular template sequence.

The tandem repeat product in the extended sequence was identified by annealing a sequencing primer having the sequence 5'-AAgCTgCAgCCATCgTgTgAgg-3' (SEQ ID NO:8) and subjecting an annealed primer to 40 alternating cycles of 95° C., 1 minute, 20 seconds, 60° C. using, ET terminator chemistry (Amersham-Pharmacia) in the presence of 1M betaine.

The sequencing product was then diluted to 1/5 volume and purified on a G-50 Sephadex column prior to injection into a MegaBACE sequencing system with linear polyacrylamide (Amersham-Pharmacia).

Figure 5:
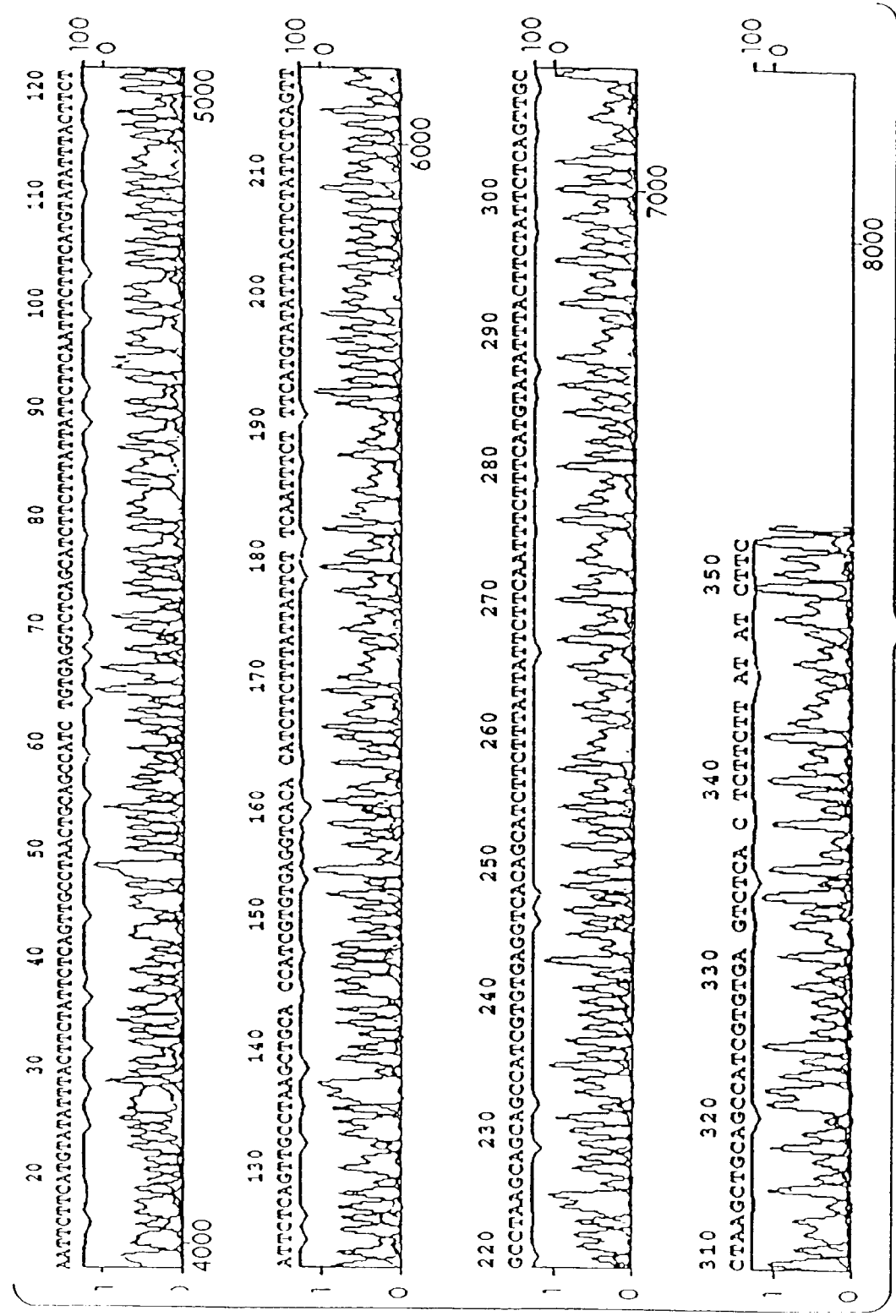
FIG. 5 is a tracing of a sequence output of a concatemeric template generated using rolling circle amplification.
Figure 6:
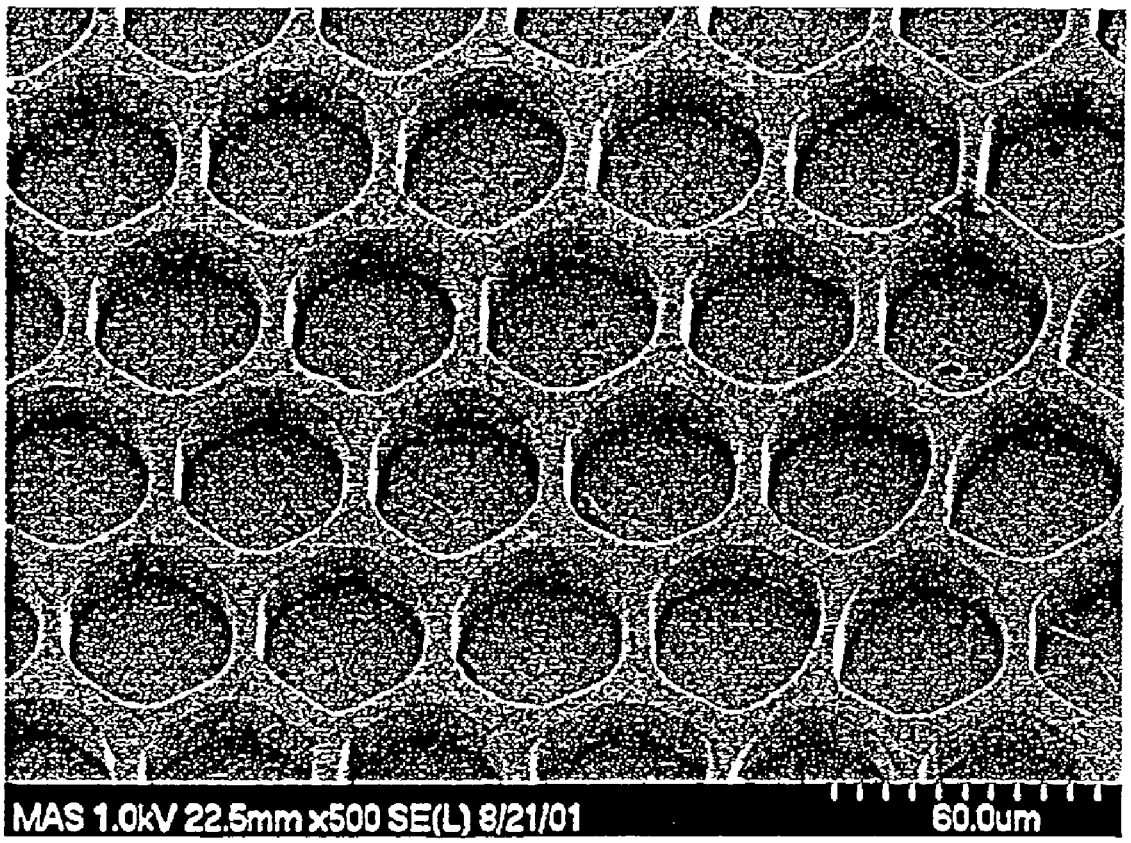
FIG. 6 is a micrograph of a Fiber Optic Reactor Array (FORA).

An electropherogram of the sequencing analysis is shown in FIG. 5. The tracing demonstrates that multiple copies of the 88 bp circular template molecule are generated tandemly, and that these copies can be detected in a DNA sequencing reaction.

EXAMPLE 5

FORA Preparation

DNA beads: Deoxyoligonucleotide—ggggAATTCAAAATTTggC (SEQ ID NO:9) were annealed to capture probes, which were biotinylated at the 5' end, and then immobilized on either Dynal M-280 (Dynal) or MPG beads (CPG) (bead concentration was 1 mg/ml). The immobilization was carried out by incubating the beads, with a fixed amount of oligonucleotide for 30 minutes. Different loadings of oligonucleotide were obtained by changing amount of oligonucleotide used during incubation. After incubation, the beads were washed in respective volumes of TE buffer and resuspended in same volumes of TE.

Enzyme beads: A mixture of 1:1 (vol/vol) of sulfurylase(1 mg/mL) and luciferase(3 mg/mL) with BBCP domains on their N-termini were incubated with equal volume of Dynal M-280 (Dynal) (concentration: 10 mg/mL) for one hour at 4° C. After an hour of incubation the beads were washed with assay buffer (25 mM Tricine, 5 mM MgOAc and 1 mg/mL BSA) four times and then resuspended in same volume of assay buffer.

FORA Preparation: The DNA beads were diluted 10 times to a final concentration of 0.1 mg/mL before use. The enzyme beads were used at 10 mg/mL concentration. The FORA was placed in jig which has 10 spots created by O-rings (3 mm in diameter). 5 uL of DNA beads were delivered, in 9 spots. The first spot on the inlet was a control spot, with no DNA, to detect any background in the reagents. The jig was placed in a centrifuge and spun at 2000 rpm for five minutes. The centrifugal force, forces the beads to the bottom of the wells (approximately 5-10 beads/well) The jig is removed from the centrifuge and 5 uL of SL beads are added and the jig is placed in the centrifuged and the spun at 2000 rpm for five minutes. The process is repeated with 5 uL of SL beads. The FORA is removed from the jig, placed in a falcon tube containing assay buffer and washed by a gentle rocking motion three to four times. The FORA thus prepared is ready for sequence analysis by pyrophosphate sequencing.

EXAMPLE 6

Sequence Analysis of Nucleic Acid Linked to the Terminus of a Fiber Optic Substrate Reagents: Reagents used for sequence analysis and as controls were the four nucleotides and 0.1 µM Pyrophosphate (PPi) were made in substrate solution, where substrate refers to a mixture of 300 µM Luciferin and 4 µM adenosine 5'-phosphosulfate, APS, which are the substrates for the cascade of reactions involving PPi, Luciferase and Sulfurylase. The substrate was made in assay buffer. The concentration of PPi used to test the enzymes and determine the background levels of reagents passing through the chamber was 0.1 µM. The concentration of the nucleotides, dTTP, dGTP, dCTP was 6.5 µM and that of αdATP was 50 µM. Each of the nucleotides was mixed with DNA polymerase, Klenow at a concentration of 100 U/mL.

The FORA was placed in the flow chamber of the embodied instrument, and the flow chamber was attached to the faceplate of the CCD camera. The FORA was washed by flowing substrate (3 ml per min, 2 min) through the chamber. Subsequently, a sequence of reagents was flown through the chamber by the pump connected to an actuator, which was programmed to switch positions, which had tubes inserted in the different reagents. The camera was set up in a fast acquisition mode, with exposure time=2.5 s.

The signal output from the pad is the average of counts on all the pixels within the pad The frame number is equivalent of the time passed during the experiment. The graph indicates the flow of the different reagents.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

We claim:

1. A cuvette for simultaneously monitoring and recording an individual light emission in an array of reaction chambers comprising:

(a) a detection chamber, comprising an opening which comprises an array comprised from a cavitated fiber optic wafer formed from a fused bundle of a plurality of individual optical fibers, wherein each individual optical fiber having a diameter between 3 and 100 μm, the wafer comprising a top surface and a bottom surface, the top surface comprising at least 400,000 reaction chambers, wherein said reaction chambers are etched into the top surface of the cavitated fiber optic wafer and wherein the thickness of the wafer between the top surface and the bottom surface is between 0.5 mm and 5.0 mm in thickness; wherein the depth of each reaction chamber ranges from between one half the diameter of an individual optical fiber and three times the diameter of an individual optical fiber; said detection chamber further comprising at least one surface or opening that allows transmission of said light emission, said reaction chamber adapted to receive at least one analyte;

(b) a receptacle within said detection chamber to align said array with an optical detector; and (c) affluent and effluent outlets connected to said detection chamber to allow said array to be in fluid communication with one or more reagent reservoirs.

2. The cuvette of claim 1 further comprising a plurality of optical fibers that forms an optical fiber bundle; wherein said bundle is capable of transmitting light emitted from said reaction chamber to said optical detector; and wherein each optical fiber is aligned to transmitted the light emission of only one said reaction chamber.

3. The cuvette of claim 2 wherein the optical fiber bundle contains at least one optical fiber per reaction chamber.

4. The cuvette of claim 2 wherein the optical fiber bundle contains at least 4 optical fibers per reaction chamber.

5. The cuvette of claim 1 wherein said detection chamber is adapted to receive a fluid optical coupler to transmit said light emission to said optical detector.

6. The cuvette of claim 5 wherein said fluid optical coupler is microscope oil.

7. The cuvette of claim 5 wherein said fluid optical coupler is an aqueous solution.

8. The cuvette of claim 1 wherein said array is in optical communication with said optical detector through an optical lens.

9. The cuvette of claim 8 wherein said optical lens is a compound lens containing more than one optical element.

10. The cuvette of claim 1 further comprising an optical detection system adapted to detect light emission from each said reaction chamber.

11. The cuvette of claim 10 wherein said optical detection system is a CCD camera.

12. The cuvette of claim 11 wherein said CCD camera comprises at least one individually addressable pixel per said reaction chamber.

13. The cuvette of claim 11 wherein said CCD camera comprises at least 4 individually addressable pixel per said reaction chamber.

14. The cuvette of claim 1 further comprising thermo coupling means to connect said array to a thermal source.

15. The cuvette of claim 14 wherein said thermal source is selected from the group consisting of a heating source, a cooling source, and a combination thereof.

16. The cuvette of claim 1 further comprising a reagent delivery means between said affluent outlet and said one or more reagent reservoir.

17. The cuvette of claim 16 wherein said reagent delivery means is capable of delivering an activated nucleotide 5' triphosphate precursor of one known nitrogenous base to each said reaction chamber.

18. The cuvette of claim 17 wherein said activated nucleotide 5' triphosphate is selected from the group consisting of ATP, GTP, TTP, CTP and UTP.

19. The cuvette of claim 16 wherein said reagent delivery means is connected to one or more reagent reservoirs to sequentially add two or more activated nucleotide 5' triphosphate precursor of one known nitrogenous base to each said reaction chamber.

20. The cuvette of claim 1 further containing reversible coupling means at said affluent and effluent outlets to reversibly connect said cuvette to said one or more reagent reservoirs.

21. The cuvette of claim 1 further comprising a data collection system in communication with the optical detection system.

22. The cuvette of claim 1, wherein the optical detector is a CCD camera.

23. The cuvette of claim 1, wherein the analyte is nucleic acid.

24. The cuvette of claim 1, wherein the analyte is immobilized on one or more mobile solid supports that are disposed in the reaction chamber.

25. A cuvette for simultaneously monitoring and recording an individual light emission in an array of reaction chambers comprising:

(a) a detection chamber, comprising an opening which comprises an array comprised from a cavitated fiber optic wafer formed from a fused bundle of a plurality of individual optical fibers, wherein each individual optical fiber having a diameter between 3 and 100 µm, the wafer comprising a top surface and a bottom surface, the top surface comprising at least 400,000 reaction chambers, wherein said reaction chambers are etched into the top surface of the cavitated fiber optic wafer and wherein the thickness of the wafer between the top surface and the bottom surface is between 0.5 mm and 5.0 mm in thickness; wherein the depth of each reaction chamber ranges from between one half the diameter of an individual optical fiber and three times the diameter of an individual optical fiber; said detection chamber further comprising at least one surface or opening that allows transmission of said light emission, said reaction chamber adapted to receive at least one analyte;

(b) a receptacle within said detection chamber to align said array with an optical detector;

(c) affluent and effluent outlets connected to said detection chamber to allow said array to be in fluid communication with one or more reagent reservoirs; and (d) wherein 50% to 100% of the reaction chambers have a mobile solid support disposed therein, said mobile solid support having at least one pyrophosphate sequencing reagent immobilized thereon.

26. The cuvette of claim 25, wherein the diameter of each individual optical fiber in the cavitated wafer is between 6-50 µm.

27. The cuvette of claim 25, wherein a plurality of the reaction chambers have beads disposed therein, said beads having nucleic acids immobilized thereon.

* * * * *